United States Patent
Taylor et al.

(10) Patent No.: US 9,730,739 B2
(45) Date of Patent: Aug. 15, 2017

(54) ROTARY-RIGID ORTHOPAEDIC ROD

(71) Applicant: Conventus Orthopaedics, Inc., Maple Grove, MN (US)

(72) Inventors: Kyle Taylor, Brooklyn Park, MN (US); Paul Hindrichs, Plymouth, MN (US); Michael P. Brenzel, St. Paul, MN (US)

(73) Assignee: Conventus Orthopaedics, Inc., Maple Grove, MN (US)

( * ) Notice: Subject to any disclaimer, the term of this patent is extended or adjusted under 35 U.S.C. 154(b) by 0 days.

(21) Appl. No.: 13/945,137

(22) Filed: Jul. 18, 2013

(65) Prior Publication Data

US 2014/0058390 A1 Feb. 27, 2014

Related U.S. Application Data

(63) Continuation of application No. 13/005,654, filed on Jan. 13, 2011, now abandoned.

(60) Provisional application No. 61/295,244, filed on Jan. 15, 2010.

(51) Int. Cl.
*A61B 17/72* (2006.01)

(52) U.S. Cl.
CPC ...... *A61B 17/7225* (2013.01); *A61B 17/7208* (2013.01); *A61B 17/7266* (2013.01); *A61B 17/7283* (2013.01)

(58) Field of Classification Search
CPC ................ A61B 17/7002–17/7031; A61B 17/72–17/7291
See application file for complete search history.

(56) References Cited

U.S. PATENT DOCUMENTS

| 1,362,513 A | 12/1919 | Skinner |
| 1,344,327 A | 6/1920 | Wilson |
| 1,493,240 A | 5/1924 | Bohn |

(Continued)

FOREIGN PATENT DOCUMENTS

| CA | 2007210 A1 | 11/1990 |
| CA | 2452508 A1 | 1/2003 |

(Continued)

OTHER PUBLICATIONS

US 7,063,700, 06/2006, Michelson (withdrawn)

(Continued)

*Primary Examiner* — Jan Christopher Merene
*Assistant Examiner* — Steven Cotroneo
(74) *Attorney, Agent, or Firm* — Weiss & Arons LLP

(57) ABSTRACT

Apparatus and method for repairing a fractured bone. The apparatus and methods may involve an intramedullary rod. The rod may include a first elongated member and a second elongated member. Each of the first and second elongated members may be configured to bend in a first direction and to resist bending in a second direction. The first and second elongated members may be arranged such that: (1) the rod is bendable when the first direction of the first elongated member is aligned with the first direction of the second elongated member; and (2) the rod is rigid when the first direction of the first elongated member is aligned with the second direction of the second elongated member. Some embodiments may include rods that have sections that may be configured to be curved and rigid.

28 Claims, 21 Drawing Sheets

(56) References Cited

U.S. PATENT DOCUMENTS

| | | |
|---|---|---|
| 1,685,380 A | 9/1928 | Shultz |
| 2,137,710 A | 12/1937 | Anderson |
| 2,485,531 A | 1/1948 | Dzus et al. |
| 2,493,598 A | 1/1950 | Rozek |
| 2,537,070 A | 1/1951 | Longfellow |
| 2,580,821 A | 1/1952 | Nicola |
| 2,730,101 A | 1/1956 | Hoffman |
| 2,780,223 A | 2/1957 | Haggland |
| 2,898,963 A | 8/1959 | Courtot |
| 3,143,915 A | 8/1964 | Tendler |
| 3,143,916 A | 8/1964 | Rice |
| 3,146,892 A | 9/1964 | White |
| 3,181,533 A | 5/1965 | Heath |
| 3,386,169 A | 6/1968 | Scialom |
| 3,495,586 A | 2/1970 | Regenbogen |
| 3,517,128 A | 6/1970 | Hines |
| 3,593,342 A | 7/1971 | Niebauer et al. |
| 3,602,218 A | 8/1971 | Riordan |
| 3,623,164 A | 11/1971 | Bokros |
| 3,640,280 A | 2/1972 | Slanker et al. |
| 3,702,611 A | 11/1972 | Fishbein |
| 3,710,789 A | 1/1973 | Ersek |
| 3,744,488 A | 7/1973 | Cox |
| 3,745,590 A | 7/1973 | Stubstad |
| 3,759,257 A | 9/1973 | Fischer et al. |
| 3,760,802 A | 9/1973 | Fischer et al. |
| 3,779,239 A | 12/1973 | Fischer et al. |
| 3,805,775 A | 4/1974 | Fischer et al. |
| 3,828,790 A | 8/1974 | Curtiss et al. |
| 3,835,859 A | 9/1974 | Roberts et al. |
| 3,886,600 A | 6/1975 | Kahn et al. |
| 3,909,853 A | 10/1975 | Lennox |
| 3,917,249 A | 11/1975 | Constantine |
| 3,946,445 A | 3/1976 | Bentley et al. |
| 3,970,075 A | 7/1976 | Sindelar et al. |
| 3,986,504 A | 10/1976 | Avila |
| 3,992,726 A | 11/1976 | Freeman et al. |
| 4,036,107 A | 7/1977 | Constantine |
| 4,091,806 A | 5/1978 | Aginsky |
| 4,124,026 A | 11/1978 | Berner et al. |
| 4,156,296 A | 5/1979 | Johnson et al. |
| 4,180,871 A | 1/1980 | Hamas |
| 4,190,044 A | 2/1980 | Wood |
| 4,193,139 A | 3/1980 | Walker |
| 4,194,250 A | 3/1980 | Walker |
| 4,203,444 A | 5/1980 | Bonnell et al. |
| 4,204,531 A | 5/1980 | Aginsky |
| 4,213,208 A | 7/1980 | Marne |
| 4,227,518 A | 10/1980 | Aginsky |
| 4,229,840 A | 10/1980 | Gristina |
| 4,231,121 A | 11/1980 | Lewis |
| 4,262,665 A | 4/1981 | Roalstad et al. |
| 4,273,128 A | 6/1981 | Lary |
| 4,274,398 A | 6/1981 | Scott et al. |
| 4,275,717 A | 6/1981 | Bolesky |
| 4,293,962 A | 10/1981 | Fuson |
| 4,313,434 A | 2/1982 | Segal |
| 4,349,922 A | 9/1982 | Agee |
| 4,352,212 A | 10/1982 | Greene et al. |
| 4,430,991 A | 2/1984 | Darnell |
| 4,438,762 A | 3/1984 | Kyle |
| 4,453,539 A | 6/1984 | Raftopoulos et al. |
| 4,473,070 A | 9/1984 | Matthews et al. |
| 4,485,816 A | 12/1984 | Krumme |
| 4,502,554 A | 3/1985 | Jones |
| 4,519,100 A | 5/1985 | Wills et al. |
| 4,522,200 A | 6/1985 | Stednitz |
| 4,530,114 A | 7/1985 | Tepic |
| 4,548,199 A | 10/1985 | Agee |
| 4,572,186 A | 2/1986 | Gould et al. |
| 4,573,448 A | 3/1986 | Kambin |
| 4,585,000 A | 4/1986 | Hershenson |
| 4,590,930 A | 5/1986 | Kurth et al. |
| 4,601,290 A | 7/1986 | Effron et al. |
| 4,608,965 A | 9/1986 | Anspach, Jr. et al. |
| 4,611,594 A | 9/1986 | Grayhack et al. |
| 4,619,122 A | 10/1986 | Simpson |
| 4,627,434 A | 12/1986 | Murray |
| 4,634,445 A | 1/1987 | Helal |
| 4,643,177 A | 2/1987 | Sheppard et al. |
| 4,644,951 A | 2/1987 | Bays |
| 4,646,738 A | 3/1987 | Trott |
| 4,655,203 A | 4/1987 | Tormala et al. |
| 4,660,557 A | 4/1987 | Collis |
| 4,662,371 A | 5/1987 | Whipple et al. |
| 4,665,906 A | 5/1987 | Jervis |
| 4,669,237 A | 6/1987 | Constantine |
| 4,674,488 A | 6/1987 | Nashef et al. |
| 4,705,027 A | 11/1987 | Klaue |
| 4,706,659 A | 11/1987 | Matthews et al. |
| 4,721,103 A | 1/1988 | Freedland |
| 4,730,608 A | 3/1988 | Schlein |
| 4,731,087 A | 3/1988 | Sculco et al. |
| 4,751,922 A | 6/1988 | DiPietropolo |
| 4,772,261 A | 9/1988 | Von Hoff et al. |
| 4,777,942 A | 10/1988 | Frey et al. |
| 4,782,833 A | 11/1988 | Einhorn et al. |
| 4,790,302 A | 12/1988 | Colwill et al. |
| 4,809,793 A | 3/1989 | Hailey |
| 4,820,305 A | 4/1989 | Harms et al. |
| 4,875,474 A | 10/1989 | Border |
| 4,886,062 A | 12/1989 | Wiktor |
| 4,914,818 A | 4/1990 | Hall et al. |
| 4,921,478 A | 5/1990 | Solano et al. |
| 4,941,466 A | 7/1990 | Romano |
| 4,946,459 A | 8/1990 | Bradshaw et al. |
| 4,954,126 A | 9/1990 | Wallsten |
| 4,955,916 A | 9/1990 | Carignan et al. |
| 4,969,888 A | 11/1990 | Scholten et al. |
| 4,973,257 A | 11/1990 | Lhotak |
| 4,978,349 A | 12/1990 | Frigg |
| 4,998,539 A | 3/1991 | Delsanti |
| 5,002,546 A | 3/1991 | Romano |
| 5,015,255 A | 5/1991 | Kuslich |
| 5,030,201 A | 7/1991 | Palestrant |
| 5,035,714 A | 7/1991 | Willert et al. |
| 5,053,036 A | 10/1991 | Perren et al. |
| 5,057,103 A | 10/1991 | Davis |
| 5,059,193 A | 10/1991 | Kuslich |
| 5,059,206 A | 10/1991 | Winters |
| 5,062,845 A | 11/1991 | Kuslich et al. |
| 5,066,296 A | 11/1991 | Chapman et al. |
| 5,067,957 A | 11/1991 | Jervis |
| 5,071,407 A | 12/1991 | Termin et al. |
| 5,084,050 A | 1/1992 | Draenert |
| 5,100,423 A | 3/1992 | Fearnot |
| 5,102,413 A | 4/1992 | Poddar |
| 5,108,404 A | 4/1992 | Scholten et al. |
| 5,108,435 A | 4/1992 | Gustavson et al. |
| 5,112,333 A | 5/1992 | Fixel |
| 5,113,846 A | 5/1992 | Hiltebrandt et al. |
| 5,116,335 A | 5/1992 | Hannon et al. |
| 5,122,134 A | 6/1992 | Borzone et al. |
| 5,129,906 A | 7/1992 | Ross et al. |
| 5,135,527 A | 8/1992 | Ender |
| 5,139,497 A | 8/1992 | Tilghman et al. |
| 5,151,103 A | 9/1992 | Tepic et al. |
| 5,169,402 A | 12/1992 | Elloy |
| 5,171,284 A | 12/1992 | Branemark |
| 5,174,374 A | 12/1992 | Hailey |
| 5,180,382 A | 1/1993 | Frigg et al. |
| 5,190,545 A | 3/1993 | Corsi et al. |
| 5,190,546 A | 3/1993 | Jervis |
| 5,190,548 A | 3/1993 | Davis |
| 5,197,966 A | 3/1993 | Sommerkamp |
| 5,197,967 A | 3/1993 | Wilson |
| 5,197,971 A | 3/1993 | Bonutti |
| 5,201,741 A | 4/1993 | Dulebohn |
| 5,203,773 A | 4/1993 | Green |
| 5,221,261 A | 6/1993 | Termin et al. |
| 5,236,431 A | 8/1993 | Gogolewski et al. |
| 5,242,017 A | 9/1993 | Hailey |
| 5,242,461 A | 9/1993 | Kortenbach et al. |
| 5,250,048 A | 10/1993 | Gundolf |

(56) References Cited

U.S. PATENT DOCUMENTS

| | | |
|---|---|---|
| 5,263,955 A | 11/1993 | Baumgart et al. |
| 5,269,785 A | 12/1993 | Bonutti |
| 5,275,602 A | 1/1994 | Shimizu et al. |
| 5,275,608 A | 1/1994 | Forman et al. |
| 5,281,225 A | 1/1994 | Vicenzi |
| 5,281,226 A | 1/1994 | Davydov et al. |
| 5,286,249 A | 2/1994 | Thibodaux |
| 5,307,790 A | 5/1994 | Byrne |
| 5,314,486 A | 5/1994 | Zang et al. |
| 5,326,205 A | 7/1994 | Anspach et al. |
| 5,334,184 A | 8/1994 | Bimman |
| 5,358,405 A | 10/1994 | Imai |
| 5,376,097 A | 12/1994 | Phillips |
| 5,376,100 A | 12/1994 | Lefebvre |
| 5,378,239 A | 1/1995 | Termin et al. |
| 5,380,328 A | 1/1995 | Morgan |
| 5,397,320 A | 3/1995 | Essig et al. |
| 5,415,660 A | 5/1995 | Campbell et al. |
| 5,423,823 A | 6/1995 | Schmieding |
| 5,431,671 A | 7/1995 | Nallakrishnan |
| 5,437,665 A | 8/1995 | Munro |
| 5,437,674 A | 8/1995 | Worcel et al. |
| 5,439,464 A | 8/1995 | Shapiro |
| 5,445,639 A | 8/1995 | Kuslich et al. |
| 5,454,365 A | 10/1995 | Bonutti |
| 5,458,599 A | 10/1995 | Adobbati |
| 5,458,648 A | 10/1995 | Berman et al. |
| 5,462,547 A | 10/1995 | Weigum |
| 5,467,763 A | 11/1995 | McMahon et al. |
| D365,634 S | 12/1995 | Morgan |
| 5,474,557 A | 12/1995 | Mai |
| 5,480,447 A | 1/1996 | Skiba |
| 5,496,277 A | 3/1996 | Termin et al. |
| 5,496,330 A | 3/1996 | Bates et al. |
| 5,499,981 A | 3/1996 | Kordis |
| 5,501,695 A | 3/1996 | Anspach et al. |
| 5,505,734 A | 4/1996 | Caniggia et al. |
| 5,509,919 A | 4/1996 | Young |
| 5,512,037 A | 4/1996 | Russell et al. |
| 5,527,316 A | 6/1996 | Stone et al. |
| 5,531,792 A | 7/1996 | Huene |
| 5,536,267 A | 7/1996 | Edwards et al. |
| 5,540,693 A | 7/1996 | Fisher |
| 5,545,162 A | 8/1996 | Huebner |
| 5,554,163 A | 9/1996 | Shturman |
| 5,556,408 A | 9/1996 | Farhat |
| 5,571,098 A | 11/1996 | Domankevitz et al. |
| 5,571,189 A | 11/1996 | Kuslich |
| 5,578,035 A | 11/1996 | Lin |
| 5,582,577 A | 12/1996 | Lund et al. |
| 5,582,618 A | 12/1996 | Chin et al. |
| 5,586,983 A | 12/1996 | Sanders et al. |
| 5,586,985 A | 12/1996 | Putnam et al. |
| 5,586,990 A | 12/1996 | Hahnen et al. |
| 5,591,169 A | 1/1997 | Benoist |
| 5,591,170 A | 1/1997 | Spievack et al. |
| 5,597,378 A | 1/1997 | Jervis |
| 5,602,935 A | 2/1997 | Yoshida et al. |
| 5,620,414 A | 4/1997 | Campbell |
| 5,620,445 A | 4/1997 | Brosnahan et al. |
| 5,624,440 A | 4/1997 | Huebner |
| 5,624,447 A | 4/1997 | Myers |
| 5,626,580 A | 5/1997 | Brosnahan |
| 5,628,747 A | 5/1997 | Richelsoph |
| 5,645,589 A | 7/1997 | Li |
| 5,658,280 A | 8/1997 | Issa |
| 5,658,283 A | 8/1997 | Huebner |
| 5,660,188 A | 8/1997 | Groiso |
| 5,662,649 A | 9/1997 | Huebner |
| 5,667,509 A | 9/1997 | Westin |
| 5,676,545 A | 10/1997 | Jones |
| 5,676,699 A | 10/1997 | Gogolewski et al. |
| 5,681,310 A | 10/1997 | Yuan et al. |
| 5,683,389 A | 11/1997 | Orsak |
| 5,685,826 A | 11/1997 | Bonutti |
| 5,693,011 A | 12/1997 | Onik |
| 5,697,981 A | 12/1997 | Ison et al. |
| 5,707,374 A | 1/1998 | Schmidt |
| 5,709,697 A | 1/1998 | Ratcliff et al. |
| 5,718,704 A | 2/1998 | Medoff |
| 5,725,541 A | 3/1998 | Anspach, III et al. |
| 5,728,047 A | 3/1998 | Edoga |
| 5,728,098 A | 3/1998 | Sherman et al. |
| 5,730,704 A | 3/1998 | Avitall |
| 5,741,266 A | 4/1998 | Moran et al. |
| 5,741,282 A | 4/1998 | Anspach et al. |
| 5,758,713 A | 6/1998 | Fallet |
| 5,779,703 A | 7/1998 | Benoist |
| 5,792,106 A | 8/1998 | Mische |
| 5,810,721 A | 9/1998 | Mueller et al. |
| 5,814,044 A | 9/1998 | Hooven |
| 5,817,098 A | 10/1998 | Albrektsson et al. |
| 5,824,095 A | 10/1998 | Di Maio, Jr. et al. |
| 5,827,289 A | 10/1998 | Reiley et al. |
| 5,827,312 A | 10/1998 | Brown et al. |
| D403,069 S | 12/1998 | Drewry et al. |
| 5,853,054 A | 12/1998 | McGarian et al. |
| 5,876,399 A | 3/1999 | Chia et al. |
| 5,879,352 A * | 3/1999 | Filoso et al. .................. 606/62 |
| 5,879,355 A | 3/1999 | Ullmark |
| 5,885,258 A | 3/1999 | Sachdeva et al. |
| 5,885,282 A | 3/1999 | Szabo |
| 5,888,196 A | 3/1999 | Bonutti |
| 5,891,147 A | 4/1999 | Moskovitz et al. |
| 5,893,850 A | 4/1999 | Cachia |
| 5,897,556 A | 4/1999 | Drewry et al. |
| 5,908,423 A | 6/1999 | Kashuba et al. |
| 5,915,036 A | 6/1999 | Grunkin et al. |
| 5,919,195 A | 7/1999 | Wilson et al. |
| 5,925,039 A | 7/1999 | Landingham |
| 5,928,239 A | 7/1999 | Mirza |
| 5,935,127 A | 8/1999 | Border |
| 5,938,699 A | 8/1999 | Campbell |
| 5,941,878 A | 8/1999 | Medoff |
| 5,951,467 A | 9/1999 | Picha et al. |
| 5,951,556 A | 9/1999 | Faccioli et al. |
| 5,957,884 A | 9/1999 | Hooven |
| 5,964,698 A | 10/1999 | Fowle |
| 5,976,134 A | 11/1999 | Huebner |
| 5,980,525 A | 11/1999 | Bryant et al. |
| 5,984,932 A | 11/1999 | Yoon |
| 5,984,937 A | 11/1999 | Morse et al. |
| 5,997,538 A | 12/1999 | Asnis et al. |
| 6,001,099 A | 12/1999 | Huebner |
| 6,015,406 A | 1/2000 | Goble et al. |
| 6,019,762 A | 2/2000 | Cole |
| 6,019,947 A | 2/2000 | Kucherov |
| 6,030,406 A | 2/2000 | Davis et al. |
| 6,033,412 A | 3/2000 | Losken et al. |
| 6,045,564 A | 4/2000 | Walen |
| 6,048,309 A | 4/2000 | Flom et al. |
| 6,053,922 A | 4/2000 | Krause et al. |
| 6,056,750 A | 5/2000 | Lob |
| 6,068,642 A | 5/2000 | Johnson et al. |
| 6,068,648 A | 5/2000 | Cole et al. |
| 6,074,392 A | 6/2000 | Durham |
| 6,093,162 A | 7/2000 | Fairleigh et al. |
| 6,096,040 A | 8/2000 | Esser |
| 6,113,603 A | 9/2000 | Medoff |
| 6,120,472 A | 9/2000 | Singer |
| 6,120,504 A | 9/2000 | Brumback et al. |
| 6,123,704 A | 9/2000 | Hajianpour |
| 6,126,662 A | 10/2000 | Carmichael et al. |
| 6,127,597 A | 10/2000 | Beyar et al. |
| 6,129,762 A | 10/2000 | Li |
| 6,142,935 A | 11/2000 | Flom et al. |
| 6,143,012 A | 11/2000 | Gausepohl |
| 6,149,651 A | 11/2000 | Drewry et al. |
| 6,149,689 A | 11/2000 | Grundei |
| 6,156,069 A | 12/2000 | Amstutz |
| 6,162,223 A | 12/2000 | Orsak et al. |
| 6,162,224 A | 12/2000 | Huebner |
| 6,171,309 B1 | 1/2001 | Huebner |
| 6,174,312 B1 | 1/2001 | Laminger |

(56) References Cited

U.S. PATENT DOCUMENTS

| | | |
|---|---|---|
| 6,197,027 B1 | 3/2001 | Hajianpour |
| 6,200,330 B1 | 3/2001 | Benderev et al. |
| 6,216,573 B1 | 4/2001 | Moutafis et al. |
| 6,221,074 B1 | 4/2001 | Cole et al. |
| 6,221,102 B1 | 4/2001 | Baker et al. |
| 6,224,600 B1 | 5/2001 | Protogirou |
| 6,224,604 B1 | 5/2001 | Suddaby |
| 6,231,576 B1 | 5/2001 | Frigg et al. |
| 6,235,043 B1 | 5/2001 | Reiley et al. |
| 6,238,417 B1 | 5/2001 | Cole |
| 6,241,734 B1 | 6/2001 | Scribner et al. |
| 6,248,110 B1 | 6/2001 | Reiley et al. |
| 6,258,096 B1 | 7/2001 | Seki |
| 6,261,289 B1 | 7/2001 | Levy |
| 6,280,474 B1 | 8/2001 | Cassidy et al. |
| 6,296,639 B1 | 10/2001 | Truckai et al. |
| 6,299,642 B1 | 10/2001 | Chan |
| 6,302,915 B1 | 10/2001 | Cooney et al. |
| 6,306,141 B1 | 10/2001 | Jervis |
| 6,312,467 B1 | 11/2001 | Mcgee |
| 6,319,255 B1 | 11/2001 | Grundei et al. |
| 6,322,591 B1 | 11/2001 | Ahrens |
| 6,331,166 B1 | 12/2001 | Burbank et al. |
| 6,332,885 B1 | 12/2001 | Martella |
| 6,332,886 B1 | 12/2001 | Green et al. |
| 6,348,053 B1 | 2/2002 | Cachia |
| 6,364,909 B1 | 4/2002 | Mcgee |
| 6,365,555 B1 | 4/2002 | Moser et al. |
| 6,375,666 B1 | 4/2002 | Mische |
| 6,383,188 B2 | 5/2002 | Kuslich et al. |
| 6,402,753 B1 | 6/2002 | Cole et al. |
| 6,411,729 B1 | 6/2002 | Grunkin |
| 6,416,517 B2 | 7/2002 | Harder et al. |
| 6,423,070 B1 | 7/2002 | Zeppelin |
| 6,440,138 B1 | 8/2002 | Reiley et al. |
| 6,447,514 B1 | 9/2002 | Stalcup et al. |
| 6,447,515 B1 | 9/2002 | Meldrum |
| 6,447,518 B1 | 9/2002 | Krause et al. |
| 6,454,810 B1 | 9/2002 | Lob |
| 6,468,207 B1 | 10/2002 | Fowler |
| 6,475,789 B1 | 11/2002 | Cech et al. |
| 6,488,685 B1 | 12/2002 | Manderson |
| 6,491,694 B1 | 12/2002 | Orsak |
| 6,511,481 B2 | 1/2003 | von Hoffmann et al. |
| 6,517,541 B1 | 2/2003 | Sesic |
| 6,527,775 B1 | 3/2003 | Warburton |
| 6,533,788 B1 | 3/2003 | Orbay |
| 6,540,770 B1 | 4/2003 | Tornier et al. |
| 6,544,267 B1 | 4/2003 | Cole et al. |
| 6,551,321 B1 | 4/2003 | Burkinshaw et al. |
| 6,554,833 B2 | 4/2003 | Levy et al. |
| 6,575,878 B1 | 6/2003 | Choy |
| 6,575,973 B1 | 6/2003 | Shekalim |
| 6,575,978 B2 | 6/2003 | Peterson et al. |
| 6,582,467 B1 | 6/2003 | Teitelbaum et al. |
| 6,585,736 B2 | 7/2003 | Hajianpour |
| 6,585,770 B1 | 7/2003 | White et al. |
| 6,610,839 B1 | 8/2003 | Morin et al. |
| 6,613,052 B1 | 9/2003 | Kinnett |
| 6,613,054 B2 | 9/2003 | Scribner et al. |
| 6,617,110 B1 | 9/2003 | Cech et al. |
| 6,632,224 B2 | 10/2003 | Cachia et al. |
| 6,641,616 B1 | 11/2003 | Grundei |
| 6,645,210 B2 | 11/2003 | Manderson |
| 6,648,890 B2 | 11/2003 | Culbert et al. |
| 6,652,585 B2 | 11/2003 | Lange |
| 6,656,187 B1 | 12/2003 | Camino |
| 6,656,219 B1 | 12/2003 | Wiktor |
| 6,660,009 B1 | 12/2003 | Azar |
| 6,660,041 B1 | 12/2003 | Grundei |
| 6,676,665 B2 | 1/2004 | Foley et al. |
| 6,679,886 B2 | 1/2004 | Weikel et al. |
| 6,682,565 B1 | 1/2004 | Krishnan |
| 6,685,706 B2 | 2/2004 | Padget et al. |
| 6,689,138 B2 | 2/2004 | Léchot et al. |
| 6,692,496 B1 | 2/2004 | Wardlaw |
| 6,701,174 B1 | 3/2004 | Krause et al. |
| 6,709,433 B1 | 3/2004 | Schoenefeld |
| 6,711,432 B1 | 3/2004 | Krause et al. |
| 6,712,073 B2 | 3/2004 | Manderson |
| 6,712,858 B1 | 3/2004 | Grundei et al. |
| 6,719,761 B1 | 4/2004 | Reiley et al. |
| 6,719,793 B2 | 4/2004 | McGee et al. |
| 6,746,451 B2 | 6/2004 | Middleton et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,761,722 B2 | 7/2004 | Cole et al. |
| 6,767,350 B1 | 7/2004 | Lob |
| 6,775,401 B2 | 8/2004 | Hwang et al. |
| 6,780,185 B2 | 8/2004 | Frei et al. |
| 6,783,530 B1 | 8/2004 | Levy et al. |
| 6,783,532 B2 | 8/2004 | Steiner et al. |
| 6,783,533 B2 | 8/2004 | Green et al. |
| 6,793,655 B2 | 9/2004 | Orsak |
| 6,793,659 B2 | 9/2004 | Putnam |
| 6,811,568 B2 | 11/2004 | Minamikawa |
| 6,827,723 B2 | 12/2004 | Carson |
| 6,827,743 B2 | 12/2004 | Eisermann et al. |
| 6,849,051 B2 | 2/2005 | Sramek et al. |
| 6,852,128 B2 | 2/2005 | Lange |
| 6,866,665 B2 | 3/2005 | Orbay |
| 6,887,243 B2 | 5/2005 | Culbert |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,911,046 B2 | 6/2005 | Schulter |
| 6,913,605 B2 | 7/2005 | Fletcher et al. |
| 6,923,813 B2 | 8/2005 | Phillips et al. |
| 6,923,817 B2 | 8/2005 | Carson et al. |
| 6,923,828 B1 | 8/2005 | Wiktor |
| 6,926,720 B2 | 8/2005 | Castañeda |
| 6,932,086 B1 | 8/2005 | Hajianpour |
| 6,942,666 B2 | 9/2005 | Overaker et al. |
| 6,942,668 B2 | 9/2005 | Padget et al. |
| 6,949,101 B2 | 9/2005 | McCleary et al. |
| 6,951,561 B2 | 10/2005 | Warren et al. |
| 6,953,313 B2 | 10/2005 | Tylosky |
| 6,975,894 B2 | 12/2005 | Wehrli et al. |
| 6,984,248 B2 | 1/2006 | Hyde, Jr. |
| 6,986,771 B2 | 1/2006 | Paul et al. |
| 6,989,011 B2 | 1/2006 | Paul et al. |
| 6,991,656 B2 | 1/2006 | Mears |
| 7,008,425 B2 | 3/2006 | Phillips |
| 7,008,428 B2 | 3/2006 | Cachia et al. |
| 7,008,430 B2 | 3/2006 | Dong et al. |
| 7,011,662 B2 | 3/2006 | Lechot et al. |
| 7,018,332 B1 | 3/2006 | Masson et al. |
| 7,018,380 B2 | 3/2006 | Cole |
| 7,022,069 B1 | 4/2006 | Masson et al. |
| 7,025,789 B2 | 4/2006 | Chow et al. |
| 7,041,104 B1 | 5/2006 | Cole et al. |
| 7,041,138 B2 | 5/2006 | Lange |
| 7,048,542 B2 | 5/2006 | Von Arx et al. |
| 7,052,498 B2 | 5/2006 | Levy et al. |
| 7,063,701 B2 | 6/2006 | Michelson |
| 7,070,601 B2 | 7/2006 | Culbert et al. |
| 7,090,676 B2 | 8/2006 | Huebner et al. |
| 7,097,646 B2 | 8/2006 | Schantz |
| 7,097,648 B1 | 8/2006 | Globerman et al. |
| 7,122,033 B2 | 10/2006 | Wood |
| 7,122,043 B2 | 10/2006 | Greenhalgh et al. |
| 7,122,052 B2 | 10/2006 | Greenhalgh |
| 7,131,995 B2 | 11/2006 | Biedermann et al. |
| 7,137,987 B2 | 11/2006 | Patterson et al. |
| 7,141,054 B2 | 11/2006 | Vandewalle |
| 7,141,067 B2 | 11/2006 | Jones et al. |
| 7,147,640 B2 | 12/2006 | Huebner et al. |
| 7,153,307 B2 | 12/2006 | Scribner et al. |
| 7,153,309 B2 | 12/2006 | Huebner et al. |
| 7,160,302 B2 | 1/2007 | Warburton |
| 7,160,331 B2 | 1/2007 | Cooney et al. |
| 7,172,595 B1 | 2/2007 | Goble |
| 7,175,625 B2 | 2/2007 | Culbert |

(56) References Cited

U.S. PATENT DOCUMENTS

| | | |
|---|---|---|
| 7,179,024 B2 | 2/2007 | Greenhalgh |
| 7,189,237 B2 | 3/2007 | Huebner |
| 7,189,240 B1 | 3/2007 | Dekel |
| 7,195,589 B1 | 3/2007 | Masson et al. |
| 7,195,633 B2 | 3/2007 | Medoff et al. |
| 7,214,227 B2 | 5/2007 | Colleran et al. |
| 7,220,282 B2 | 5/2007 | Kuslich et al. |
| 7,229,441 B2 | 6/2007 | Trieu et al. |
| 7,235,079 B2 | 6/2007 | Jensen et al. |
| 7,237,556 B2 | 7/2007 | Smothers et al. |
| 7,255,712 B1 | 8/2007 | Steinberg |
| 7,258,692 B2 | 8/2007 | Thelen et al. |
| 7,264,622 B2 | 9/2007 | Michelson |
| 7,267,678 B2 | 9/2007 | Medoff |
| 7,282,053 B2 | 10/2007 | Orbay |
| 7,294,130 B2 | 11/2007 | Orbay |
| 7,300,449 B2 | 11/2007 | Mische et al. |
| 7,306,603 B2 | 12/2007 | Boehm et al. |
| 7,306,683 B2 | 12/2007 | Cheung et al. |
| 7,311,711 B2 | 12/2007 | Cole |
| D560,128 S | 1/2008 | Diederich et al. |
| 7,322,938 B2 | 1/2008 | Burbank et al. |
| 7,326,249 B2 | 2/2008 | Lange |
| 7,329,228 B2 | 2/2008 | Burbank et al. |
| 7,341,601 B2 | 3/2008 | Eisermann et al. |
| 7,344,539 B2 | 3/2008 | Serhan et al. |
| 7,354,453 B2 | 4/2008 | McAfee |
| 7,413,563 B2 | 8/2008 | Corcoran et al. |
| 7,422,360 B2 | 9/2008 | Kozyuk |
| 7,465,318 B2 | 12/2008 | Sennett et al. |
| 7,476,226 B2 | 1/2009 | Weikel et al. |
| 7,481,815 B2 | 1/2009 | Fernandez |
| 7,485,119 B2 | 2/2009 | Thelen et al. |
| 7,488,320 B2 | 2/2009 | Middleton |
| 7,488,329 B2 | 2/2009 | Thelen et al. |
| D589,147 S | 3/2009 | Colleran et al. |
| 7,500,977 B2 | 3/2009 | Assell et al. |
| 7,507,241 B2 | 3/2009 | Levy et al. |
| 7,520,879 B2 | 4/2009 | Justis et al. |
| 7,527,632 B2 | 5/2009 | Houghton et al. |
| 7,563,263 B2 | 7/2009 | Orbay et al. |
| 7,569,061 B2 | 8/2009 | Colleran |
| 7,578,824 B2 | 8/2009 | Justin et al. |
| 7,588,575 B2 | 9/2009 | Colleran et al. |
| 7,588,577 B2 | 9/2009 | Fencl et al. |
| 7,588,588 B2 | 9/2009 | Spitler et al. |
| 7,601,152 B2 | 10/2009 | Levy et al. |
| 7,611,515 B2 | 11/2009 | Wolford et al. |
| 7,621,950 B1 | 11/2009 | Globerman et al. |
| 7,632,277 B2 | 12/2009 | Woll et al. |
| 7,632,310 B2 | 12/2009 | Clifford et al. |
| 7,666,226 B2 | 2/2010 | Schaller |
| 7,670,339 B2 | 3/2010 | Levy et al. |
| 7,670,374 B2 | 3/2010 | Schaller |
| 7,670,375 B2 | 3/2010 | Schaller |
| 7,682,364 B2 | 3/2010 | Reiley et al. |
| 7,695,471 B2 | 4/2010 | Cheung et al. |
| 7,695,502 B2 | 4/2010 | Orbay et al. |
| 7,704,251 B2 | 4/2010 | Huebner et al. |
| 7,708,742 B2 | 5/2010 | Scribner et al. |
| 7,713,271 B2 | 5/2010 | Warburton et al. |
| 7,717,472 B2 | 5/2010 | Johnson |
| 7,722,612 B2 | 5/2010 | Sala et al. |
| 7,722,626 B2 | 5/2010 | Middleman et al. |
| 7,727,264 B2 | 6/2010 | Orbay et al. |
| 7,731,720 B2 | 6/2010 | Sand et al. |
| 7,749,232 B2 | 7/2010 | Salerni |
| 7,758,500 B2 | 7/2010 | Boyd et al. |
| 7,785,368 B2 | 8/2010 | Schaller |
| 7,806,929 B2 | 10/2010 | Brown |
| 7,811,291 B2 | 10/2010 | Liu et al. |
| 7,828,802 B2 * | 11/2010 | Levy et al. ............... 606/63 |
| 7,837,612 B2 | 11/2010 | Gill et al. |
| 7,842,041 B2 | 11/2010 | Liu et al. |
| 7,846,162 B2 | 12/2010 | Nelson et al. |
| 7,879,103 B2 | 2/2011 | Gertzman et al. |
| 7,905,909 B2 | 3/2011 | Orbay et al. |
| 7,909,825 B2 | 3/2011 | Saravia et al. |
| 7,909,827 B2 | 3/2011 | Reiley et al. |
| 7,909,873 B2 | 3/2011 | Tan-Malecki et al. |
| 7,914,533 B2 | 3/2011 | Nelson et al. |
| 7,931,689 B2 | 4/2011 | Hochschuler et al. |
| 7,942,875 B2 | 5/2011 | Nelson et al. |
| 7,959,634 B2 | 6/2011 | Sennett |
| 7,959,638 B2 | 6/2011 | Osorio et al. |
| 7,959,683 B2 | 6/2011 | Semler et al. |
| 7,967,827 B2 | 6/2011 | Osorio et al. |
| 7,967,865 B2 | 6/2011 | Schaller |
| 7,972,340 B2 | 7/2011 | Sand et al. |
| 7,988,735 B2 | 8/2011 | Yurek et al. |
| 8,007,498 B2 | 8/2011 | Mische |
| RE42,757 E | 9/2011 | Kuslich et al. |
| 8,021,365 B2 | 9/2011 | Phan |
| 8,021,366 B2 | 9/2011 | Phan |
| 8,043,334 B2 | 10/2011 | Fisher et al. |
| 8,057,544 B2 | 11/2011 | Schaller |
| 8,105,236 B2 | 1/2012 | Malandain et al. |
| 8,109,933 B2 | 2/2012 | Truckai et al. |
| 8,114,084 B2 | 2/2012 | Betts |
| 8,118,952 B2 | 2/2012 | Gall et al. |
| 8,128,627 B2 | 3/2012 | Justin et al. |
| 8,152,737 B2 | 4/2012 | Burbank et al. |
| 8,157,804 B2 | 4/2012 | Betts |
| 8,226,719 B2 | 7/2012 | Melsheimer et al. |
| 8,241,335 B2 | 8/2012 | Truckai et al. |
| 8,287,538 B2 | 10/2012 | Brenzel et al. |
| 8,287,539 B2 | 10/2012 | Nelson et al. |
| 8,287,541 B2 | 10/2012 | Nelson et al. |
| 8,317,791 B2 | 11/2012 | Phan |
| 8,353,911 B2 | 1/2013 | Goldin et al. |
| 8,366,773 B2 | 2/2013 | Schaller et al. |
| 8,409,211 B2 | 4/2013 | Baroud |
| 8,430,879 B2 | 4/2013 | Stoneburner et al. |
| 8,439,917 B2 | 5/2013 | Saravia et al. |
| 8,485,798 B2 | 7/2013 | Sheth et al. |
| 8,491,591 B2 | 7/2013 | Fürderer |
| 8,496,394 B2 | 7/2013 | Schneider |
| 8,496,658 B2 | 7/2013 | Stoneburner et al. |
| 8,500,357 B2 | 8/2013 | Stahle |
| 8,505,879 B2 | 8/2013 | Ruan |
| 8,506,199 B2 | 8/2013 | Rump et al. |
| 8,512,398 B2 | 8/2013 | Alkhatib |
| 8,568,413 B2 * | 10/2013 | Mazur et al. ............... 606/62 |
| 8,579,537 B2 | 11/2013 | VanLandingham et al. |
| 8,597,276 B2 | 12/2013 | Vongphakdy et al. |
| 9,155,574 B2 | 10/2015 | Saravia et al. |
| 2001/0008704 A1 * | 7/2001 | Harder et al. ............ 428/573 |
| 2001/0018588 A1 | 8/2001 | Harder et al. |
| 2001/0034526 A1 | 10/2001 | Kuslich et al. |
| 2001/0053912 A1 | 12/2001 | Frigg |
| 2002/0013600 A1 | 1/2002 | Scribner et al. |
| 2002/0015517 A1 | 2/2002 | Hwang et al. |
| 2002/0029081 A1 | 3/2002 | Scarborough et al. |
| 2002/0032444 A1 | 3/2002 | Mische |
| 2002/0055742 A1 | 5/2002 | Lieberman |
| 2002/0055785 A1 | 5/2002 | Harris |
| 2002/0065530 A1 | 5/2002 | Mische |
| 2002/0068974 A1 | 6/2002 | Kuslich et al. |
| 2002/0111629 A1 | 8/2002 | Phillips |
| 2002/0111690 A1 | 8/2002 | Hyde |
| 2002/0120269 A1 | 8/2002 | Lange |
| 2002/0120270 A1 | 8/2002 | Trieu et al. |
| 2002/0123750 A1 | 9/2002 | Eisermann et al. |
| 2002/0133153 A1 | 9/2002 | Hyde |
| 2002/0133156 A1 | 9/2002 | Cole |
| 2002/0133172 A1 | 9/2002 | Lambrecht et al. |
| 2002/0133175 A1 | 9/2002 | Carson |
| 2002/0138149 A1 | 9/2002 | Hyde |
| 2002/0143329 A1 | 10/2002 | Serhan et al. |
| 2002/0143333 A1 | 10/2002 | von Hoffmann et al. |
| 2002/0143334 A1 | 10/2002 | Hoffmann et al. |
| 2002/0143335 A1 | 10/2002 | von Hoffmann et al. |
| 2002/0147451 A1 | 10/2002 | Mcgee |
| 2002/0147455 A1 | 10/2002 | Carson |

(56) References Cited

U.S. PATENT DOCUMENTS

| | | |
|---|---|---|
| 2002/0165461 A1 | 11/2002 | Hayzelden et al. |
| 2002/0171208 A1 | 11/2002 | Lechot et al. |
| 2002/0173813 A1 | 11/2002 | Peterson et al. |
| 2002/0183758 A1 | 12/2002 | Middleton et al. |
| 2002/0191823 A1 | 12/2002 | Wehrli et al. |
| 2003/0040805 A1 | 2/2003 | Minamikawa |
| 2003/0055373 A1 | 3/2003 | Sramek et al. |
| 2003/0055425 A1 | 3/2003 | Hajianpour |
| 2003/0069582 A1 | 4/2003 | Culbert |
| 2003/0069645 A1 | 4/2003 | Ball et al. |
| 2003/0074075 A1 | 4/2003 | Thomas, Jr. et al. |
| 2003/0083660 A1 | 5/2003 | Orbay |
| 2003/0083662 A1 | 5/2003 | Middleton |
| 2003/0093076 A1 | 5/2003 | Venturini et al. |
| 2003/0097132 A1 | 5/2003 | Padget et al. |
| 2003/0097133 A1 | 5/2003 | Green et al. |
| 2003/0105461 A1 | 6/2003 | Putnam |
| 2003/0109932 A1 | 6/2003 | Keynan |
| 2003/0120273 A1 | 6/2003 | Cole |
| 2003/0130660 A1 | 7/2003 | Levy et al. |
| 2003/0153918 A1 | 8/2003 | Putnam et al. |
| 2003/0187449 A1 | 10/2003 | McCleary et al. |
| 2003/0216738 A1 | 11/2003 | Azar |
| 2003/0220641 A1 | 11/2003 | Thelen et al. |
| 2003/0220644 A1 | 11/2003 | Thelen et al. |
| 2003/0220646 A1 | 11/2003 | Thelen et al. |
| 2003/0220698 A1 | 11/2003 | Mears et al. |
| 2003/0225407 A1 | 12/2003 | Estrada |
| 2004/0039384 A1 | 2/2004 | Boehm et al. |
| 2004/0044413 A1 | 3/2004 | Schulter |
| 2004/0049192 A1 | 3/2004 | Shimizu |
| 2004/0078082 A1 | 4/2004 | Lange |
| 2004/0087956 A1 | 5/2004 | Weikel et al. |
| 2004/0092946 A1 | 5/2004 | Bagga et al. |
| 2004/0102777 A1 | 5/2004 | Huebner |
| 2004/0102778 A1 | 5/2004 | Huebner et al. |
| 2004/0102788 A1 | 5/2004 | Huebner et al. |
| 2004/0106925 A1 | 6/2004 | Culbert |
| 2004/0138665 A1 | 7/2004 | Padget et al. |
| 2004/0143264 A1 | 7/2004 | McAfee |
| 2004/0153080 A1 | 8/2004 | Dong et al. |
| 2004/0153114 A1 | 8/2004 | Reiley et al. |
| 2004/0153115 A1 | 8/2004 | Reiley et al. |
| 2004/0167528 A1 | 8/2004 | Schantz |
| 2004/0167625 A1 | 8/2004 | Beyar et al. |
| 2004/0181221 A1 | 9/2004 | Huebner et al. |
| 2004/0193163 A1 | 9/2004 | Orbay |
| 2004/0193164 A1 | 9/2004 | Orbay |
| 2004/0193165 A1 | 9/2004 | Orbay |
| 2004/0193251 A1 | 9/2004 | Rudnick et al. |
| 2004/0193267 A1 | 9/2004 | Jones et al. |
| 2004/0208717 A1 | 10/2004 | Greenhalgh |
| 2004/0214311 A1 | 10/2004 | Levy |
| 2004/0220678 A1 | 11/2004 | Chow et al. |
| 2004/0230193 A1 | 11/2004 | Cheung et al. |
| 2004/0236327 A1 | 11/2004 | Paul et al. |
| 2004/0236328 A1 | 11/2004 | Paul et al. |
| 2004/0236339 A1 | 11/2004 | Pepper |
| 2004/0249375 A1 | 12/2004 | Agee et al. |
| 2004/0260289 A1 | 12/2004 | Padget et al. |
| 2004/0260297 A1 | 12/2004 | Padget et al. |
| 2004/0267269 A1 | 12/2004 | Middleton et al. |
| 2005/0010231 A1 | 1/2005 | Myers |
| 2005/0015129 A1 | 1/2005 | Mische |
| 2005/0015154 A1 | 1/2005 | Lindsey et al. |
| 2005/0033366 A1 | 2/2005 | Cole et al. |
| 2005/0043733 A1 | 2/2005 | Eisermann et al. |
| 2005/0065522 A1 | 3/2005 | Orbay |
| 2005/0065523 A1 | 3/2005 | Orbay |
| 2005/0065524 A1 | 3/2005 | Orbay |
| 2005/0065526 A1 | 3/2005 | Drew et al. |
| 2005/0070902 A1 | 3/2005 | Medoff |
| 2005/0085813 A1 | 4/2005 | Spitler et al. |
| 2005/0085818 A1 | 4/2005 | Huebner |
| 2005/0085824 A1 | 4/2005 | Castaneda |
| 2005/0085921 A1 | 4/2005 | Gupta et al. |
| 2005/0113836 A1 | 5/2005 | Lozier et al. |
| 2005/0113892 A1 | 5/2005 | Sproul |
| 2005/0119749 A1 | 6/2005 | Lange |
| 2005/0124972 A1 | 6/2005 | Mische et al. |
| 2005/0125066 A1 | 6/2005 | Mcafee |
| 2005/0131407 A1 | 6/2005 | Sicvol et al. |
| 2005/0142163 A1 | 6/2005 | Hunter et al. |
| 2005/0143734 A1 | 6/2005 | Cachia et al. |
| 2005/0154331 A1 | 7/2005 | Christie et al. |
| 2005/0159749 A1 | 7/2005 | Levy et al. |
| 2005/0177172 A1 | 8/2005 | Acker et al. |
| 2005/0182399 A1 | 8/2005 | Levine |
| 2005/0192578 A1 | 9/2005 | Horst |
| 2005/0197537 A1 | 9/2005 | Bonadio et al. |
| 2005/0209557 A1 | 9/2005 | Carroll et al. |
| 2005/0216000 A1 | 9/2005 | Colleran et al. |
| 2005/0216007 A1 | 9/2005 | Woll et al. |
| 2005/0216008 A1 | 9/2005 | Zwirnmann et al. |
| 2005/0228391 A1 | 10/2005 | Levy et al. |
| 2005/0234472 A1 | 10/2005 | Huebner |
| 2005/0240188 A1 | 10/2005 | Chow et al. |
| 2005/0240190 A1 | 10/2005 | Gall et al. |
| 2005/0240193 A1 | 10/2005 | Layne et al. |
| 2005/0245928 A1 | 11/2005 | Colleran et al. |
| 2005/0251142 A1 | 11/2005 | Hoffmann et al. |
| 2005/0261779 A1 | 11/2005 | Meyer |
| 2005/0267483 A1 | 12/2005 | Middleton |
| 2005/0273138 A1 | 12/2005 | To et al. |
| 2005/0277936 A1 | 12/2005 | Siravo et al. |
| 2005/0277978 A1 | 12/2005 | Greenhalgh |
| 2005/0283154 A1 | 12/2005 | Orbay et al. |
| 2005/0283159 A1 | 12/2005 | Amara |
| 2005/0288676 A1 | 12/2005 | Schnieders et al. |
| 2005/0288795 A1 | 12/2005 | Bagga et al. |
| 2006/0002980 A1 | 1/2006 | Ringeisen et al. |
| 2006/0004362 A1 | 1/2006 | Patterson et al. |
| 2006/0004462 A1 | 1/2006 | Gupta |
| 2006/0009771 A1 | 1/2006 | Orbay et al. |
| 2006/0015123 A1 | 1/2006 | Fencl et al. |
| 2006/0036240 A1 | 2/2006 | Colleran et al. |
| 2006/0036244 A1 | 2/2006 | Spitler et al. |
| 2006/0047787 A1 | 3/2006 | Agarwal et al. |
| 2006/0052788 A1 | 3/2006 | Thelen et al. |
| 2006/0058621 A1 | 3/2006 | Wehrli et al. |
| 2006/0058826 A1 | 3/2006 | Evans et al. |
| 2006/0064005 A1 | 3/2006 | Triano et al. |
| 2006/0064094 A1* | 3/2006 | Levy et al. ............ 606/63 |
| 2006/0064106 A1 | 3/2006 | Fernandez |
| 2006/0064164 A1 | 3/2006 | Thelen et al. |
| 2006/0064173 A1 | 3/2006 | Guederian et al. |
| 2006/0069392 A1 | 3/2006 | Renzi Brivio et al. |
| 2006/0079894 A1 | 4/2006 | Colleran et al. |
| 2006/0079905 A1 | 4/2006 | Beyar et al. |
| 2006/0085009 A1 | 4/2006 | Truckai et al. |
| 2006/0089647 A1 | 4/2006 | Culbert et al. |
| 2006/0089648 A1 | 4/2006 | Masini |
| 2006/0100631 A1 | 5/2006 | Sullivan et al. |
| 2006/0100706 A1 | 5/2006 | Shadduck et al. |
| 2006/0106390 A1 | 5/2006 | Jensen et al. |
| 2006/0106394 A1 | 5/2006 | Colleran |
| 2006/0116773 A1 | 6/2006 | Cooney et al. |
| 2006/0122600 A1 | 6/2006 | Cole |
| 2006/0122610 A1 | 6/2006 | Culbert et al. |
| 2006/0142760 A1* | 6/2006 | McDonnell ............ 606/61 |
| 2006/0142858 A1 | 6/2006 | Colleran et al. |
| 2006/0149281 A1 | 7/2006 | Reiley et al. |
| 2006/0149379 A1 | 7/2006 | Kuslich et al. |
| 2006/0155289 A1 | 7/2006 | Windhager et al. |
| 2006/0173454 A1 | 8/2006 | Spitler et al. |
| 2006/0178737 A1 | 8/2006 | Furcht et al. |
| 2006/0184192 A1 | 8/2006 | Markworth et al. |
| 2006/0187748 A1 | 8/2006 | Kozyuk |
| 2006/0189994 A1 | 8/2006 | Wolford et al. |
| 2006/0195103 A1 | 8/2006 | Padget et al. |
| 2006/0200061 A1 | 9/2006 | Warkentine |
| 2006/0200140 A1 | 9/2006 | Lange |
| 2006/0200143 A1 | 9/2006 | Warburton |
| 2006/0217730 A1 | 9/2006 | Termanini |

(56) References Cited

U.S. PATENT DOCUMENTS

| | | |
|---|---|---|
| 2006/0229602 A1 | 10/2006 | Olsen |
| 2006/0235264 A1 | 10/2006 | Vassallo |
| 2006/0241629 A1 | 10/2006 | Krebs et al. |
| 2006/0241630 A1 | 10/2006 | Brunnett et al. |
| 2006/0241671 A1 | 10/2006 | Greenhalgh |
| 2006/0241776 A1 | 10/2006 | Brown et al. |
| 2006/0247637 A1 | 11/2006 | Colleran et al. |
| 2006/0264944 A1 | 11/2006 | Cole |
| 2006/0264945 A1 | 11/2006 | Edidin et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0271053 A1 | 11/2006 | Schlapfer et al. |
| 2006/0271061 A1 | 11/2006 | Beyar et al. |
| 2006/0271198 A1 | 11/2006 | Mcafee |
| 2006/0276797 A1 | 12/2006 | Botimer |
| 2007/0012491 A1 | 1/2007 | Vasta |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016211 A1 | 1/2007 | Botimer |
| 2007/0016283 A1 | 1/2007 | Greenhalgh et al. |
| 2007/0016300 A1 | 1/2007 | Kuslich |
| 2007/0027230 A1 | 2/2007 | Beyar et al. |
| 2007/0032567 A1 | 2/2007 | Beyar et al. |
| 2007/0043373 A1 | 2/2007 | Sala et al. |
| 2007/0049936 A1 | 3/2007 | Colleran et al. |
| 2007/0055379 A1 | 3/2007 | Stone et al. |
| 2007/0066480 A1 | 3/2007 | Moser et al. |
| 2007/0073342 A1 | 3/2007 | Stone et al. |
| 2007/0100285 A1 | 5/2007 | Griffin et al. |
| 2007/0112427 A1 | 5/2007 | Christy et al. |
| 2007/0118132 A1 | 5/2007 | Culbert et al. |
| 2007/0123876 A1 | 5/2007 | Czartoski et al. |
| 2007/0123877 A1 | 5/2007 | Goldin et al. |
| 2007/0123886 A1 | 5/2007 | Meyer et al. |
| 2007/0123936 A1 | 5/2007 | Goldin et al. |
| 2007/0123995 A1 | 5/2007 | Thelen et al. |
| 2007/0129746 A1 | 6/2007 | Mische |
| 2007/0142919 A1 | 6/2007 | Cooney et al. |
| 2007/0173745 A1 | 7/2007 | Diederich et al. |
| 2007/0173835 A1 | 7/2007 | Medoff et al. |
| 2007/0173838 A1 | 7/2007 | Li |
| 2007/0173839 A1 | 7/2007 | Running et al. |
| 2007/0173939 A1 | 7/2007 | Kim et al. |
| 2007/0179505 A1 | 8/2007 | Culbert |
| 2007/0198043 A1 | 8/2007 | Cox et al. |
| 2007/0213727 A1 | 9/2007 | Bottlang et al. |
| 2007/0219634 A1 | 9/2007 | Greenhalgh et al. |
| 2007/0225568 A1 | 9/2007 | Colleran |
| 2007/0225721 A1 | 9/2007 | Thelen et al. |
| 2007/0225726 A1 | 9/2007 | Dye et al. |
| 2007/0225810 A1 | 9/2007 | Colleran et al. |
| 2007/0233091 A1 | 10/2007 | Naifeh et al. |
| 2007/0233105 A1 | 10/2007 | Nelson et al. |
| 2007/0244485 A1 | 10/2007 | Greenhalgh et al. |
| 2007/0255287 A1 | 11/2007 | Rabiner |
| 2007/0270855 A1 | 11/2007 | Partin et al. |
| 2007/0276392 A1 | 11/2007 | Beyar et al. |
| 2007/0276405 A1 | 11/2007 | Huebner et al. |
| 2007/0282443 A1 | 12/2007 | Globerman et al. |
| 2007/0283849 A1 | 12/2007 | Edidin et al. |
| 2007/0288097 A1 | 12/2007 | Hurowitz |
| 2008/0009874 A1 | 1/2008 | Meridew et al. |
| 2008/0009875 A1 | 1/2008 | Sankaran et al. |
| 2008/0012317 A1 | 1/2008 | Johnson |
| 2008/0015601 A1 | 1/2008 | Castro et al. |
| 2008/0019970 A1 | 1/2008 | Gorman |
| 2008/0021474 A1 | 1/2008 | Bonutti et al. |
| 2008/0039854 A1 | 2/2008 | Rabiner |
| 2008/0041629 A1 | 2/2008 | Aronstam et al. |
| 2008/0053575 A1 | 3/2008 | Cheung et al. |
| 2008/0058804 A1 | 3/2008 | Lechot et al. |
| 2008/0065072 A1 | 3/2008 | Spitler et al. |
| 2008/0065073 A1 | 3/2008 | Perriello et al. |
| 2008/0065074 A1 | 3/2008 | Yeung et al. |
| 2008/0065140 A1 | 3/2008 | Bonutti |
| 2008/0071356 A1 | 3/2008 | Greenhalgh et al. |
| 2008/0077117 A1 | 3/2008 | Miller et al. |
| 2008/0077172 A1 | 3/2008 | Miller et al. |
| 2008/0077174 A1 | 3/2008 | Mische |
| 2008/0086133 A1 | 4/2008 | Kuslich et al. |
| 2008/0097332 A1 | 4/2008 | Greenhalgh et al. |
| 2008/0103501 A1 | 5/2008 | Ralph et al. |
| 2008/0103519 A1 | 5/2008 | Bonutti |
| 2008/0108996 A1 | 5/2008 | Padget et al. |
| 2008/0114364 A1 | 5/2008 | Goldin et al. |
| 2008/0119886 A1 | 5/2008 | Greenhalgh et al. |
| 2008/0125784 A1 | 5/2008 | Rabiner et al. |
| 2008/0125805 A1 | 5/2008 | Mische |
| 2008/0132896 A1 | 6/2008 | Bowen et al. |
| 2008/0133017 A1 | 6/2008 | Beyar et al. |
| 2008/0140078 A1 | 6/2008 | Nelson et al. |
| 2008/0140130 A1 | 6/2008 | Chan et al. |
| 2008/0149115 A1 | 6/2008 | Hauck et al. |
| 2008/0161805 A1* | 7/2008 | Saravia .............. A61B 17/1725 606/60 |
| 2008/0161825 A1 | 7/2008 | Greenhalgh et al. |
| 2008/0167657 A1 | 7/2008 | Greenhalgh |
| 2008/0177261 A1 | 7/2008 | Mcminn |
| 2008/0183171 A1 | 7/2008 | Elghazaly et al. |
| 2008/0194868 A1 | 8/2008 | Kozyuk |
| 2008/0195104 A1 | 8/2008 | Sidebotham et al. |
| 2008/0195105 A1 | 8/2008 | Sidebotham et al. |
| 2008/0200915 A1 | 8/2008 | Globerman et al. |
| 2008/0200951 A1 | 8/2008 | Mcafee |
| 2008/0208202 A1 | 8/2008 | Williams |
| 2008/0208230 A1 | 8/2008 | Chin et al. |
| 2008/0208261 A1 | 8/2008 | Medoff |
| 2008/0208320 A1 | 8/2008 | Tan-Malecki et al. |
| 2008/0212405 A1 | 9/2008 | Globerman et al. |
| 2008/0228192 A1 | 9/2008 | Beyar et al. |
| 2008/0249436 A1 | 10/2008 | Darr |
| 2008/0255560 A1 | 10/2008 | Myers et al. |
| 2008/0262495 A1 | 10/2008 | Coati et al. |
| 2008/0269742 A1 | 10/2008 | Levy et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0275448 A1 | 11/2008 | Sackett et al. |
| 2008/0275449 A1 | 11/2008 | Sackett et al. |
| 2008/0287950 A1 | 11/2008 | Frigg et al. |
| 2008/0287951 A1 | 11/2008 | Stoneburner et al. |
| 2008/0294163 A1 | 11/2008 | Chou et al. |
| 2008/0294166 A1 | 11/2008 | Goldin et al. |
| 2008/0294167 A1 | 11/2008 | Schumacher et al. |
| 2008/0294169 A1 | 11/2008 | Scott et al. |
| 2008/0294205 A1 | 11/2008 | Greenhalgh et al. |
| 2008/0319444 A9 | 12/2008 | Osorio et al. |
| 2009/0005782 A1 | 1/2009 | Chirico et al. |
| 2009/0012522 A1 | 1/2009 | Lob |
| 2009/0012564 A1 | 1/2009 | Chirico et al. |
| 2009/0018542 A1* | 1/2009 | Saravia et al. .................. 606/63 |
| 2009/0018656 A1 | 1/2009 | Clifford et al. |
| 2009/0018666 A1 | 1/2009 | Grundei et al. |
| 2009/0024204 A1 | 1/2009 | Greenhalgh et al. |
| 2009/0048620 A1 | 2/2009 | Weiss et al. |
| 2009/0048629 A1 | 2/2009 | Rabiner |
| 2009/0054900 A1 | 2/2009 | Rabiner et al. |
| 2009/0076511 A1 | 3/2009 | Osman |
| 2009/0076517 A1 | 3/2009 | Reiley et al. |
| 2009/0088752 A1 | 4/2009 | Metzinger et al. |
| 2009/0104586 A1 | 4/2009 | Cardoso et al. |
| 2009/0112196 A1 | 4/2009 | Rabiner et al. |
| 2009/0112330 A1 | 4/2009 | Grundei |
| 2009/0125028 A1 | 5/2009 | Teisen et al. |
| 2009/0131992 A1 | 5/2009 | Greenhalgh et al. |
| 2009/0143781 A1 | 6/2009 | Mische |
| 2009/0143827 A1 | 6/2009 | Levy et al. |
| 2009/0149890 A1 | 6/2009 | Martin |

(56) References Cited

U.S. PATENT DOCUMENTS

| | | | |
|---|---|---|---|
| 2009/0149956 A1 | 6/2009 | Greenhalgh et al. | |
| 2009/0157080 A1 | 6/2009 | Warburton | |
| 2009/0163918 A1 | 6/2009 | Levy et al. | |
| 2009/0177206 A1 | 7/2009 | Lozier et al. | |
| 2009/0177239 A1 | 7/2009 | Castro | |
| 2009/0216232 A1 | 8/2009 | Buford et al. | |
| 2009/0228007 A1 | 9/2009 | Justin et al. | |
| 2009/0228008 A1* | 9/2009 | Justin et al. | 606/62 |
| 2009/0275995 A1 | 11/2009 | Truckai et al. | |
| 2009/0281628 A1 | 11/2009 | Oglaza | |
| 2009/0292323 A1 | 11/2009 | Chirico et al. | |
| 2009/0318981 A1 | 12/2009 | Kang | |
| 2010/0023010 A1* | 1/2010 | Nelson et al. | 606/62 |
| 2010/0087821 A1 | 4/2010 | Trip et al. | |
| 2010/0094292 A1 | 4/2010 | Parrott | |
| 2010/0094347 A1 | 4/2010 | Nelson et al. | |
| 2010/0100184 A1 | 4/2010 | Krueger et al. | |
| 2010/0114181 A1 | 5/2010 | Lob | |
| 2010/0131019 A1 | 5/2010 | Lob | |
| 2010/0137862 A1 | 6/2010 | Diao et al. | |
| 2010/0145397 A1 | 6/2010 | Overes et al. | |
| 2010/0161061 A1 | 6/2010 | Hunt | |
| 2010/0222884 A1 | 9/2010 | Greenhalgh | |
| 2010/0241120 A1 | 9/2010 | Bledsoe et al. | |
| 2010/0241123 A1 | 9/2010 | Middleton et al. | |
| 2010/0241176 A1 | 9/2010 | Lob | |
| 2010/0249785 A1 | 9/2010 | Betts | |
| 2010/0286481 A1 | 11/2010 | Sharp et al. | |
| 2011/0077650 A1 | 3/2011 | Braun et al. | |
| 2011/0087227 A1 | 4/2011 | Mazur et al. | |
| 2011/0137313 A1 | 6/2011 | Jensen et al. | |
| 2011/0144645 A1 | 6/2011 | Saravia et al. | |
| 2011/0178520 A1 | 7/2011 | Taylor et al. | |
| 2011/0190832 A1 | 8/2011 | Taylor et al. | |
| 2011/0218585 A1 | 9/2011 | Krinke et al. | |
| 2011/0218626 A1 | 9/2011 | Krinke et al. | |
| 2011/0282346 A1 | 11/2011 | Pham et al. | |
| 2011/0295255 A1 | 12/2011 | Roberts et al. | |
| 2011/0307021 A1 | 12/2011 | Anderson et al. | |
| 2011/0307072 A1 | 12/2011 | Anderson et al. | |
| 2011/0313537 A1 | 12/2011 | Anderson et al. | |
| 2012/0029633 A1 | 2/2012 | Anderson et al. | |
| 2012/0065638 A1 | 3/2012 | Moore | |
| 2012/0152872 A1 | 6/2012 | Didehvar | |
| 2012/0179161 A1 | 7/2012 | Rains et al. | |
| 2012/0209265 A1 | 8/2012 | Pool | |
| 2012/0209273 A1 | 8/2012 | Zaretzka et al. | |
| 2012/0232533 A1 | 9/2012 | Veldman et al. | |
| 2012/0239038 A1 | 9/2012 | Saravia et al. | |
| 2012/0253410 A1 | 10/2012 | Taylor et al. | |
| 2013/0006245 A1 | 1/2013 | Stoneburner et al. | |
| 2013/0012942 A1 | 1/2013 | Nelson et al. | |
| 2013/0116693 A1 | 5/2013 | Nelson et al. | |
| 2013/0231665 A1 | 9/2013 | Saravia et al. | |
| 2013/0267953 A1 | 10/2013 | Brenzel et al. | |
| 2014/0031823 A1 | 1/2014 | Mazur et al. | |
| 2014/0074093 A9 | 3/2014 | Nelson et al. | |
| 2014/0088707 A1 | 3/2014 | Donner et al. | |
| 2014/0128870 A1 | 5/2014 | Brenzel et al. | |
| 2014/0200618 A1 | 7/2014 | Donner et al. | |
| 2015/0012096 A1 | 1/2015 | Krinke et al. | |
| 2015/0141996 A1 | 5/2015 | Taylor et al. | |
| 2015/0164514 A1 | 6/2015 | Wlodarski et al. | |
| 2015/0320459 A1 | 11/2015 | Brenzel et al. | |

FOREIGN PATENT DOCUMENTS

| | | |
|---|---|---|
| CA | 2609175 A1 | 12/2005 |
| CA | 2608693 A1 | 11/2006 |
| CA | 2537171 C | 8/2007 |
| CA | 2669737 A1 | 5/2008 |
| CA | 2670263 A1 | 5/2008 |
| CA | 2670438 A1 | 5/2008 |
| CA | 2678911 A1 | 9/2008 |
| CA | 2685046 A1 | 11/2008 |
| CA | 2727453 A1 | 12/2009 |
| CA | 2738478 A1 | 4/2010 |
| CN | 2326199 | 6/1999 |
| CN | 1530079 | 9/2004 |
| CN | 1533260 A | 9/2004 |
| CN | 2699849 Y | 5/2005 |
| CN | 1909848 A | 2/2007 |
| CN | 100379388 | 4/2008 |
| CN | 101208053 A | 6/2008 |
| CN | 101636119 A | 1/2010 |
| DE | 923085 | 7/1949 |
| DE | 3146065 A1 | 5/1983 |
| DE | 3234875 A1 | 3/1984 |
| DE | 198800197 U1 | 8/1988 |
| DE | 3922044 A1 | 2/1991 |
| DE | 4214236 | 11/1993 |
| DE | 202006017194 U1 | 2/2007 |
| DE | 102006016213 | 10/2007 |
| EP | 145166 A2 | 6/1985 |
| EP | 0145166 A2 | 6/1985 |
| EP | 145166 A3 | 8/1986 |
| EP | 253526 A1 | 1/1988 |
| EP | 263292 A1 | 4/1988 |
| EP | 275871 A1 | 7/1988 |
| EP | 355035 A2 | 2/1990 |
| EP | 381462 A2 | 8/1990 |
| EP | 396519 A1 | 11/1990 |
| EP | 401650 A1 | 12/1990 |
| EP | 409769 A1 | 1/1991 |
| EP | 420542 A1 | 4/1991 |
| EP | 440371 A1 | 8/1991 |
| EP | 442137 A1 | 8/1991 |
| EP | 475077 A2 | 3/1992 |
| EP | 487669 A1 | 6/1992 |
| EP | 491211 A1 | 6/1992 |
| EP | 508710 A1 | 10/1992 |
| EP | 525352 A1 | 2/1993 |
| EP | 611560 A1 | 8/1994 |
| EP | 745352 A2 | 12/1996 |
| EP | 546162 B1 | 9/1997 |
| EP | 807419 A2 | 11/1997 |
| EP | 819413 A2 | 1/1998 |
| EP | 931513 A2 | 7/1999 |
| EP | 0941037 B1 | 9/1999 |
| EP | 1099412 A2 | 5/2001 |
| EP | 1132051 A2 | 9/2001 |
| EP | 674495 B1 | 11/2001 |
| EP | 1155661 A1 | 11/2001 |
| EP | 1203569 A1 | 5/2002 |
| EP | 900065 B1 | 6/2002 |
| EP | 1277442 A2 | 1/2003 |
| EP | 1300122 A2 | 4/2003 |
| EP | 1348384 A2 | 10/2003 |
| EP | 1354562 | 10/2003 |
| EP | 1372496 A1 | 1/2004 |
| EP | 1391186 A1 | 2/2004 |
| EP | 1098600 B1 | 3/2004 |
| EP | 1277442 A3 | 3/2004 |
| EP | 1396231 A1 | 3/2004 |
| EP | 1410765 A2 | 4/2004 |
| EP | 1442718 A1 | 8/2004 |
| EP | 1442729 A1 | 8/2004 |
| EP | 1454592 A2 | 9/2004 |
| EP | 1459686 A2 | 9/2004 |
| EP | 1484077 A2 | 12/2004 |
| EP | 1079752 B1 | 1/2005 |
| EP | 1484077 A3 | 1/2005 |
| EP | 1495729 A1 | 1/2005 |
| EP | 1148825 B1 | 3/2005 |
| EP | 1148850 B1 | 4/2005 |
| EP | 1522268 A1 | 4/2005 |
| EP | 1227765 B1 | 5/2005 |
| EP | 1535579 A2 | 6/2005 |
| EP | 1563795 A1 | 8/2005 |
| EP | 1582159 A1 | 10/2005 |
| EP | 1582160 A1 | 10/2005 |
| EP | 1582161 A1 | 10/2005 |
| EP | 1582162 A1 | 10/2005 |
| EP | 1582163 A1 | 10/2005 |

(56) References Cited

FOREIGN PATENT DOCUMENTS

| | | | |
|---|---|---|---|
| EP | 1582164 A1 | 10/2005 |
| EP | 1634548 A2 | 3/2006 |
| EP | 1639953 A1 | 3/2006 |
| EP | 1669035 A1 | 6/2006 |
| EP | 1073371 B1 | 8/2006 |
| EP | 1454592 A3 | 8/2006 |
| EP | 1700572 A1 | 9/2006 |
| EP | 1702572 A2 | 9/2006 |
| EP | 1714618 A2 | 10/2006 |
| EP | 1787593 A1 | 5/2007 |
| EP | 1808143 A1 | 7/2007 |
| EP | 1815813 A2 | 8/2007 |
| EP | 1820462 A1 | 8/2007 |
| EP | 1011464 B1 | 1/2008 |
| EP | 1905367 A1 | 4/2008 |
| EP | 1905392 A1 | 4/2008 |
| EP | 1915959 A2 | 4/2008 |
| EP | 1920721 A2 | 5/2008 |
| EP | 1923019 A1 | 5/2008 |
| EP | 1277442 B1 | 7/2008 |
| EP | 1972308 A1 | 9/2008 |
| EP | 1987785 A2 | 11/2008 |
| EP | 2014261 A1 | 1/2009 |
| EP | 2025292 A1 | 2/2009 |
| EP | 1459689 B1 | 4/2009 |
| EP | 1484077 B1 | 6/2009 |
| EP | 1073371 B2 | 7/2009 |
| EP | 1459689 B3 | 11/2009 |
| ES | 2251888 | 5/2006 |
| FR | 2653006 A1 | 4/1991 |
| FR | 2686788 | 8/1993 |
| FR | 2781360 | 1/2000 |
| GB | 2173565 A | 10/1986 |
| GB | 2268068 A | 1/1994 |
| GB | 2274993 | 8/1994 |
| JP | 1310664 A | 12/1989 |
| JP | 2000287983 | 10/2000 |
| JP | 2007125386 | 5/2007 |
| JP | 2008500140 A | 1/2008 |
| JP | 2008540037 A | 11/2008 |
| JP | 2010510040 A | 4/2010 |
| JP | 2010510041 A | 4/2010 |
| JP | 2010510042 A | 4/2010 |
| JP | 2010522046 A | 7/2010 |
| JP | 2010524642 A | 7/2010 |
| JP | 2011523889 A | 8/2011 |
| JP | 2012504027 A | 2/2012 |
| RU | 2004104359 A | 2/2005 |
| WO | WO8904150 A1 | 5/1989 |
| WO | WO8907056 A1 | 8/1989 |
| WO | WO9003764 A1 | 4/1990 |
| WO | WO9011726 A1 | 10/1990 |
| WO | WO9102493 A1 | 3/1991 |
| WO | WO9106260 A1 | 5/1991 |
| WO | WO9106265 A1 | 5/1991 |
| WO | WO9111962 A1 | 8/1991 |
| WO | WO9119461 A1 | 12/1991 |
| WO | WO9424938 A1 | 11/1994 |
| WO | WO9427507 A1 | 12/1994 |
| WO | WO9428824 A2 | 12/1994 |
| WO | WO9514433 A1 | 6/1995 |
| WO | WO9514433 A1 | 6/1995 |
| WO | WO9520362 A1 | 8/1995 |
| WO | WO9531159 A1 | 11/1995 |
| WO | WO9602202 A1 | 2/1996 |
| WO | WO9602203 A1 | 2/1996 |
| WO | WO9605783 A1 | 2/1996 |
| WO | WO9606041 A1 | 2/1996 |
| WO | WO9607161 A1 | 3/1996 |
| WO | WO9616607 A1 | 6/1996 |
| WO | WO9617557 A1 | 6/1996 |
| WO | WO9618354 A2 | 6/1996 |
| WO | WO9618354 A2 | 6/1996 |
| WO | WO9618354 A3 | 8/1996 |
| WO | WO9625118 A1 | 8/1996 |
| WO | WO9640476 A1 | 12/1996 |
| WO | WO9703611 A1 | 2/1997 |
| WO | WO9703611 A1 | 2/1997 |
| WO | WO9718775 A1 | 5/1997 |
| WO | WO9742602 A1 | 11/1997 |
| WO | WO9742912 A1 | 11/1997 |
| WO | WO9747251 A1 | 12/1997 |
| WO | WO9801077 A1 | 1/1998 |
| WO | WO9805261 A2 | 2/1998 |
| WO | WO9807392 A1 | 2/1998 |
| WO | WO9819616 A1 | 5/1998 |
| WO | WO9824380 A1 | 6/1998 |
| WO | WO9826725 A1 | 6/1998 |
| WO | WO9838918 A1 | 9/1998 |
| WO | WO9846169 A1 | 10/1998 |
| WO | WO9856301 A1 | 12/1998 |
| WO | WO9922661 A1 | 5/1999 |
| WO | WO9922662 A1 | 5/1999 |
| WO | WO9937219 A1 | 7/1999 |
| WO | WO9947055 A1 | 9/1999 |
| WO | WO9951149 A1 | 10/1999 |
| WO | WO9953843 A1 | 10/1999 |
| WO | WO9955248 A1 | 11/1999 |
| WO | WO9962416 A1 | 12/1999 |
| WO | WO0006037 A1 | 2/2000 |
| WO | WO0009024 A1 | 2/2000 |
| WO | WO0012036 A1 | 3/2000 |
| WO | WO0012036 A1 | 3/2000 |
| WO | WO0021455 A1 | 4/2000 |
| WO | WO0025681 A1 | 5/2000 |
| WO | WO0028906 A1 | 5/2000 |
| WO | WO0030551 A1 | 6/2000 |
| WO | WO0030569 A1 | 6/2000 |
| WO | WO0038586 A1 | 7/2000 |
| WO | WO0042954 A2 | 7/2000 |
| WO | WO0044319 A1 | 8/2000 |
| WO | WO0044321 A2 | 8/2000 |
| WO | WO0044946 A1 | 8/2000 |
| WO | WO0045712 A1 | 8/2000 |
| WO | WO0045714 A1 | 8/2000 |
| WO | WO0045715 A1 | 8/2000 |
| WO | WO0045722 A1 | 8/2000 |
| WO | WO0047119 A1 | 8/2000 |
| WO | WO0048534 A1 | 8/2000 |
| WO | WO0071038 A1 | 11/2000 |
| WO | WO0076414 A1 | 12/2000 |
| WO | WO0108571 A1 | 2/2001 |
| WO | WO0128443 A1 | 4/2001 |
| WO | WO0134045 A1 | 5/2001 |
| WO | WO0149193 A1 | 7/2001 |
| WO | WO0154598 A1 | 8/2001 |
| WO | WO0160268 A1 | 8/2001 |
| WO | WO0160268 A1 | 8/2001 |
| WO | WO0176493 A1 | 10/2001 |
| WO | WO0176514 A2 | 10/2001 |
| WO | WO0178015 A2 | 10/2001 |
| WO | WO0180751 A1 | 11/2001 |
| WO | WO0185042 A1 | 11/2001 |
| WO | WO0213700 A2 | 2/2002 |
| WO | WO0213716 A1 | 2/2002 |
| WO | WO0217794 A1 | 3/2002 |
| WO | WO0217794 A1 | 3/2002 |
| WO | WO0224088 A2 | 3/2002 |
| WO | WO0234107 A2 | 5/2002 |
| WO | WO0234148 A2 | 5/2002 |
| WO | WO0237935 A2 | 5/2002 |
| WO | WO0245606 A1 | 6/2002 |
| WO | WO0249517 A1 | 6/2002 |
| WO | WO02058575 A1 | 8/2002 |
| WO | WO02067824 A2 | 9/2002 |
| WO | WO02078555 A1 | 10/2002 |
| WO | WO02089683 A1 | 11/2002 |
| WO | WO02096306 A1 | 12/2002 |
| WO | WO03007830 A1 | 1/2003 |
| WO | WO03013336 A2 | 2/2003 |
| WO | WO02017794 A8 | 3/2003 |
| WO | WO03030760 A1 | 4/2003 |
| WO | WO03043488 A2 | 5/2003 |
| WO | WO03045257 A2 | 6/2003 |

(56) References Cited

FOREIGN PATENT DOCUMENTS

| | | |
|---|---|---|
| WO | WO03047440 A2 | 6/2003 |
| WO | WO03068090 A1 | 8/2003 |
| WO | WO02017794 A9 | 9/2003 |
| WO | WO2004008949 A2 | 1/2004 |
| WO | WO2004017817 A2 | 3/2004 |
| WO | WO2004021904 | 3/2004 |
| WO | WO2004030549 A1 | 4/2004 |
| WO | WO2004039271 | 5/2004 |
| WO | WO2004064603 A2 | 8/2004 |
| WO | WO2004078220 A2 | 9/2004 |
| WO | WO2004078221 A2 | 9/2004 |
| WO | WO2004086934 A2 | 10/2004 |
| WO | WO2004092431 A1 | 10/2004 |
| WO | WO2004093633 A2 | 11/2004 |
| WO | WO2004098453 A2 | 11/2004 |
| WO | WO2004103209 A2 | 12/2004 |
| WO | WO2004110292 A2 | 12/2004 |
| WO | WO2004110300 A2 | 12/2004 |
| WO | WO2004112661 A1 | 12/2004 |
| WO | WO2005000159 A2 | 1/2005 |
| WO | WO2005020830 A1 | 3/2005 |
| WO | WO2005020833 A2 | 3/2005 |
| WO | WO2005023085 A2 | 3/2005 |
| WO | WO2005032326 A2 | 4/2005 |
| WO | WO2005032340 A2 | 4/2005 |
| WO | WO2005039651 A2 | 5/2005 |
| WO | WO2005041799 A1 | 5/2005 |
| WO | WO2005044122 A1 | 5/2005 |
| WO | WO2005051971 A1 | 6/2005 |
| WO | WO2005055874 A2 | 6/2005 |
| WO | WO2005020833 A3 | 7/2005 |
| WO | WO2005070314 A1 | 8/2005 |
| WO | WO2005092223 A2 | 10/2005 |
| WO | WO2005094693 A1 | 10/2005 |
| WO | WO2005094705 A2 | 10/2005 |
| WO | WO2005094706 A1 | 10/2005 |
| WO | WO2005096975 A2 | 10/2005 |
| WO | WO2005102196 A1 | 11/2005 |
| WO | WO2005107415 A2 | 11/2005 |
| WO | WO2005112804 A1 | 12/2005 |
| WO | WO2005112804 A1 | 12/2005 |
| WO | WO2005122931 A1 | 12/2005 |
| WO | WO2005122932 A2 | 12/2005 |
| WO | WO2005123171 A2 | 12/2005 |
| WO | WO2006011152 A2 | 2/2006 |
| WO | WO2006020530 A2 | 2/2006 |
| WO | WO2005112804 A9 | 3/2006 |
| WO | WO2006023793 A2 | 3/2006 |
| WO | WO2006026323 A2 | 3/2006 |
| WO | WO2006026323 A2 | 3/2006 |
| WO | WO2006026323 A9 | 4/2006 |
| WO | WO2006041460 A1 | 4/2006 |
| WO | WO2006041460 A1 | 4/2006 |
| WO | WO2006042188 A2 | 4/2006 |
| WO | WO2006042189 A2 | 4/2006 |
| WO | WO2006042334 A2 | 4/2006 |
| WO | WO2006034396 A3 | 5/2006 |
| WO | WO2006051547 A2 | 5/2006 |
| WO | WO2006055448 A1 | 5/2006 |
| WO | WO2006063083 A1 | 6/2006 |
| WO | WO2006066228 A2 | 6/2006 |
| WO | WO2006068682 A1 | 6/2006 |
| WO | WO2006089929 A1 | 8/2006 |
| WO | WO2006090379 A2 | 8/2006 |
| WO | WO2006034436 A3 | 10/2006 |
| WO | WO2006108067 A2 | 10/2006 |
| WO | WO2006113800 A2 | 10/2006 |
| WO | WO2006116760 A2 | 11/2006 |
| WO | WO2006116761 A2 | 11/2006 |
| WO | WO2006124764 A1 | 11/2006 |
| WO | WO2006124764 A1 | 11/2006 |
| WO | WO2006124937 A2 | 11/2006 |
| WO | WO2006127904 A1 | 11/2006 |
| WO | WO2006127904 A1 | 11/2006 |
| WO | WO2007002933 A2 | 1/2007 |
| WO | WO2007008177 A1 | 1/2007 |
| WO | WO2007009107 A2 | 1/2007 |
| WO | WO2007009123 A2 | 1/2007 |
| WO | WO2007011994 A2 | 1/2007 |
| WO | WO2007012046 A2 | 1/2007 |
| WO | WO2007025236 A2 | 3/2007 |
| WO | WO2007040949 A2 | 4/2007 |
| WO | WO2007041665 A2 | 4/2007 |
| WO | WO2006124937 A3 | 5/2007 |
| WO | WO2007053960 A1 | 5/2007 |
| WO | WO2007058943 A2 | 5/2007 |
| WO | WO2007059243 A1 | 5/2007 |
| WO | WO2007059243 A1 | 5/2007 |
| WO | WO2007059246 A1 | 5/2007 |
| WO | WO2007059259 A1 | 5/2007 |
| WO | WO2007059259 A1 | 5/2007 |
| WO | WO2007065137 A2 | 6/2007 |
| WO | WO2007069251 A2 | 6/2007 |
| WO | WO2007073488 A2 | 6/2007 |
| WO | WO2007076308 A2 | 7/2007 |
| WO | WO2007076374 A2 | 7/2007 |
| WO | WO2007076376 A2 | 7/2007 |
| WO | WO2007076377 A2 | 7/2007 |
| WO | WO2007078692 A2 | 7/2007 |
| WO | WO2007079237 A2 | 7/2007 |
| WO | WO2007082151 A2 | 7/2007 |
| WO | WO2007084239 A2 | 7/2007 |
| WO | WO2007092813 A2 | 8/2007 |
| WO | WO2007092813 A2 | 8/2007 |
| WO | WO2007092841 A2 | 8/2007 |
| WO | WO2007092841 A2 | 8/2007 |
| WO | WO2007036815 A2 | 9/2007 |
| WO | WO2007114982 A1 | 10/2007 |
| WO | WO2007115108 A1 | 10/2007 |
| WO | WO2007117571 A2 | 10/2007 |
| WO | WO2007120539 A2 | 10/2007 |
| WO | WO2007092841 A3 | 11/2007 |
| WO | WO2007124130 A2 | 11/2007 |
| WO | WO2007127255 A2 | 11/2007 |
| WO | WO2007127260 A2 | 11/2007 |
| WO | WO2007131002 A2 | 11/2007 |
| WO | WO2007134134 A2 | 11/2007 |
| WO | WO2007079237 A3 | 12/2007 |
| WO | WO2007145824 A2 | 12/2007 |
| WO | WO2008004229 A2 | 1/2008 |
| WO | WO2008006117 A2 | 1/2008 |
| WO | WO2008016910 A2 | 2/2008 |
| WO | WO2008019397 A2 | 2/2008 |
| WO | WO2008035849 A1 | 3/2008 |
| WO | WO2008037454 A1 | 4/2008 |
| WO | WO2008043254 A1 | 4/2008 |
| WO | WO2008058960 A2 | 5/2008 |
| WO | WO2008059027 A2 | 5/2008 |
| WO | WO2008060277 A2 | 5/2008 |
| WO | WO2008060277 A2 | 5/2008 |
| WO | WO2008063265 A1 | 5/2008 |
| WO | WO2008064346 A2 | 5/2008 |
| WO | WO2008064347 A2 | 5/2008 |
| WO | WO2008064347 A2 | 5/2008 |
| WO | WO2008064350 A2 | 5/2008 |
| WO | WO2008076330 A1 | 6/2008 |
| WO | WO2008076330 A1 | 6/2008 |
| WO | WO2008076357 A1 | 6/2008 |
| WO | WO2008094407 A1 | 8/2008 |
| WO | WO2007011353 A3 | 9/2008 |
| WO | WO2007092813 A3 | 9/2008 |
| WO | WO2008109566 A1 | 9/2008 |
| WO | WO2008112308 A1 | 9/2008 |
| WO | WO2008116170 A2 | 9/2008 |
| WO | WO2008116175 A2 | 9/2008 |
| WO | WO2008118945 A1 | 10/2008 |
| WO | WO2008121608 A2 | 10/2008 |
| WO | WO2008132728 A1 | 11/2008 |
| WO | WO2008134287 A2 | 11/2008 |
| WO | WO2008134758 A1 | 11/2008 |
| WO | WO2008139456 A2 | 11/2008 |
| WO | WO2008144709 A2 | 11/2008 |
| WO | WO2008144709 A2 | 11/2008 |
| WO | WO2007078692 A3 | 12/2008 |

(56) References Cited

FOREIGN PATENT DOCUMENTS

| | | |
|---|---|---|
| WO | WO2008121608 A3 | 1/2009 |
| WO | WO2008134287 A3 | 1/2009 |
| WO | WO2009006622 A2 | 1/2009 |
| WO | WO2009007331 A2 | 1/2009 |
| WO | WO2009009772 A1 | 1/2009 |
| WO | WO2009010412 A1 | 1/2009 |
| WO | WO2009012347 A1 | 1/2009 |
| WO | WO2009026070 A1 | 2/2009 |
| WO | WO2009027325 A1 | 3/2009 |
| WO | WO2009039430 A1 | 3/2009 |
| WO | WO2006026323 A3 | 4/2009 |
| WO | WO2006026397 A3 | 4/2009 |
| WO | WO2009045751 A1 | 4/2009 |
| WO | WO2009059227 A1 | 5/2009 |
| WO | WO2009067568 | 5/2009 |
| WO | WO2009072125 A1 | 6/2009 |
| WO | WO2009076086 A1 | 6/2009 |
| WO | WO2008144709 A3 | 7/2009 |
| WO | WO2009088376 A1 | 7/2009 |
| WO | WO2009094478 A1 | 7/2009 |
| WO | WO2008060277 A3 | 9/2009 |
| WO | WO2008112912 A3 | 9/2009 |
| WO | WO2009132333 A2 | 10/2009 |
| WO | WO2009143374 A2 | 11/2009 |
| WO | WO2009143496 A1 | 11/2009 |
| WO | WO2008112875 A3 | 12/2009 |
| WO | WO2009146457 A1 | 12/2009 |
| WO | WO2009152270 A1 | 12/2009 |
| WO | WO2009152272 A1 | 12/2009 |
| WO | WO2009152273 A1 | 12/2009 |
| WO | WO2009132333 A3 | 1/2010 |
| WO | WO2008139456 A3 | 2/2010 |
| WO | WO2010037038 A2 | 4/2010 |
| WO | WO2010056895 A1 | 5/2010 |
| WO | WO2010062379 A1 | 6/2010 |
| WO | WO2010065855 A1 | 6/2010 |
| WO | WO2010091242 A1 | 8/2010 |
| WO | WO2010035156 A1 | 11/2010 |

OTHER PUBLICATIONS

US 7,201,752, 04/2007, Huebner et al. (withdrawn)
Appl'n No. PCT/US/2009/30971 International Search Report, Mar. 6, 2009.
Appl'n No. PCT/US/2009/30971 Written Opinion of the International Searching Authority, Mar. 6, 2009.
Appl'n No. PCT/US/2011/21074 International Search Report, May 23, 2011.
Appl'n No. PCT/US/2011/21074 Written Opinion of the International Searching Authority, May 23, 2011.
Appl'n No. PCT/US/2011/021735 International Search Report, May 25, 2011.
Appl'n No. PCT/US/2011/021735 Written Opinion of the International Searching Authority, May 25, 2011.
Appl'n No. PCT/US/2011/027597 International Search Report, Jul. 6, 2011.
Appl'n No. PCT/US/2011/027597 Written Opinion of the International Searching Authority, Jul. 6, 2011.
Appl'n No. PCT/US/2011/027602 International Search Report, Jul. 5, 2011.
Appl'n No. PCT/US/2011/027602 Written Opinion of the International Searching Authority, Jul. 5, 2011.
Appl'n No. PCT/US/2012/028145 International Search Report, Sep. 13, 2012.
Appl'n No. PCT/US/2012/028145 Written Opinion of the International Searching Authority, Sep. 13, 2012.
App No. PCT/US 09/30971 International Search Report.
App No. PCT/US 09/30971 Written Opinion of the International Searching Authority.
App No. PCT/US2011/21074 International Search Report.
App No. PCT/US2011/21074 Written Opinion of the International Searching Authority.
App No. PCT/US2011/021735 International Search Report.
App No. PCT/US2011/021735 Written Opinion of the International Searching Authority.
App No. PCT/US2011/027597 International Search Report.
App No. PCT/US2011/027597 Written Opinion of the International Searching Authority.
App No. PCT/US2011/027602 International Search Report.
App No. PCT/US2011/027602 Written Opinion of the International Searching Authority.
Putnam, Matthew D., et al., "Distal Radial Metaphyseal Forces in an Extrinsic Grip Model: Implications for Post fracture Rehabilitation," American Society for Surgery of the Hand, 25A: 469-475, May 2000.
Higgins, Thomas F., et al., "A Biomechanical Analysis of Fixation of Intra-Articular Distal Radial Fractures with Calcium-Phosphate Bone Cement," The Journal of Bone and Joint Surgery, 84:1579-1586, Needham, Massachusetts, Sep. 2002.
Stoeckel et al., "Self-Expanding Nitinol Stents—Material and Design Considerations," Nitinol Devices & Components, Fremont, California, 2003.
Rozenthal, Tamara D., et al., "Functional Outcome and Complications After Volar Plating for Dorsally Displaced, Unstable Fractures of the Distal Radius," The Journal of Hand Surgery, 31A: 359-365, Mar. 2006.
Keast-Butler, Oliver, et al., "Biology Versus Mechanics in the Treatment of Distal Radial Fractures," The Journal of Orthopedic Trauma, 22: S91-S95, Philadelphia, Pennsylvania, Sep. 2008.
Mudgal, Chaitanya S., et al., "Plate Fixation of Osteoporotic Fractures of the Distal Radius," The Journal of Orthopedic Trauma, 22: S106-S115, 2008, Philadelphia, Pennsylvania, Sep. 2008.
Bogoch, Earl R., et al., "The Osteoporosis Needs of Patients with Wrist Fractures," The Journal of Orthopedic Trauma, vol. 22, No. 8, Supplement, Philadelphia, Pennsylvania, Sep. 2008.
Arora, Rohit, et al., "A Representative Case of Osteoporotic Distal Radius Fracture," The Journal of Orthopedic Trauma, vol. 22, No. 8, Supplement, Philadelphia, Pennsylvania, Sep. 2008.
Firoozabadi, Reza, et al., "Qualitative and Quantitative Assessment of Bone Fragility and Fracture Healing Using Conventional Radiography and Advanced Imaging Technologies—Focus on Wrist Fracture," The Journal of Orthopedic Trauma, vol. 22, No. 8, Supplement, Philadelphia, Pennsylvania, Sep. 2008.
Goldhan, Jorg, et al., "What Counts: Outcome Assessment After Distal Radius Fractures in Aged Patients," The Journal of Orthopedic Trauma, vol. 22, No. 8, Supplement, Philadelphia, Pennsylvania, Sep. 2008.
Hoang-Kim, Amy, et al., "Wrist Fractures in Osteoporotic Patients," The Journal of Orthopedic Trauma, vol. 22, No. 8, Supplement, Philadelphia, Pennsylvania, Sep. 2008.
Kettler, Mark, et al., "Do We Need to Include Osteoporosis in Today's Classification of Distal Radius Fractures?" The Journal of Orthopedic Trauma, vol. 22, No. 8, Supplement, Philadelphia, Pennsylvania, Sep. 2008.
Downing, Martin R., et al., "Assessment of Inducible Fracture Micromotion in Distal Radial Fractures Using Radiostereometry," The Journal of Orthopedic Trauma, vol. 22, No. 8, Supplement, Philadelphia, Pennsylvania, Sep. 2008.
Suhm, Norbert, et al., "Injectable Bone Cement Augmentation for the Treatment of Distal Radius Fractures: A Review," The Journal of Orthopedic Trauma, vol. 22, No. 8, Supplement, Philadelphia, Pennsylvania, Sep. 2008.
Van Lenthe, G. Harry, et al., "Quantification of Bone Structural Parameters and Mechanical Competence at the Distal Radius," The Journal of Orthopedic Trauma, vol. 22, No. 8, Supplement, Philadelphia, Pennsylvania, Sep. 2008.
Parkinson, Ian H., et al., "Whole Bone Geometry and Bone Quality in Distal Forearm Fracture," The Journal of Orthopedic Trauma, vol. 22, No. 8, Supplement, Philadelphia, Pennsylvania, Sep. 2008.
"Medtronic—Abdominal Stent Graft System, Instructions for Use," Medtronic, Inc., Minneapolis—Minnesota, 2008.
Jupiter, Jesse B., et al., "Operative Management of Distal Radial Fractures with 2.4-Millimeter Locking Plates. A Multicenter Prospective Case Series," The Journal of Bone and Joint Surgery, 91: 55-65, doi:10.2106-JBJS.G.01498, Needham, Massachusetts, Jan. 1, 2009.
App No. PCT/US2012/028145 International Search Report.
App No. PCT/US2012/028145 Written Opinion of the International Searching Authority.

(56) References Cited

OTHER PUBLICATIONS

Ilyas, Asif M., "Intramedullary Fixation of Distal Radius Fractures," Elsevier, Inc. on behalf of the American Society for Surgery of the Hand, New York, New York, Feb. 2009.
Figl, Markus, et al., "Volar Fixed-Angle Plate Osteosynthesis of Unstable Distal Radius Fractures: 12 Months Results," Springer, New York, New York, Feb. 19, 2009.
Photograph, OrthopaedicLIST, 2010, Wilmington, North Carolina.
Barnes, C. Lowry, et al., "Advanced Core Decompression System," Wright, 2008, Arlington, Tennessee.
"OptiMesh 1500E—Percutaneous Interbody Fusion Surgical Technique," Spineology Inc., Feb. 2010, Saint Paul, Minnesota.
Corti, G., et al., "Acute Vertebral Body Compression Fracture treated with OptiMesh—Indications, Applications and First Clinical Results," Eurospine, 2005, Uster-Zürich Switzerland.
Advanced Core Decompression System—Surgical Technique, Wright, 2010, Arlington, Tennessee.
International Search Report for International Application No. PCT/US14/69907, Jun. 4, 2015.
Written Opinion for International Application No. PCT/US14/69907, Jun. 4, 2015.
Taylor et al., U.S. Appl. No. 15/420,422, dated Jan. 31, 2017.
Peterson et al., U.S. Appl. No. 15/399,369, dated Jan. 5, 2017.
European Patent Office Entended Search Report in application No. 11753948.6, dated Jan. 25, 2017.

* cited by examiner

ROTARY-RIGID ORTHOPAEDIC ROD

CROSS-REFERENCE TO RELATED APPLICATIONS

This application is a continuation of U.S. patent application Ser. No. 13/005,654, filed on Jan. 13, 2011, which is a nonprovisional of U.S. Provisional Application No. 61/295,244, filed on Jan. 15, 2010, both of which are hereby incorporated by reference herein in their entireties.

FIELD OF TECHNOLOGY

Aspects of the disclosure relate to providing apparatus and methods for repairing bone fractures. In particular, the disclosure relates to apparatus and methods for repairing and/or stabilizing bone fractures utilizing a device that is inserted into a bone.

BACKGROUND OF THE INVENTION

Currently, there are many known ways to treat long bone fractures. Common fracture treatments include: (1) nonsurgical immobilization; (2) osteosuture and tension band technologies; (3) percutaneous fixation (e.g., using pins, wires, screws etc.); (4) rigid intramedullary nailing (e.g., using a large rod and external screws); (5) flexible plate osteosynthesis (e.g., a "load sharing" suture); (6) arthroplasty (e.g., using a prosthesis); (7) plating and other indication specific techniques. Severe fractures that meet certain clinical criteria may require surgical repair rather than non-surgical immobilization.

The midshaft of an elongated or long bone is typically classified as the diaphysis.

In general, fracture fixation may provide longitudinal (along the long axis of the bone), transverse (across the long axis of the bone), and rotational (about the long axis of the bone) stability. Fracture fixation may also preserve normal biologic and healing function.

There are two primary categories for surgical fixation: a device that is within the skin (internal fixation); and a device that extends out of the skin (external fixation). There are two common types of internal fixation approaches for long bone surgery (a) a plate that is screwed to the outside of the bone; or (b) a rod that goes down the center of the bone.

Plates are characterized by relatively invasive surgery, support of fractured bone segments from one side outside of bone, and screws that anchor into the plate and through the entire bone. Successful repair is dependent on fracture pattern, bone quality, and patient tolerance of a foreign body, among other factors. Plates may not properly address the alignment and stability requirements for periarticular and intrarticular fractures.

Intramedullary rods or nails, such as those used in mid shaft treatments, are often used instead of plates and screws to reduce soft-tissue trauma and complications. Typically, an intramedullary rod or nail is fixed in diameter and is introduced into the medullary canal through an incision in the articular surface.

Flexible intramedullary rod-like solutions utilize structures that can be flexed for insertion into the medullary cavity through a diaphyseal or metaphyseal access site. The structures may then be made rigid inside the intramedullary cavity. The structures are often reinforced with polymers or cements. Making the structures rigid is important for surgical fixation.

It would be desirable, therefore, to provide apparatus and methods for bone fracture alignment and stabilization.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF PREFERRED EMBODIMENTS

Figure 1:
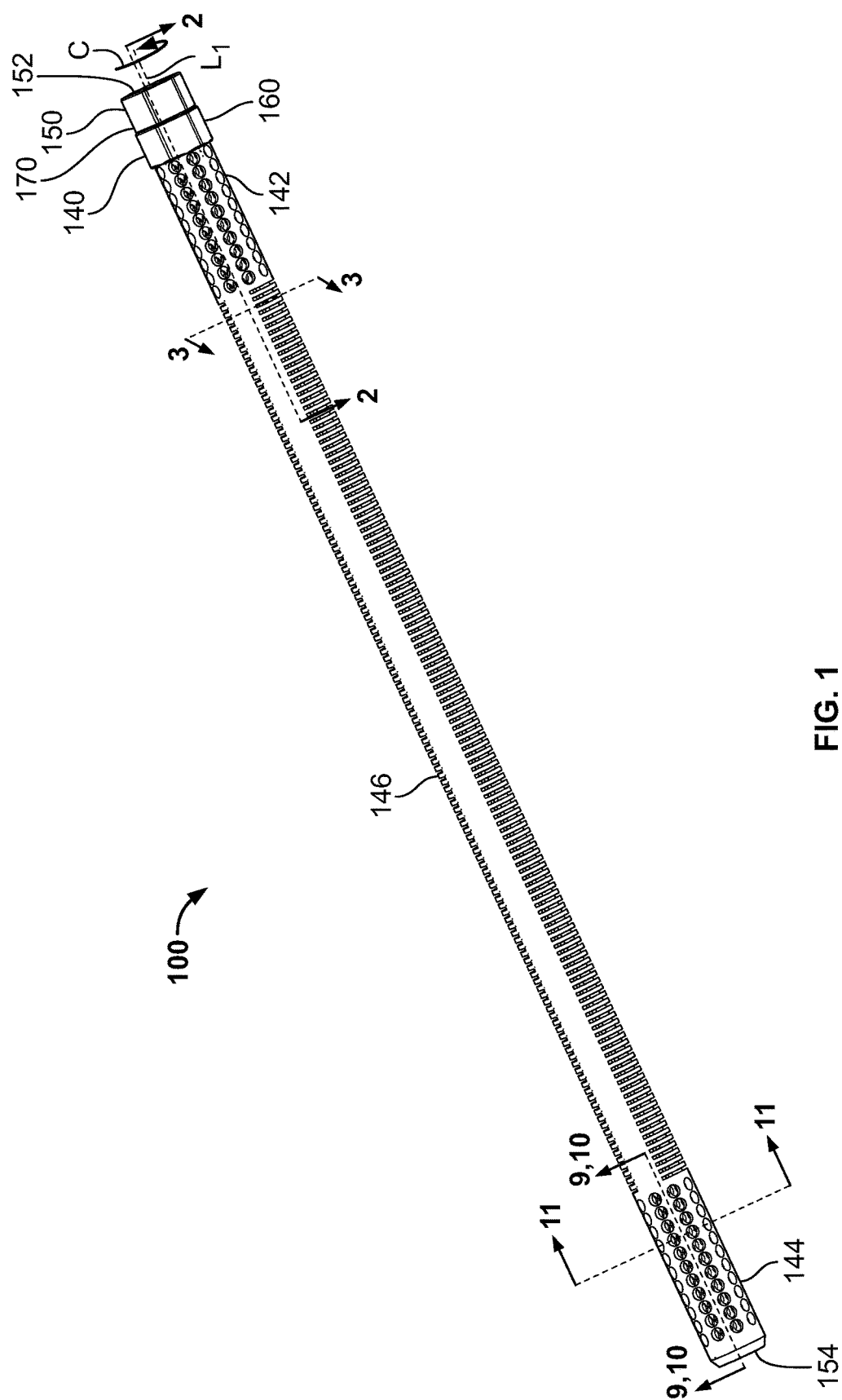
FIG. 1 shows illustrative apparatus in accordance with principles of the invention.

Apparatus and method for repairing a fractured bone are provided. The apparatus and methods may involve an intramedullary rod. The rod may include a first elongated member and a second elongated member. An elongated member may be referred to herein as a sleeve. Each of the first and second elongated members may be configured to bend in a first direction and to resist bending in a second direction. The first and second elongated members may be arranged such that: (1) the rod is bendable when the first direction of the first elongated member is aligned with the first direction of the second elongated member; and (2) the rod is rigid when the first direction of the first elongated member is aligned with the second direction of the second elongated member.

An elongated member may be an elongated tubular member. The first elongated member may be disposed coaxially within the second elongated member. The inner member may have a length that is longer, shorter or substantially the same as the length of outer member. The inner elongated member may include a central longitudinal void or may be solid, essentially solid or porous. The inner elongated member may rotate freely within an outer elongated member.

The elongated member may include implantable materials such as metals, polymers, composites and any other suitable materials.

The first direction may correspond to an arrangement of stress-relief features. The stress-relief features may include slots that are longitudinally spaced from each other. The slots may be stress-relief slots. The slots may be configured to provide tension relief. The slots may be configured to provide compression relief. Slots may be longitudinally separated by ribs. The ribs and/or slots may be circumferentially separated by one or more longitudinal members.

Slots may be formed by different cut patterns/arrangements in an elongated member. The different patterns/arrangements may provide different bending properties. Slots, holes or other void features may be provided by laser cutting or any other suitable method.

Different materials may be used to construct an elongated member, and different materials may provide different bending properties. Properties of features of an elongated member such as angular separation, thickness, height, separation, ratio of height to separation, composition or material, structure or microstructure or other suitable properties may provide different bending properties. The properties of an elongated member may vary along the longitudinal axis of the elongated member.

The stress-relief features may include any suitable microstructure, such as one or more of the following: sinters, kerfs, cuts, cells, perforations, holes, patterns, helical paths, cells, slots, tapers, angled cuts and any other suitable structure or microstructure.

The first direction of an elongated member may correspond to: (a) a first arrangement of slots that are longitudinally spaced from each other for tension relief; and (b) a second arrangement of slots that are longitudinally spaced from each other to provide compression relief. The first and second arrangements of slots may be spaced circumferentially apart from each other on one of the elongated members.

The apparatus may include a delivery cannula. The delivery cannula may provide a curved entry path into an intramedullary channel through an access hole in a bone.

The apparatus may include a control shaft. The control shaft may extend through the delivery cannula. The control shaft may manipulate one or more elongated members. The control shaft may be removed after elongated members are rotationally locked or rod is locked to bone. Anchors may lock an elongated member and attach rod to bone.

The intramedullary rod may include adjustment flanges. The adjustments flanges may be used to adjust the first and second elongated members relative to each other in a circumferential direction.

An elongated member may include an anchor-receiving feature. The anchor-receiving feature may include holes or voids in the elongated member. The anchor-receiving feature may be tapered, may include mesh-like cells that are configured to engage an anchoring device or may have different sizes, parameters or features. The spacing between the anchor-receiving features and the size and shape of the anchor-receiving features may be configured to cooperate with one or more types of different anchors. The anchor-receiving features may be may be sized as to interact/cooperate with each other. The anchor-receiving features may be sized or shaped differently to reduce or relieve angular stress between an inner and outer elongated member.

The first and second elongated members may include, respectively, a first anchor-receiving feature and a second anchor-receiving feature. The first and second elongated members may be configured to be positioned relative to each other such that the first anchor-receiving feature and the second anchor-receiving feature are positioned to receive the same anchor. The first and second anchor-receiving features may be distal the first and second arrangements of slots.

The first and second elongated members may include, respectively, a third anchor-receiving feature and a fourth anchor-receiving feature. The first and second elongated members may be configured to be positioned relative to each other such that the third anchor-receiving feature and the fourth anchor-receiving feature are positioned to receive the same anchor. The third and fourth anchor receiving features may be proximal the first and second arrangements of slots.

Anchors may penetrate one or more of the anchor-receiving features and secure one elongated member relative to another elongated member. Anchors may prevent the elongated members from rotating out of alignment. Anchors may penetrate bone and may used to apply tension across a bone fracture.

An elongated member may include one or more elastic sections. An elastic section may apply a compressive or a tensile force between proximal and distal anchors of the elongated member. The tensile force may be applied across the bone fracture by anchoring the elongated member such that the elastic section is in compression. The compressive force may be applied across the bone fracture by anchoring the elongated member such that the elastic section in tension.

The rod may include a locking mechanism. The locking mechanism may include: (a) a first attachment to the first elongated member; (b) a second attachment to the second elongated member; and (c) a bridging member that is configured to prevent relative rotation about the longitudinal axis of the first elongated member with respect to the second elongated member. One or both of the first and second attachments may be threaded.

The locking mechanism may include one or more of a threaded nut, a set screw, a cotter pin, a crimp, a swage, a morse taper and any other suitable mechanical interface or mechanism.

In some embodiments, the first elongated member may include a fixed-curve portion. The fixed-curve portion may have a fixed curve. The fixed curve may define a fixed-curve plane. The fixed curve plane may include the second direction of the first elongated member.

In some embodiments, the first elongated member may include a first fixed-curve portion and the second elongated member may include a second fixed-curve portion. The second fixed-curve portion may have a second fixed curve. The second fixed curve may define a second fixed-curve plane. The second fixed curve plane may include the second direction of the second elongated member.

In some embodiments, the intermedullary rod may be fixed in a rigid state that includes one or more straight sections and one or more curved sections. In some embodiments, rotation of a first elongated member relative to a second elongated member may cause rod to become rigid in a curved or bent configuration to provide mechanical support to different portions of a bone.

A fixed-curve portion may include a first segment and a second segment. A segment may be a compound segment. The second segment may be directly attached to the first segment. The first segment may include a first rigid bend. The second segment may include a second rigid bend. When the first and second bends lie in the fixed-curve plane: (a) the fixed-curve portion may be resistant to bending in the fixed-curve plane; and (b) the fixed curve portion may be non-resistant to bending in a plane that is different from the fixed-curve plane.

The first segment may be linked to the second segment by an articulating linkage. The articulating linkage may include a female linkage member and/or a male linkage member. The first and second segments may be formed from a unitary body. The unitary body may be a tube.

The first elongated member may include a segment that has a first end that includes a first linkage that has a first pivot axis. The first linkage may provide a connection to a first neighboring segment. The segment may have a second end that is spaced a distance apart from the first end. The second end may include a second linkage. The second linkage may include a second pivot axis. The second linkage may provide a connection to a second neighboring segment. The distance may define a longitudinal axis. The distance may define a direction that may be referred to as a longitudinal axis. The second pivot axis may be angularly offset, about the longitudinal axis, from the first pivot axis.

The first pivot axis may define the first direction of the first elongated member.

The second pivot axis may define the second direction of the first elongated member.

The segment may include a first end that includes a first linkage. The first linkage may have a first pivot axis. The first linkage may provide a connection to a first neighboring segment. The segment may include a second end. The second end may be spaced a distance apart from the first end. The second end may include a second linkage. The second linkage may have a second pivot axis. The second pivot axis may provide a connection to a second neighboring segment.

The distance may define a longitudinal axis. The distance may define a direction that may be referred to a longitudinal axis. The first and second pivot axes may define intersecting lines when the segment is viewed along a direction that is substantially normal to the longitudinal axis.

The first pivot axis may define the first direction of the first elongated member.

The second pivot axis may define the second direction of the first elongated member.

The second pivot axis may be angularly offset, about the longitudinal axis, from the first pivot axis.

A segment may include a segment body. The segment body may include one or more implantable material such as metal, polymer, composite and any other suitable material. The segment body may include one or more forms such as a cylinder, a prism, a curve and any other suitable shape.

The segment may be one of a chain of segments. The chain of segments may form all or a portion of the elongated member of the intermedullary rod. The segment chain may be placed inside an outer elongated member. The outer member may be provided with stress relief features that are distributed along the length and circumference of the member. A relative orientation of the chain and the outer elongated member may allow the rod to be oriented in a bendable or rigid orientation.

The rod may include a bone support extending from an end of the first and/or second elongated members. The end may be a proximal or a distal end. The rod may include two bone supports. One of the bone supports may extend from the first elongated member. The other may extend from the second elongated member.

The bone support may be fixed to one or more bone fragments. Fixation to bone may include using any suitable anchoring device.

In some embodiments, the rod may include an outer tubular member that is configured to bend about a first axis and an inner member disposed inside the outer tubular member. The inner member may include a segment that is configured to move: (a) relative to a first attached neighboring segment, about a second axis; and (b) relative to a second attached neighboring segment opposite the first attached neighboring segment, about a third axis.

The second axis may be substantially parallel to the first axis. The third axis may be substantially perpendicular to the first axis.

The inner member may be configured to rotate, relative to the outer tubular member, from a first position in which the second axis is parallel to the first axis, and the rod is bendable, to a second position in which the third axis is substantially perpendicular to the first axis, and the rod is resistant to bending.

The segment may be configured to move relative to the first and second neighboring segments by respective operation of first and second articulating linkages.

The segment, the first neighboring segment and the second neighboring segment may be formed from a unitary body. The unitary body may be a tube.

The methods may include a method for delivering an intramedullary rod to a bone. The method may include inserting a flexible intramedullary rod through an angled access hole into an intramedullary channel; and configuring the intramedullary rod in a rigid configuration by aligning a bending feature of a first sleeve with a non-bending feature of a second sleeve.

The method may include drilling the angled access hole at an angle to a longitudinal axis of the bone. The method may include preparing an intramedullary space to receive the rod. The method may include aligning the first and second sleeves to make the rod flexible. The method may include inserting the rod into the intramedullary space. The method may include rotating the first sleeve relative to the second sleeve to make the rod inflexible. The method may include fixing a rotational offset between the first sleeve and the second sleeve.

The method may include anchoring a distal end of the rod to the bone. The method may include applying a tension to the rod. The method may include anchoring a proximal end of the rod to the bone.

The method may include expanding a bone support at one end of the rod.

The apparatus and methods of the invention will be described in connection with embodiments and features of an illustrative bone repair device and associated hardware and instrumentation. The device and associated hardware and instruments will be described now with reference to the FIGS. It is to be understood that other embodiments may be utilized and structural, functional and procedural modifications may be made without departing from the scope and spirit of the present invention. It will be understood that features shown in connection with one or more of the embodiments may be practiced in accordance with the principles of the invention along with features shown in connection with other embodiments.

FIG. 1 shows illustrative rotary-rigid rod 100. Rod 100 may include outer sleeve 140 and inner sleeve 150. Inner sleeve 150 may have a length that is longer, shorter or substantially the same as the length of outer sleeve 140. The sleeves may be constructed of metal, polymer, composite or other suitable material. In some embodiments, the sleeves may be constructed from Nitinol tube. Void features, such as holes and slots, some of which are shown and described herein, may be provided by laser cutting or any other suitable method.

Outer sleeve 140 may include proximal end 142 and distal end 144. Inner sleeve 150 may include proximal end 152 and distal end 154. Outer sleeve 140 may include center section 146. Inner sleeve 150 may have corresponding center section 156 (shown in FIG. 2). Rotary-rigid rod 100, in the configuration shown in FIG. 1, may have longitudinal axis $L_1$. In some embodiments, rotary-rigid rod 100 may have an essentially annular cross section that is substantially perpendicular to axis $L_1$. Proximal end 142 and proximal end 152 may include, respectively, adjustment flanges 160 and 170. Adjustment flanges 160 and 170 may be used to adjust sleeves 140 and 150 relative to each other in circumferential direction C or −C about axis $L_1$.

Figure 2:
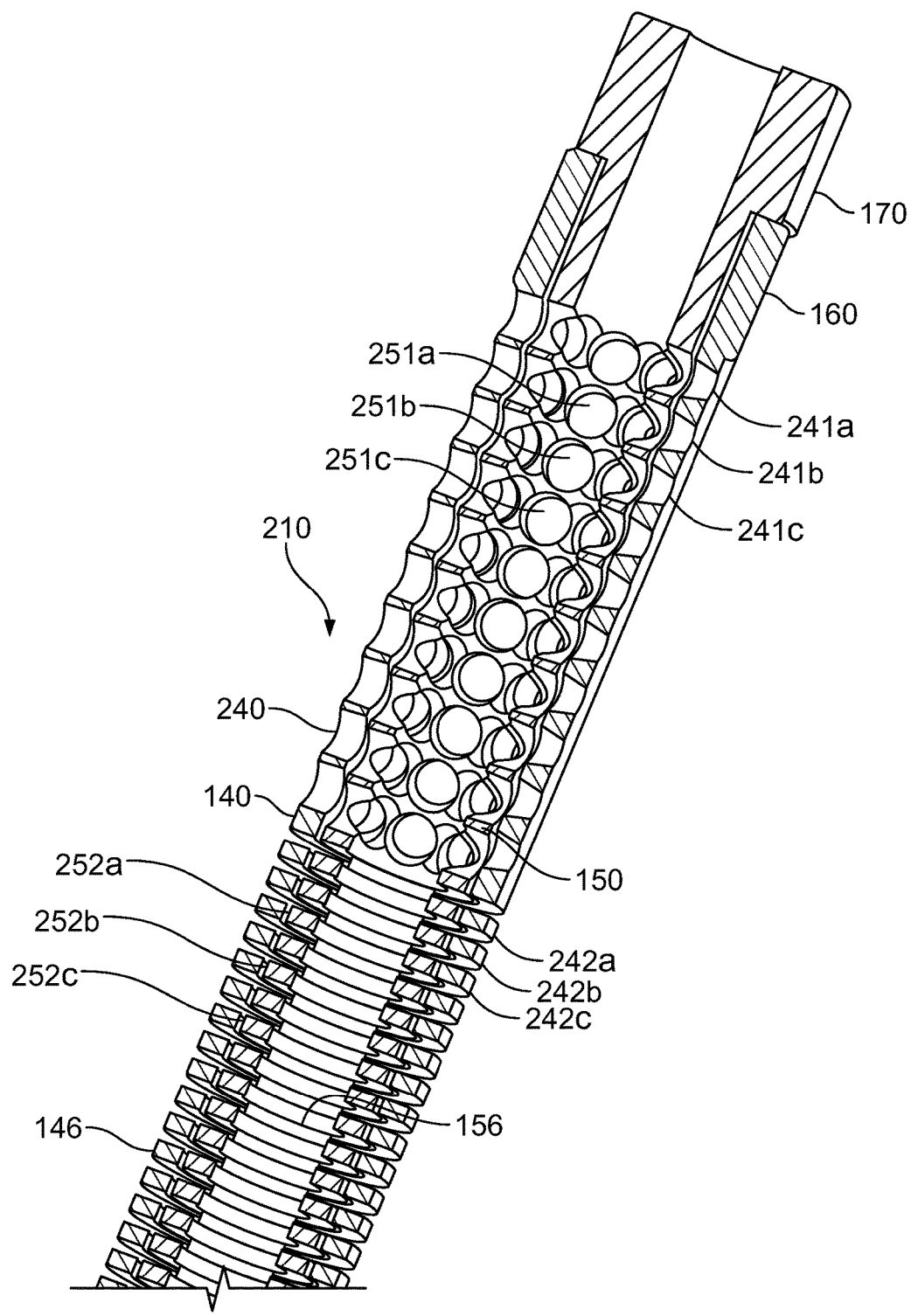
FIG. 2 shows a partial cross-section taken along lines 2-2 (shown in FIG. 1)

FIG. 2 shows a proximal portion of rotary-rigid rod 100. Inner sleeve 150 is shown substantially flush and coaxially aligned with outer sleeve 140. Inner sleeve 150 may include a central longitudinal void or may be solid, essentially solid or porous. Inner sleeve 150 may rotate freely within outer sleeve 140.

Outer sleeve 140 may include outer holes 241a, 241b and 241c, collectively referred to henceforth as outer holes 241. Inner sleeve 150 may include inner holes 251a, 251b and 251c, collectively referred to henceforth as inner holes 251. Outer holes 240 and inner holes 250 may be aligned or partially aligned when inner sleeve 150 is in one or more rotational positions with respect to outer sleeve 140.

While only a few of holes shown in FIG. 2 are labeled, it should be apparent that numerous holes of this type may be a part of rod 100. The holes may include mesh-like cells that are configured to engage an anchoring device.

In some embodiments, rod 100 may include corresponding holes in distal ends of sleeves 140 and 150.

Outer sleeve center section 146 may include outer ribs 242a, 242b and 242c, collectively referred to henceforth as outer ribs 242. Inner sleeve center section 156 may include inner ribs 252a, 252b and 252c, collectively referred to henceforth as inner ribs 252.

Figure 2A:
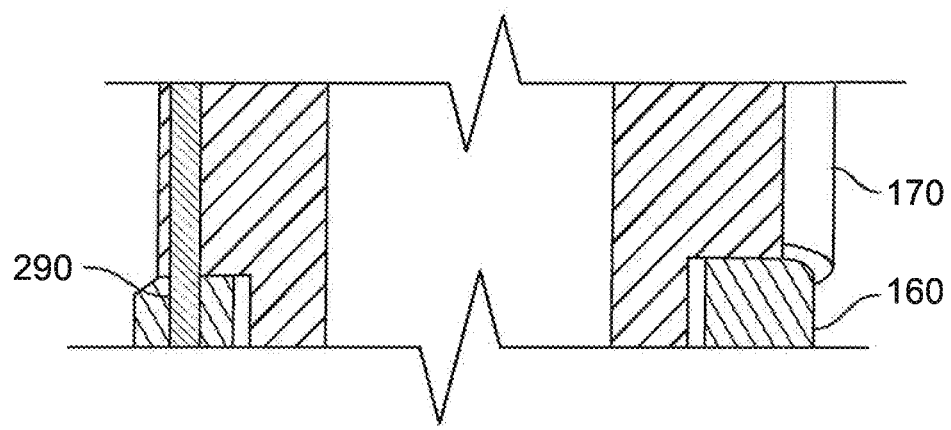
FIG. 2A shows a portion of the apparatus shown in FIG. 2 in a different state from that shown in FIG. 2.

FIG. 2A shows illustrative setting element 290 bridging between flanges 160 and 170.

Figure 3:
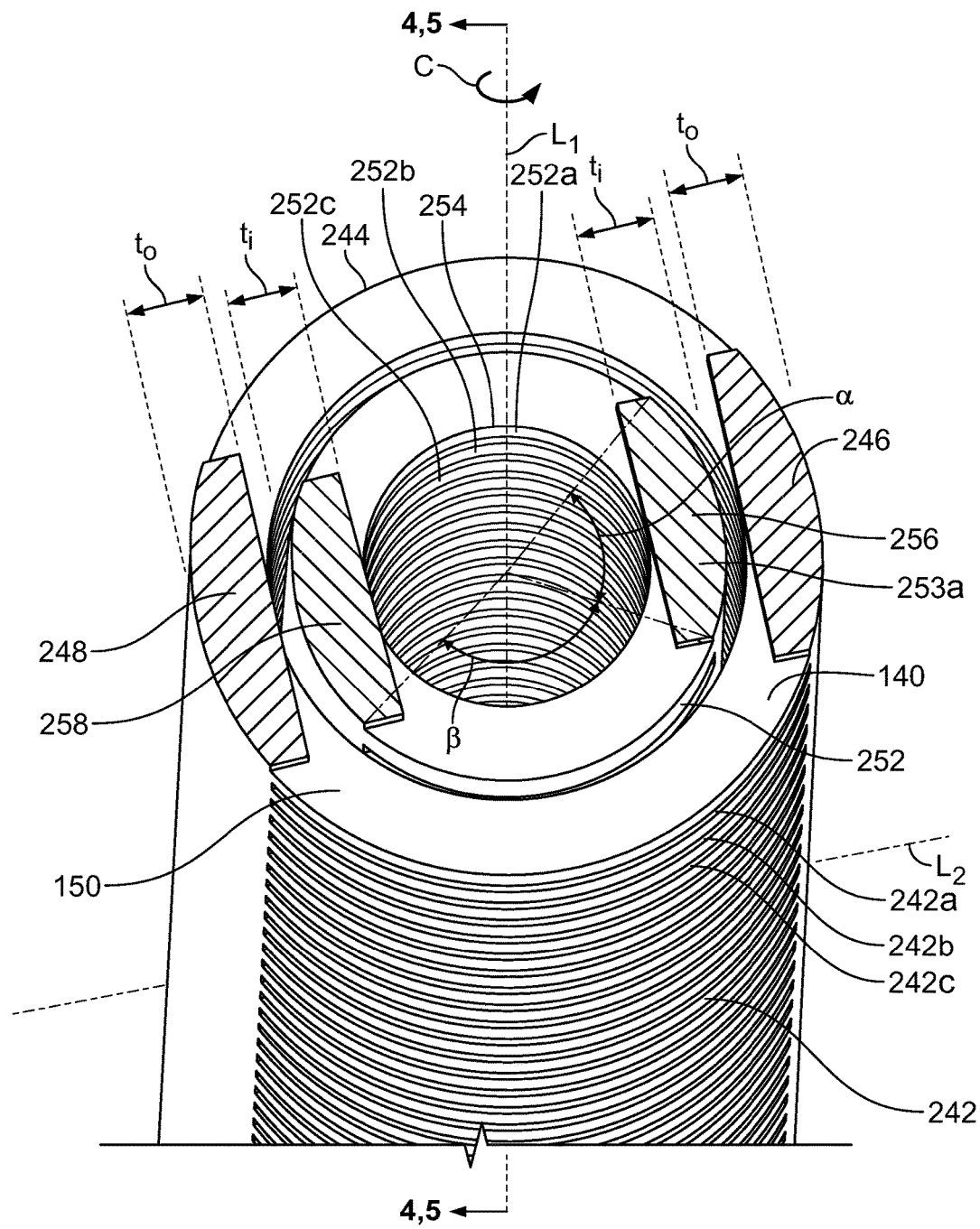
FIG. 3 shows a perspective view, taken approximately along lines 3-3, of a portion of the apparatus shown in FIG. 1, when the apparatus is in a first configuration.

FIG. 3 shows outer sleeve 140 and inner sleeve 150 in an aligned configuration. In the aligned configuration, outer ribs 242 are aligned in circumferential direction C with inner ribs 252. Inner ribs 254, opposite inner ribs 252, are aligned with outer ribs 244, opposite outer ribs 242. Outer ribs 242 and 244 may be circumferentially separated from each other by longitudinal members 246 and 248. Inner ribs 252 and 254 may be circumferentially separated from each other by longitudinal members 256 and 258.

Angle α defines the circumferential extent of member 256. Angle α may have any suitable magnitude. For example, angle α may range from a fraction of a degree to almost 180 degrees. In some embodiments, angle α may be about 90 degrees. Corresponding angles define the circumferential extent of members 246, 248 and 258. In some embodiments, one or more of the angles corresponding to angle α may have a magnitude that is different from that of angle α.

Angle β defines the circumferential separation between members 256 and 258. Angle β may have any suitable magnitude. For example, angle β may range from a fraction of a degree to almost 180 degrees. In some embodiments, angle β may be about 90 degrees. A corresponding angle defines the circumferential separation between members 246 and 248. In some embodiments, one or more of the angles corresponding to angle β may have a magnitude that is different from that of angle β.

Different magnitudes of angles α and β, and the corresponding angles, may produce in each of sleeves 140 and 150 different bending properties along axis $L_1$. When the sleeves are rotated about axis $L_1$ relative to each other, rod 100 may exhibit different bending properties based on the different angular magnitudes.

For example, outer ribs 242 and 244 permit outer sleeve 140 to bend along axis $L_1$ (about axis $L_2$) in the direction of either outer rib portion. Inner ribs 252 and 254 permit inner sleeve 150 to bend along axis $L_1$ (about axis $L_2$) in the direction of either inner rib portion.

To the extent that inner ribs and outer ribs are non-aligned with each other, rod 100 may exhibit resistance to bending along axis $L_1$.

Increased thickness $t_o$ of longitudinal members 246 and 248 may increase the bending resistance of outer member 140 along axis $L_1$ about axis $L_2$. Increased thickness $t_i$ of longitudinal members 256 and 258 may increase the bending resistance of inner member 150 along axis $L_1$ about axis $L_2$.

Figure 4:
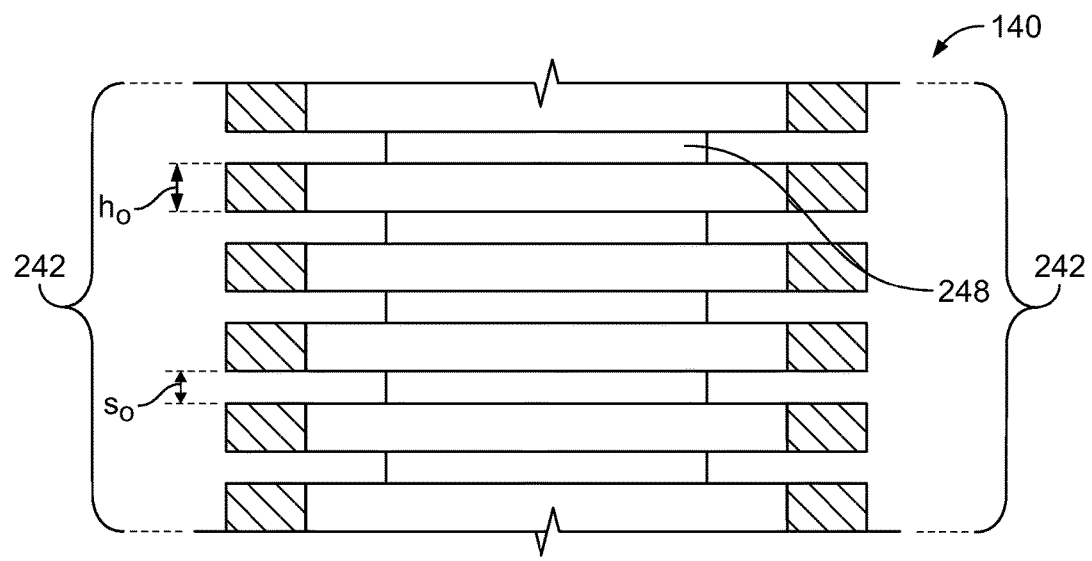
FIG. 4 shows a partial cross-section taken along the lines 4-4 (shown in FIG. 3).
Figure 5:
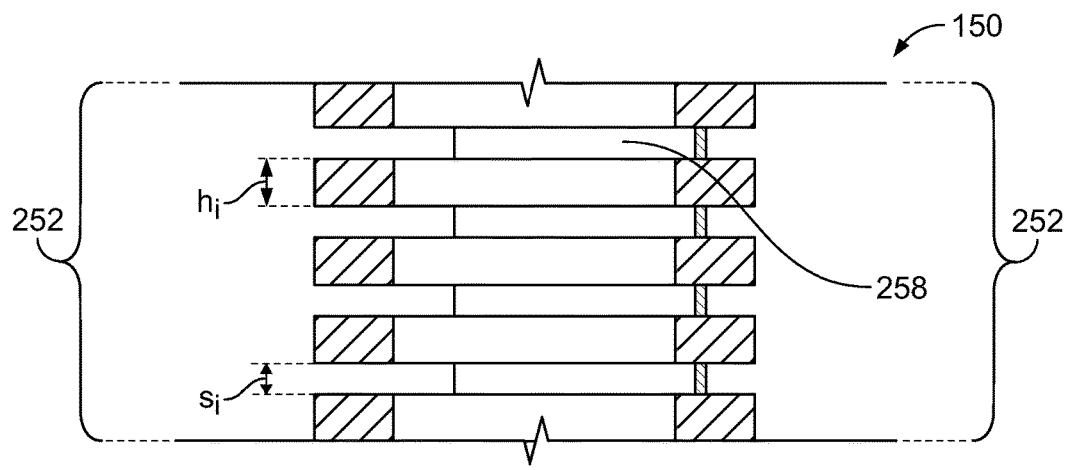
FIG. 5 shows a partial cross-section taken along the lines 5-5 (shown in FIG. 3).

FIGS. 4 and 5 show heights $h_o$ and $h_i$ of ribs 242 and 252, respectively. Ribs 242 and 252 may be spaced apart by spacings $s_o$ and $s_i$, respectively. Relatively greater or lesser ratios $h_o:S_o$ and $h_i:s_i$ may decrease or increase, respectively, the bending resistances of sleeves 140 and 150.

One or more of longitudinal members 246, 248, 256 and 258 may include a composition or material that provides a relatively greater or lesser degree of bending resistance along axis $L_1$ about axis $L_2$. Suitable compositions or materials may include implantable materials such as metals, polymers, composites and any other suitable materials.

One or more of longitudinal members 246, 248, 256 and 258 may include a structure or microstructure that provides a relatively greater or lesser degree of bending resistance along axis $L_1$ about axis $L_2$. Suitable structure or microstructure may include: sinter, kerfs, cuts, cells, perforations, holes, patterns, helical paths, cells, slots, tapers, angled cuts and any other suitable structure or microstructure.

Properties such as angle α, angle β, thickness $t_o$, thickness $t_i$, height $h_o$, height $h_i$, separation $s_o$, separation $s_i$, ratio $h_o:s_o$, ratio $h_i:s_i$, composition or material, structure or microstructure and other suitable properties may vary along axis $L_1$.

Figure 6:
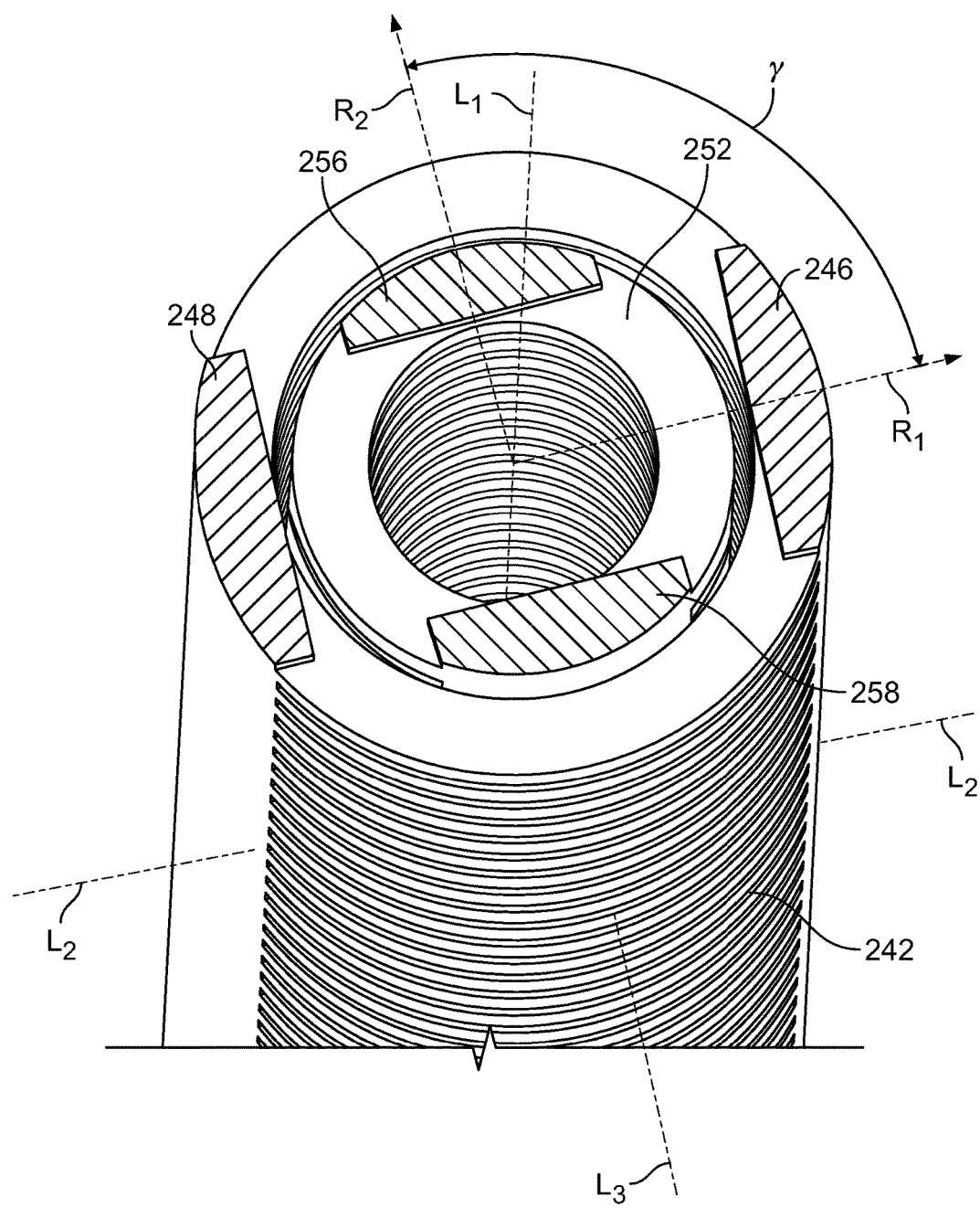
FIG. 6 shows the view of FIG. 3 when the apparatus is in a second configuration.

FIG. 6 shows inner sleeve 150 rotated by angle γ relative to outer sleeve 140. Inner ribs 252 are now aligned with longitudinal member 246. Outer member 246 may thus provide resistance to a bending moment about axis $L_3$.

Longitudinal member 248 may provide corresponding resistance on the opposite side of rod 100. Longitudinal members 256 and 258 may similarly provide resistance to bending about axis $L_2$. When γ is at or near 0°, bending resistance of rod 100 along $L_1$ about $L_2$ will be relatively greater. When γ is at or near 90°, bending resistance of rod 100 will be relatively lesser.

Figure 7:
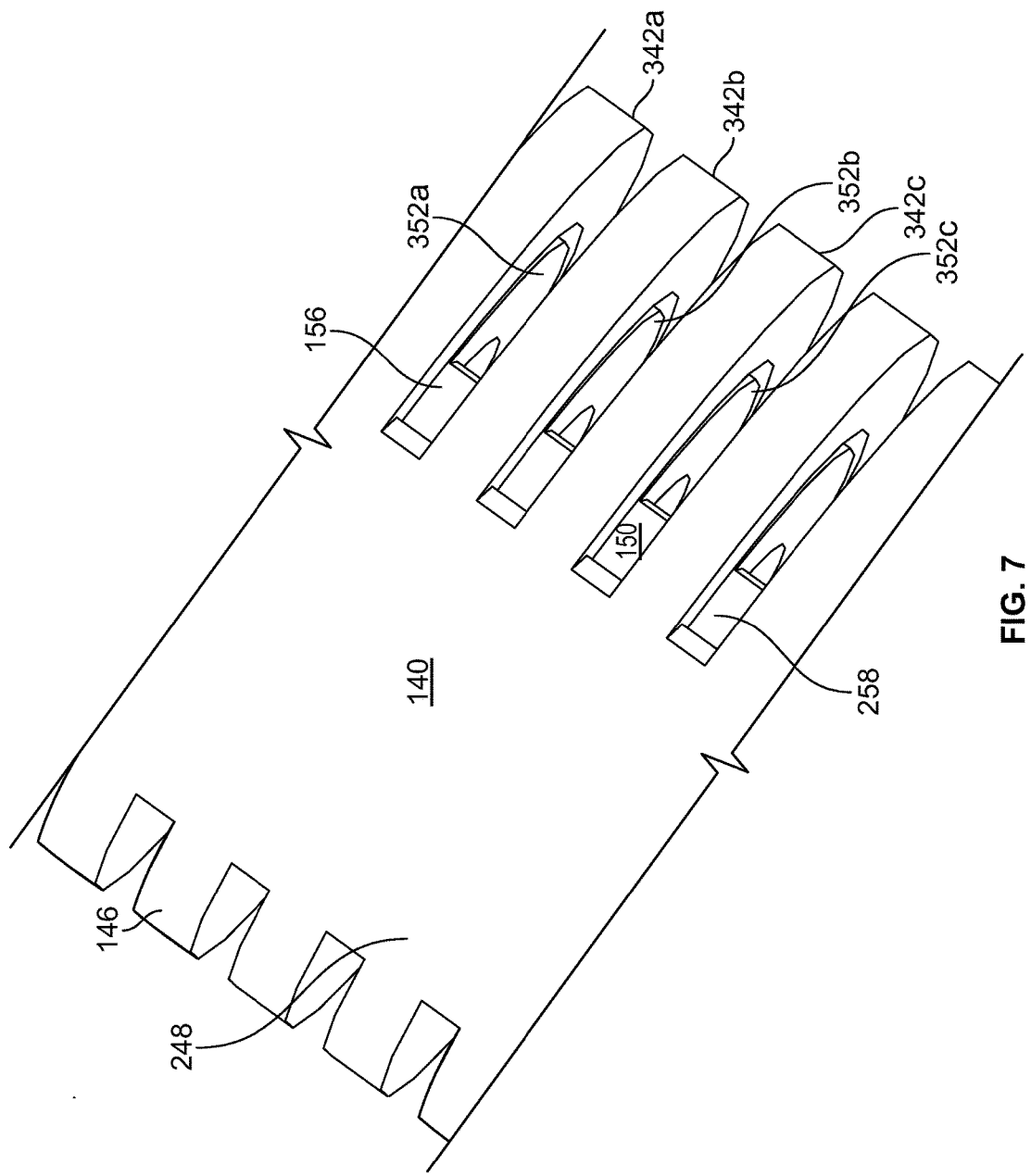
FIG. 7 shows a perspective view of a portion of the apparatus shown in FIG. 1.

FIG. 7 shows portions of outer sleeve 140 and inner sleeve 150 in perspective view when γ is slightly greater than 0°.

Figure 8:
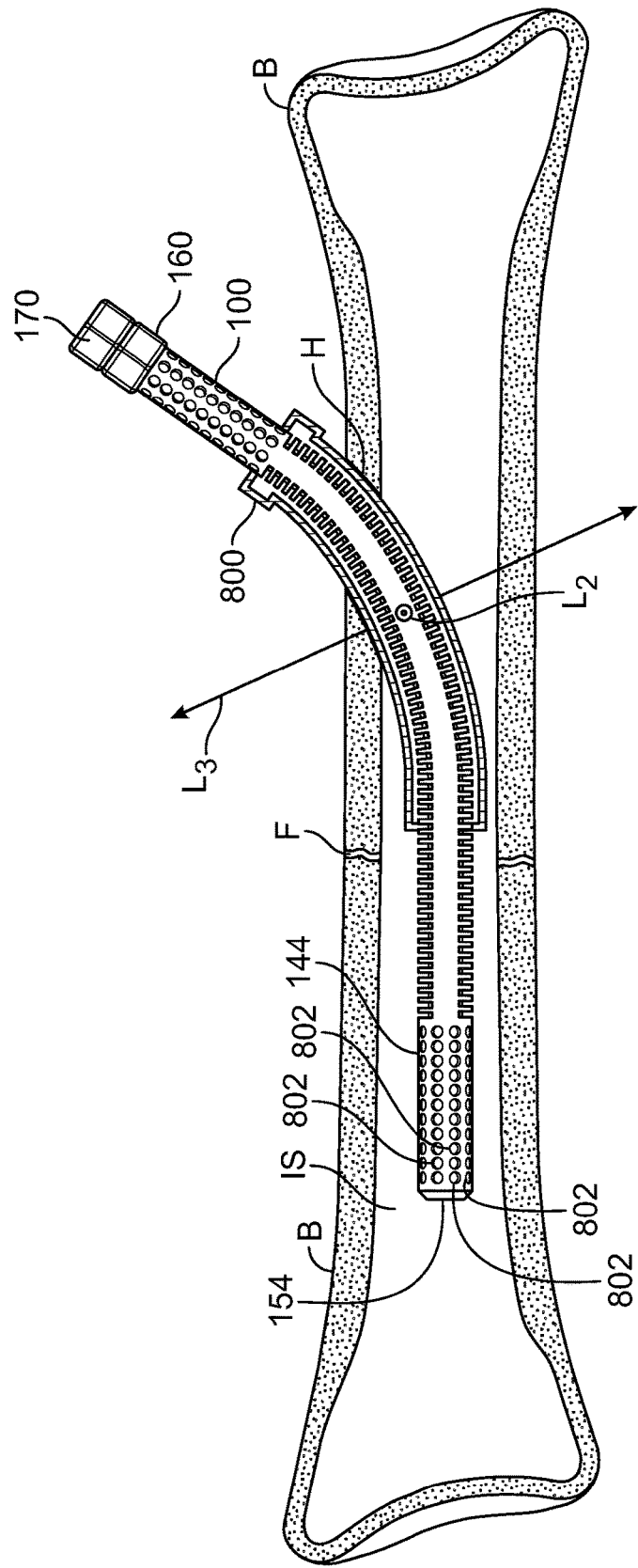
FIG. 8 shows the apparatus of FIG. 1, along with other apparatus and a bone.

FIG. 8 shows rod 100 when γ is at or near 0°, bending upon delivery to intramedullary space IS in bone B. Bone B includes mid-shaft fracture F. Angled delivery tube 800 is present in angled access hole H in bone B. Outer sleeve 150 and inner sleeve 140 are aligned so that rod 100 can bend about axis $L_2$. (It will be appreciated that axes $L_2$ and $L_3$ are not fixed longitudinally along axis $L_1$.)

After placement in intramedullary space IS, outer sleeve 140 and inner sleeve 150 may be rotated such that γ is at or near 90° to provide rod 100 with bending resistance. In some embodiments, the rotation may provide rod 100 with rigidity.

In some embodiments, rod 100 may be anchored after setting γ at a desired value. Rod 100 may anchor distal fracture F by fastening anchors in holes 802 at distal ends 144 and 154 of rods 140 and 150, respectively. Rod 100 may anchor proximal fracture F by fastening anchors in holes such as 240 and 250 (shown in FIG. 2) in proximal ends 142 and 152 of outer and inner sleeves 140 and 150, respectively.

Anchors such as screws that penetrate an outer and an inner hole secure outer sleeve 140 relative to inner sleeve 150 and prevent the sleeves from rotating out of alignment. Any suitable type of anchor may be used.

Compression or tension may be applied across fracture F between the distal and proximal fastenings. The tension may be applied by a practitioner after the distal anchors are placed. Rod 100 may include one or more elastic sections. An elastic section may apply a compressive or a tensile force between proximal and distal anchors of rod 100. The tensile force may be applied across fracture F by anchoring rod 100 such that the elastic section is in compression. The compressive force may be applied across fracture F by anchoring rod 100 such that the elastic section in tension.

In some embodiments, adjustment flanges 160 and 170 may be set relative to each other to prevent sleeves 140 and 150 from rotating out of alignment. The setting may be based on inter-threading, cooperating keyed members, a keyed or mating outer sleeve, a pin or any other suitable mechanism.

Setting elements may be integrated into rod 100 at proximal or distal ends of rod 100 or anywhere along the length of rod 100. The setting elements may be separate from rod 100. The setting elements may include one or more of a threaded nut, a set screw, a cotter pin, a crimp, a swage, a morse taper and any other suitable mechanical interface or mechanism.

FIG. 8 shows holes 802 in distal end 144 of outer sleeve 140.

Figure 9:
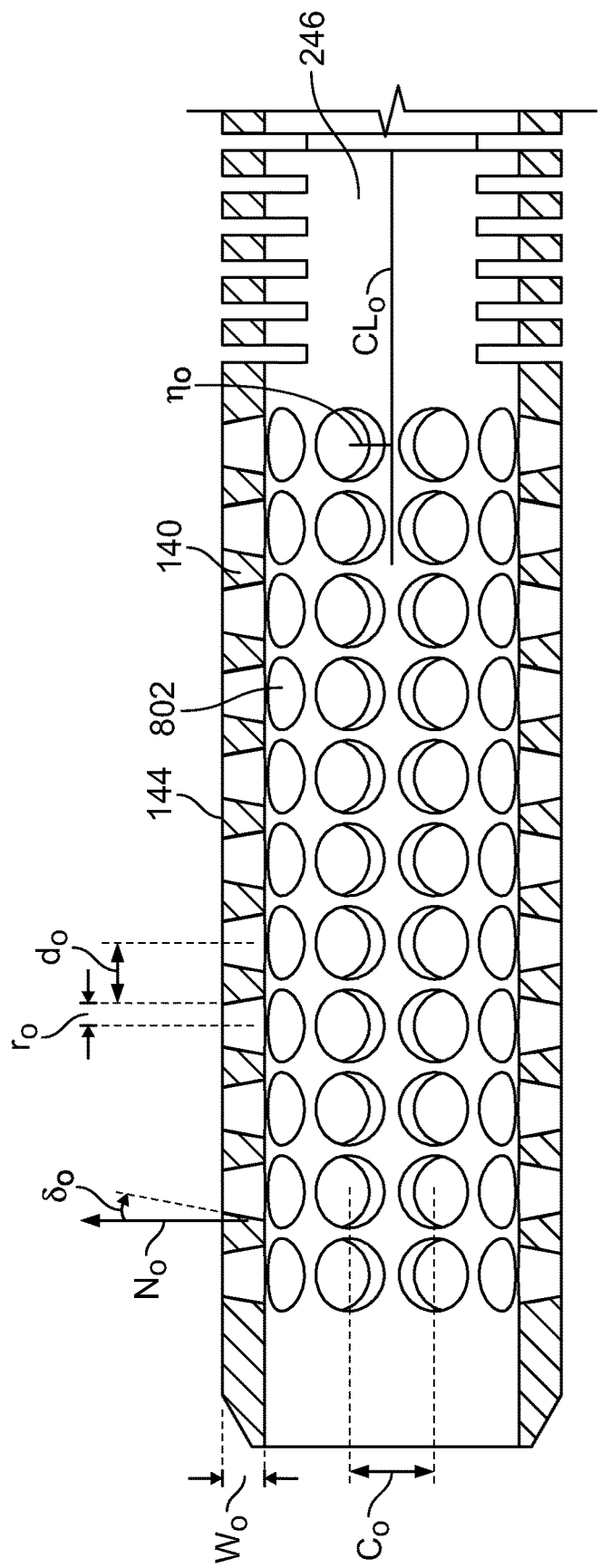
FIG. 9 shows a partial cross-sectional view of a portion of the apparatus shown in FIG. 1 taken along lines 9-9 (shown in FIG. 1).

FIG. 9 shows that holes 802 may pass through wall thickness $w_o$ of distal end 144. One or more of holes 802 may be tapered at angle $\delta_o$ relative to normal direction $N_o$. One or more of holes 802 may have a radius $r_o$. Two or more holes 802 may be longitudinally spaced apart by distance $d_o$. Two or more of holes 802 may be circumferentially spaced apart by arc length $c_o$. Two or more of holes 802 may be offset from longitudinal member 246 centerline $CL_o$ by arc length $\eta_o$. One or more of parameters $w_o$, $\delta_o$, $r_o$, $d_o$, $c_o$, $\eta_o$, and any other suitable parameters, may be configured to cooperate with one or more types of anchors. One or more of parameters $w_o$, $\delta_o$, $r_o$, $d_o$, $c_o$, $\eta_o$, and any other suitable parameters, may be configured to cooperate with one or more types of anchors and one or more of corresponding parameters $w_i$, $\delta_i$, $r_i$, $d_i$, $c_i$, $\eta_i$ (shown in FIG. 10).

Figure 10:
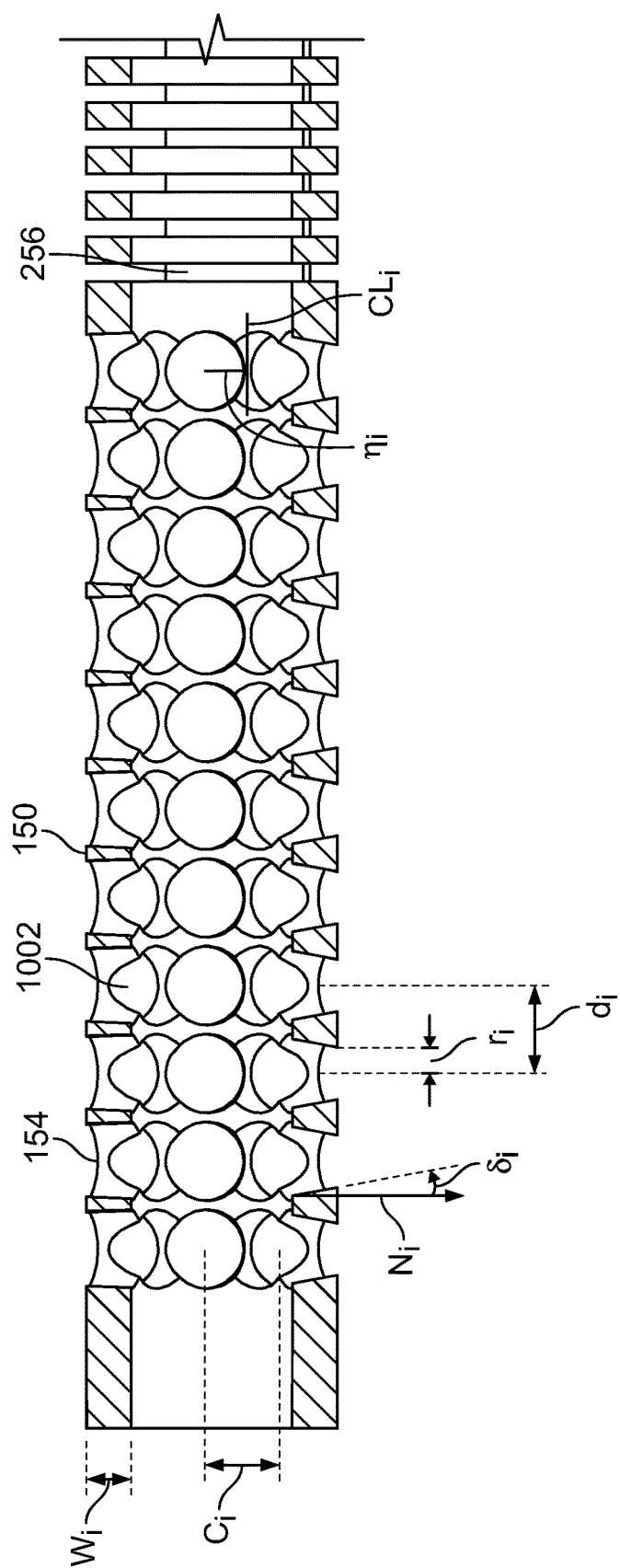
FIG. 10 shows a partial cross-sectional view of a portion of the apparatus shown in FIG. 1 taken along lines 10-10 (shown in FIG. 1).

FIG. 10 shows holes 1002 in wall thickness $w_i$ of distal end 154. One or more of holes 1002 may be tapered at angle $\delta_i$ relative to normal direction $N_i$. One or more of holes 1002 may have a radius $r_i$. Two or more holes 802 may be longitudinally spaced apart by distance $d_i$. Two or more of holes 1002 may be circumferentially spaced apart by arc length $c_i$. Two or more of holes 1002 may be offset from longitudinal member 256 centerline $CL_i$ by arc length $\eta_i$. One or more of parameters $w_i$, $\delta_i$, $r_i$, $d_i$, $c_i$, $\eta_i$, and any other suitable parameters, may be configured to cooperate with one or more types of anchors. One or more of parameters $w_i$, $\delta_i$, $r_i$, $d_i$, $c_i$, $\eta_i$, and any other suitable parameters, may be configured to cooperate with one or more types of anchors and one or more of corresponding parameters $w_o$, $\delta_o$, $r_o$, $d_o$, $c_o$, $\eta_o$ (shown in FIG. 9).

One or more of holes 240 and 250 (shown in FIG. 2) may have one or more parameter or feature that is similar to one or more of the parameters and features discussed in connection with holes 802 and 1002.

Figure 11:
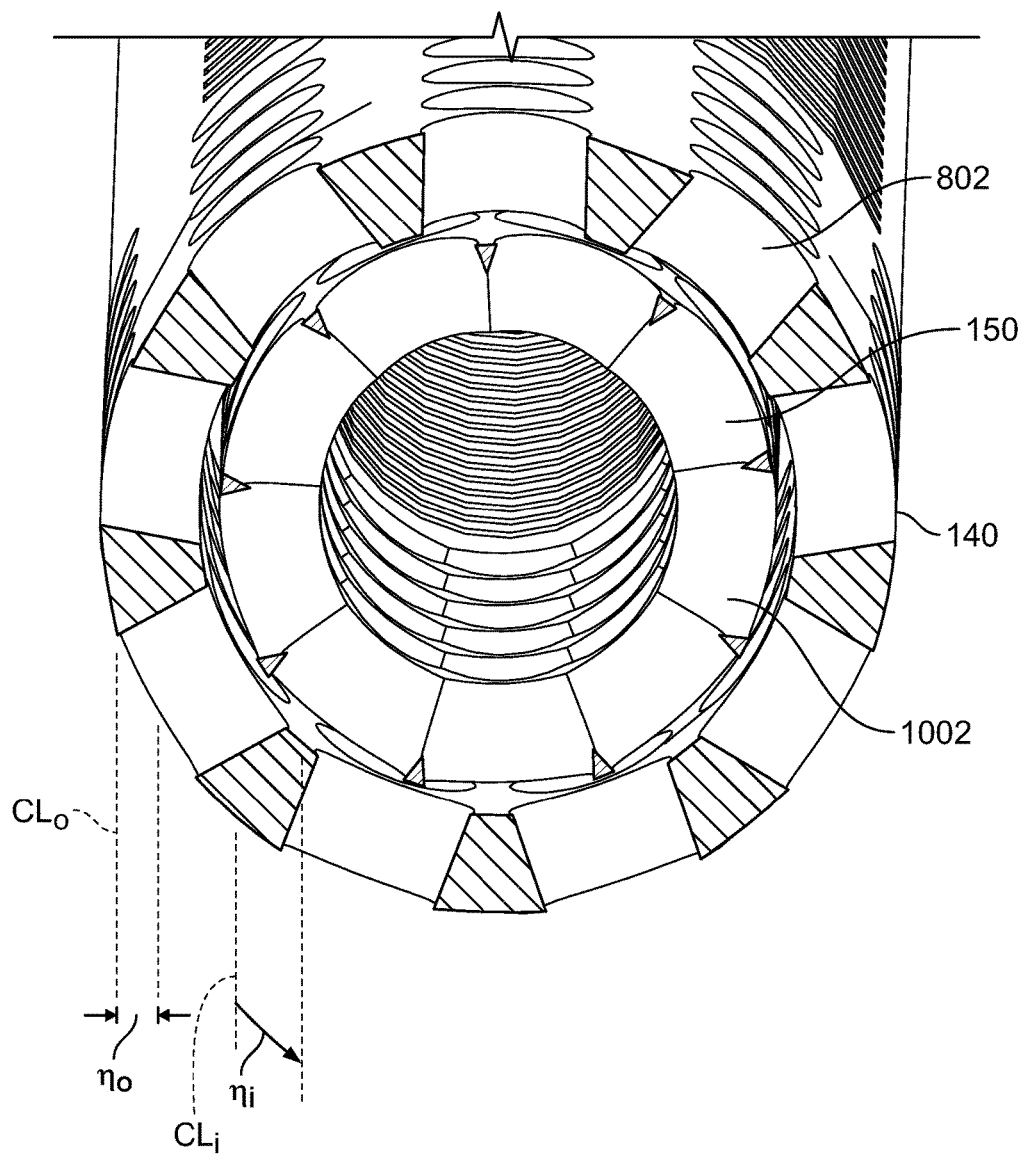
FIG. 11 shows a partial cross-sectional view taken along lines 11-11 (shown in FIG. 1) when the apparatus is in a configuration that is different from that shown in FIG. 1.

FIG. 11 shows outer sleeve 140 and inner sleeve 150 with angle γ (shown in FIG. 6) at approximately 0°. Outer holes 802 are offset from longitudinal member 246 (shown in FIG. 3) centerline $CL_o$ by arc length $\eta_o$. Inner holes 1002 are offset from longitudinal member 256 (shown in FIG. 3) centerline $CL_i$ by arc length $\eta_i$.

One or more of holes 240, 340, 802 and 1002 may have any suitable shape. Each of proximal and distal ends of outer sleeve 140 and inner sleeve 150 may include holes of different sizes, parameters and features.

Inner and outer holes may be sized or shaped differently to reduce or relieve angular stress between sleeve 140 and sleeve 150 when sleeves 140 and 150 are angularly locked relative to each other.

Figure 12:
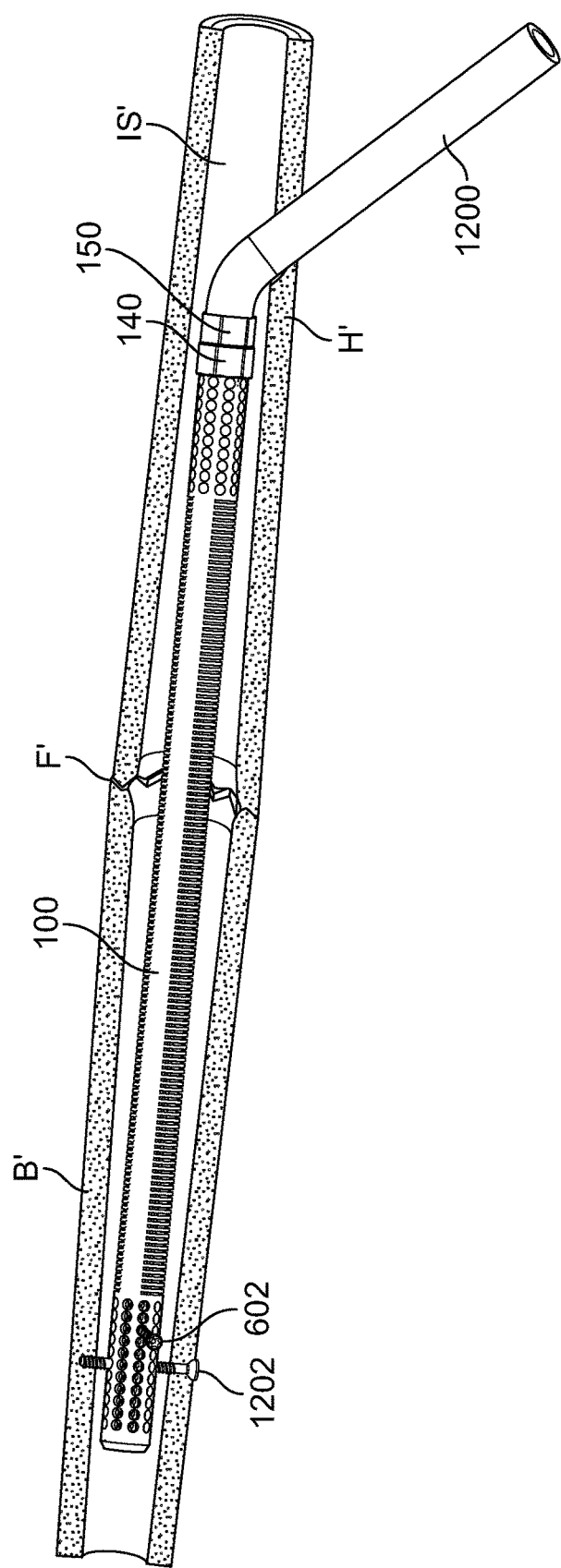
FIG. 12 shows the apparatus of FIG. 1, along with other apparatus and a different bone.

FIG. 12 shows rod 100 in intramedullary cavity IS' within bone B', which may be a femur or other long bone. Bone B' is fractured at fracture F'. Delivery cannula 1200 may provide a curved entry path into cavity IS' through hole H' in bone B'.

Delivery cannula 1200 may be used to rotate outer sleeve 140 relative to inner sleeve 150 to make rod 100 rigid or partially rigid. For example, cannula 1200 may engage the proximal end of outer sleeve 140. A control shaft (not shown) may extend through cannula 1200 and engage inner sleeve 150. The control shaft may rotate inner sleeve 150 relative to outer sleeve 140. The control shaft and cannula 1200 may then be disengaged from rod 100.

Anchors 1202 lock outer sleeve 140 and inner sleeve 150 rotationally with respect to each other. Anchors 1202 also secure rod 100 to bone B'.

In some embodiments, cannula 1200 may be disengaged after the inner and outer sleeves are rotationally locked. In some embodiments, cannula 1200 may be disengaged after the inner and outer sleeves are anchored to bone B'.

In some embodiments, the rod inner or outer sleeves may include more than one pair of longitudinal members. For example, an inner or outer sleeve may include two pairs of longitudinal members.

Figure 13:
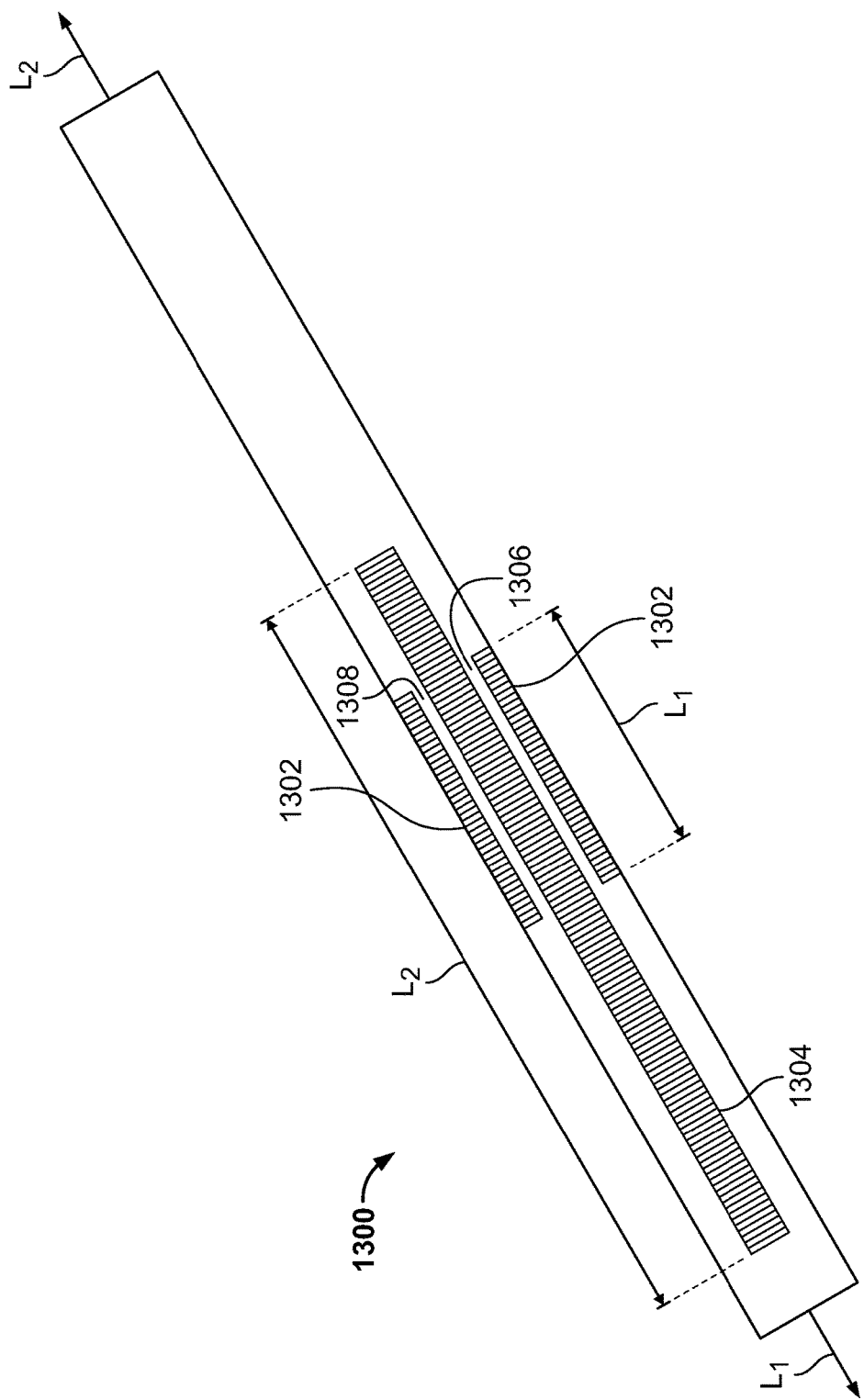
FIG. 13 shows a flat model representation of features of apparatus such as that shown in FIG. 1.

FIG. 13 shows illustrative cut-pattern 1300 for a sleeve such as outer sleeve 140 (shown in FIG. 1). Pattern 1300 may be a laser-cut pattern. Pattern 1300, which is shown flat for illustration, may be cut in a cylindrical tube to provide compression relief on one side of the tube and relief on the other side of the tube. Pattern 1300 may include cut arrangement 1302 having length $L_1$. Pattern 1300 may include cut arrangement 1304 having length $L_2$. Lengths $L_1$ and $L_2$ may be any suitable length and may be the same as each other or different from each other. Regions 1306 and 1308 may correspond to longitudinal members such as 246 and 248 (shown in FIG. 3), respectively.

Figure 14:
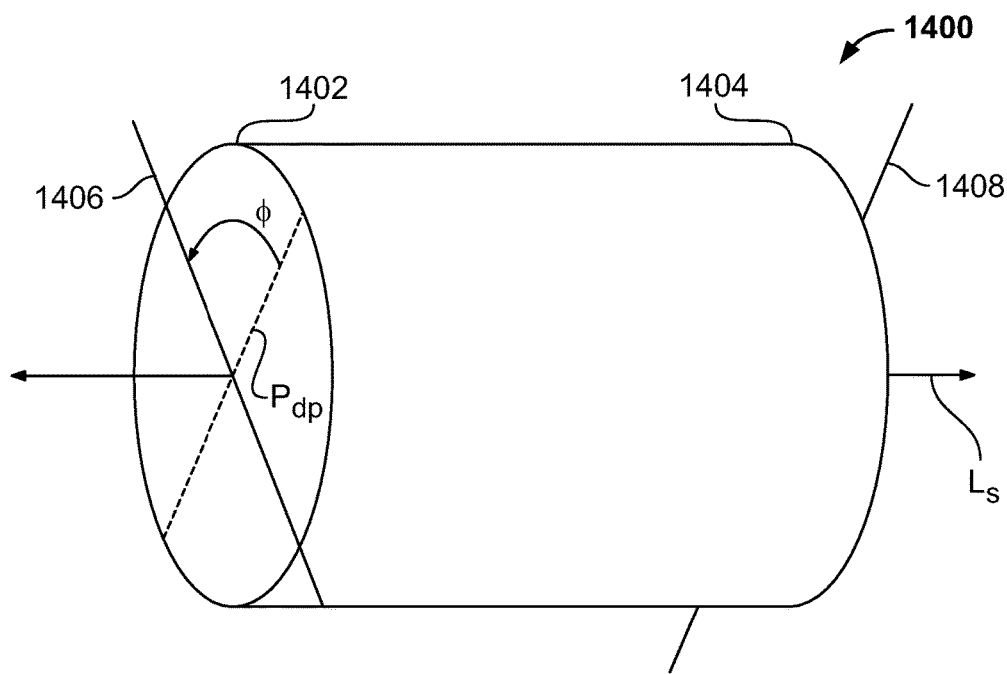
FIG. 14 shows schematic apparatus in accordance with the principles of the invention.
Figure 15:
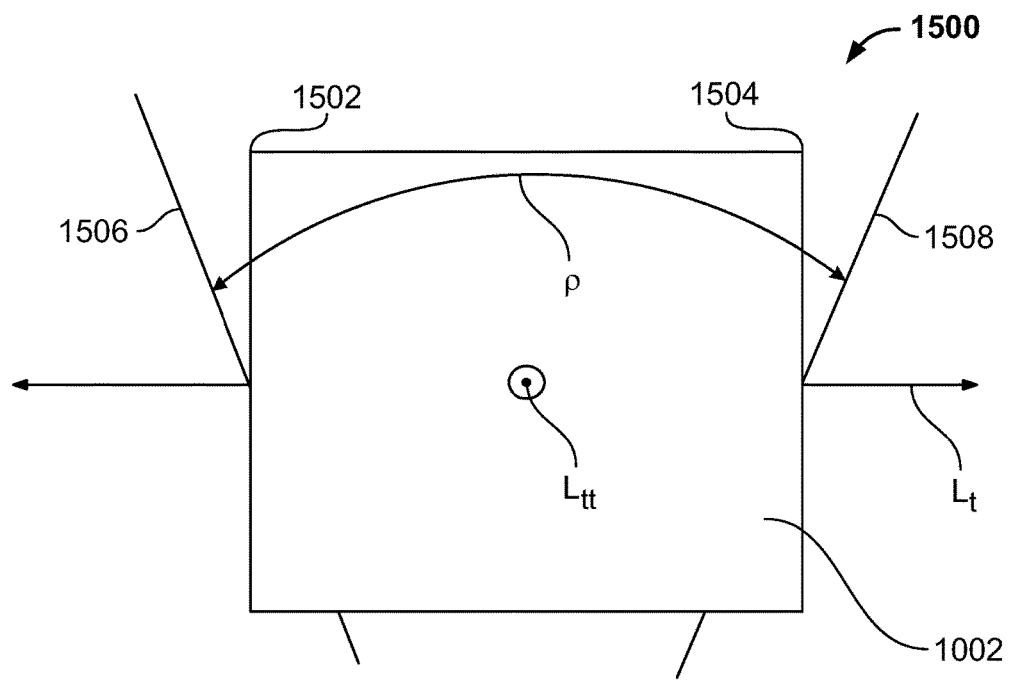
FIG. 15 shows other schematic apparatus in accordance with the principles of the invention.

FIGS. 14 and 15 illustrate principles of an intramedullary rod that includes an inner elongated member and an outer tubular member. The rod may be fixed in a rigid state that includes one or more straight sections and one or more curved sections.

FIG. 14 shows schematically illustrative segment 1400 that may be one of a chain of segments (not shown) in an inner elongated member of an intramedullary rod. Segment 1400 may have proximal end 1402 that is spaced apart from distal end 1404. Longitudinal axis Ls may extend at least from proximal end 1402 through distal end 1404. Pivot axis 1406 at proximal end 1402 and pivot axis 1408 at distal end 1404 are axes about which segment 1400 may move relative to a proximal neighboring segment and a distal neighboring segment, respectively.

Projection $P_{dp}$ is the projection of distal pivot axis 1408 onto proximal end 1402. Distal pivot axis 1408 is offset, about axis Ls, from proximal pivot axis 1406, by angle $\phi$. $\phi$ may be any suitable angle from about 0° to about 90°.

An intramedullary rod may include the segment chain and an outer sleeve. The segment chain may be placed inside the outer sleeve. The outer sleeve may be provided with stress relief features that are distributed along the length and circumference of the sleeve. In a first relative orientation of the chain and the outer sleeve, the stress relief features may align with one or both of the pivot axes and the rod may be bendable about the aligned axes.

In a second relative orientation of the chain and the outer sleeve, the stress relief features may be nonaligned with respect to one or both of the pivot axes and the rod may be rigid about the nonaligned axes and curved based on curvature (not shown) within segment 1402 along axis Ls. The curvature may be any suitable curvature.

FIG. 15 shows schematically illustrative segment 1500 that may be one of a chain of segments (not shown) in an inner elongated member of an intramedullary rod. Segment 1500 may have proximal end 1502 that is spaced apart from distal end 1504. Longitudinal axis $L_t$ may extend at least from proximal end 1502 through distal end 1504. Pivot axis 1506 at proximal end 1502 and pivot axis 1508 at distal end 1504 are axes about which segment 1500 may move relative to a proximal neighboring segment and a distal neighboring segment, respectively.

Distal pivot axis 1508 is offset, about transverse axis $L_{tt}$, from proximal pivot axis 1506, by angle $\rho$. $\rho$ may be any suitable angle from about 0° to about 90°. A chain of segments such as 1500, along with an outer sleeve with suitable stress relief, may be used to provide an intramedullary rod that is flexible in a first configuration, but rigid-and curved-in a second configuration. The rod may be rigid and curved by angle $\rho$ in conjunction with any curvature that may be present in segment 1500 along axis $L_t$.

Compound segments may have proximal and distal pivot axes that are offset contemporaneously by an angle such as $\phi$ (shown in FIG. 14) and an angle such as $\rho$.

An inner elongated member of an intramedullary rod may include segments such as 1400, 1500, compound segments, and any suitable combination that are embodied as separate articulating chain links. An inner elongated member of an intramedullary rod may include segments such as 1502, 1504 and compound segments that are embodied as adjacent portions of a unitary member, such as one formed from a laser-cut tube. The segments may be distributed along the rod to provide flexibility for insertion into a bone and straight or curved rigid sections to distribute stiffness in conformance with bone anatomy. One or more of the segments that provide curved rigid support may be used in conjunction with apparatus for providing straight rigid support.

FIGS. 16-21 show illustrative features of embodiments that may include rod sections that may have flexible and rigid curved or bent states.

Figure 16:
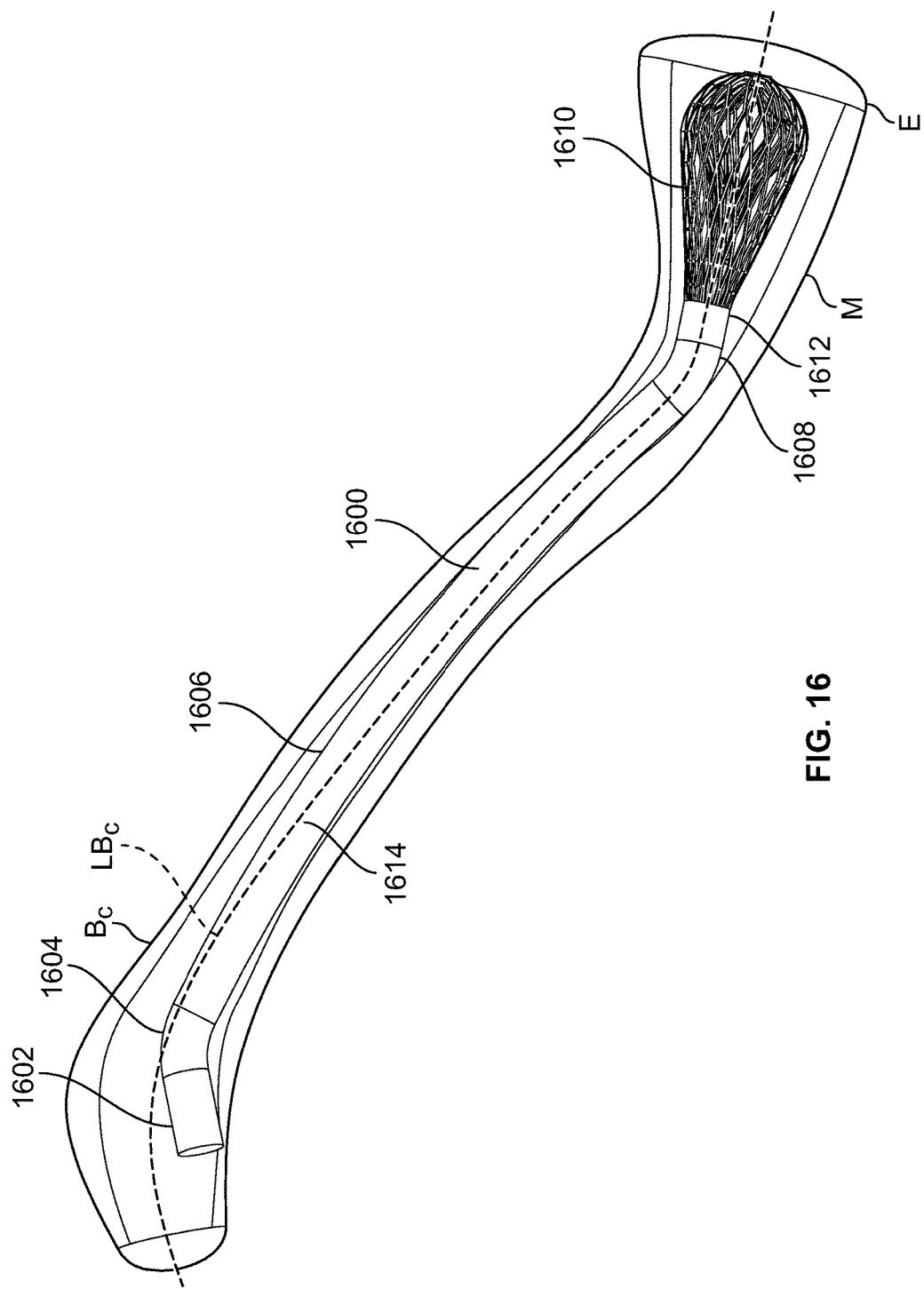
FIG. 16 shows other apparatus in accordance with the principles of the invention.

FIG. 16 shows illustrative rod 1600 in collarbone $B_c$. Rod 1600 may have one or features in common with rod 100. Rod 1600 may include one or more straight sections, such as section 1602. Rod 1600 may include one or more curved sections, such as sections 1604, 1606 and 1608. Bone support 1610 may extend from distal end 1612 of rod 1600. Bone support 1610 may be fixed to one or more bone fragments (not shown) in metaphysieal region M or epiphyseal region E of bone Bc using any suitable anchors (not shown).

Rod 1600 may include outer tubular member 1614. Rod 1600 may include an inner elongated member (not shown) that is disposed inside outer tubular member 1614. The inner elongated member may include segments that are configured to bend relative to neighboring segments along one or more pivot axes.

Outer tubular member 1614 may have stress relief features (not shown) that are distributed to cooperate with one or more of the pivot axes to allow rod 1600 to flex during insertion through a bone access hole (not shown) in bone $B_0$. The bone access hole may be at an angle with respect to axis LBC of bone $B_c$. Outer tubular member 1614 may have rigid features (not shown) that are distributed to interfere with one or more of the pivot axes. Rotation of outer tubular member 1614 relative to the inner elongated member may cause rod 1600 to become rigid in a curved or bent configuration to provide mechanical support to different portions of bone $B_c$.

Figure 17:
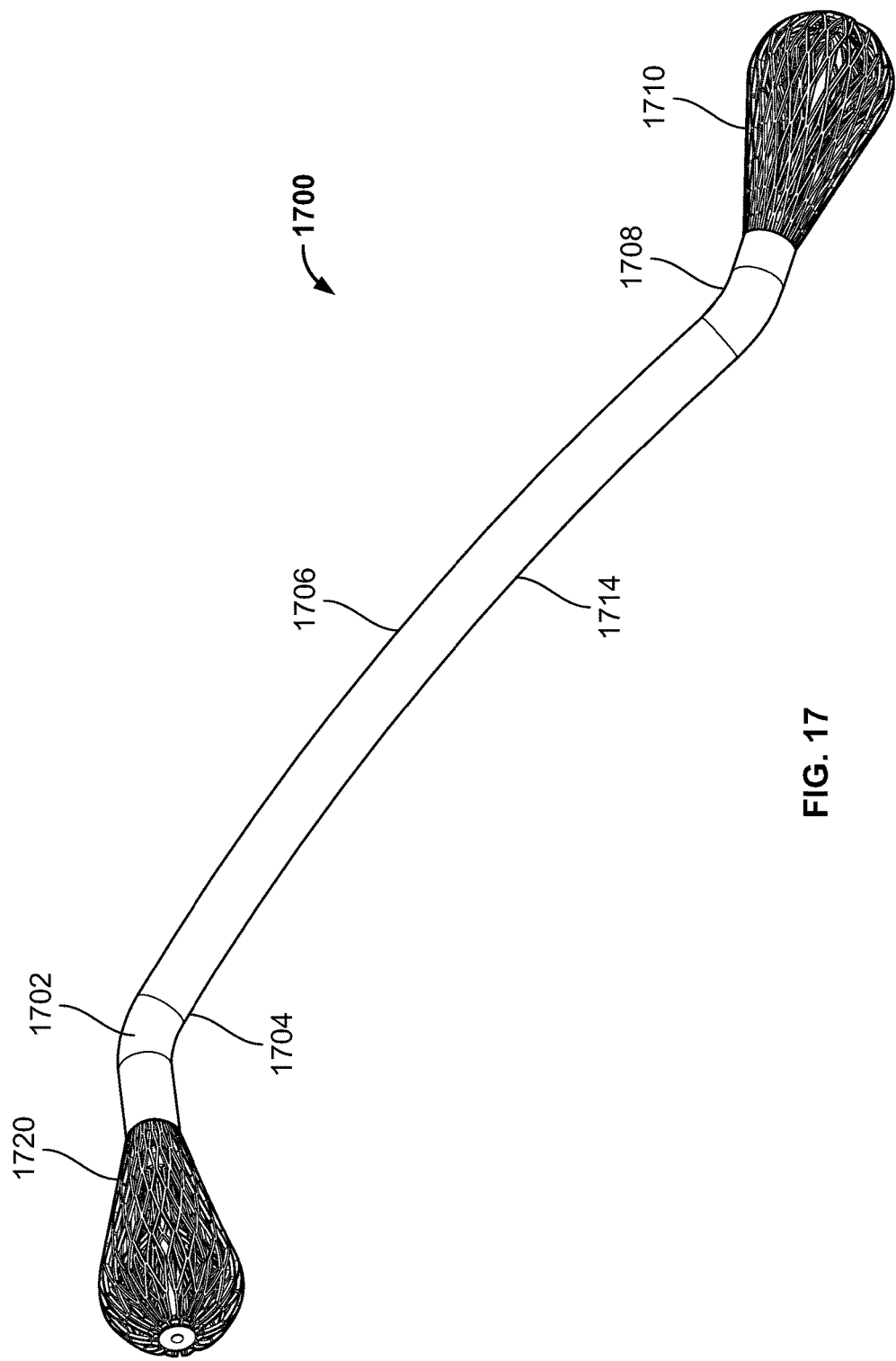
FIG. 17 shows yet other apparatus in accordance with the principles of the invention.

FIG. 17 shows illustrative rod 1700, which may have one or more features in common with rod 1600. Rod 1700 may include bone support 1710 for supporting one or more bone fragments at a distal end of bone $B_c$. Rod 1700 may include bone support 1710 for supporting one or more bone fragments at a proximal end of bone $B_c$. One or more of bone supports 1710 and 1720 may have one or more features in common with bone support 1610 (shown in FIG. 16).

Rod 1700 may include outer tubular member 1714. Rod 1700 may include an inner elongated member (not shown) that is disposed inside outer tubular member 1714. The inner elongated member may include segments that are configured to bend relative to neighboring segments along one or more pivot axes.

Rod 1700 may include one or more straight sections such as section 1702. Rod 1700 may include one or more curved or bent sections such as sections 1704, 1706 and 1708.

Figure 18:
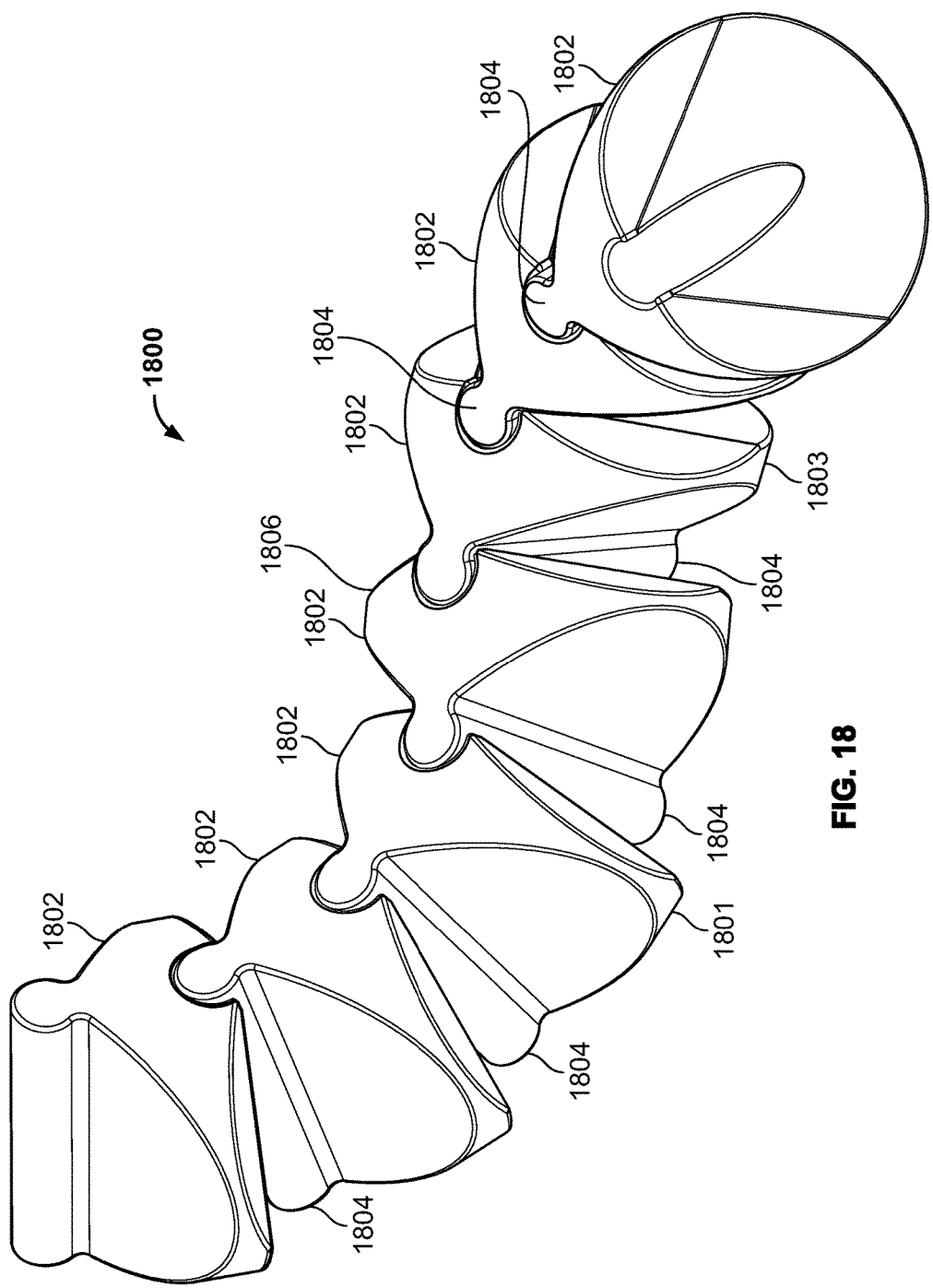
FIG. 18 shows still other apparatus in accordance with the principles of the invention.

FIG. 18 shows illustrative inner elongated member 1800. Inner elongated member 1800 may include segments 1802. Segments 1802 may be connected by linkages 1804. Exemplary segment 1806 will be discussed in connection with FIG. 19.

Figure 19:
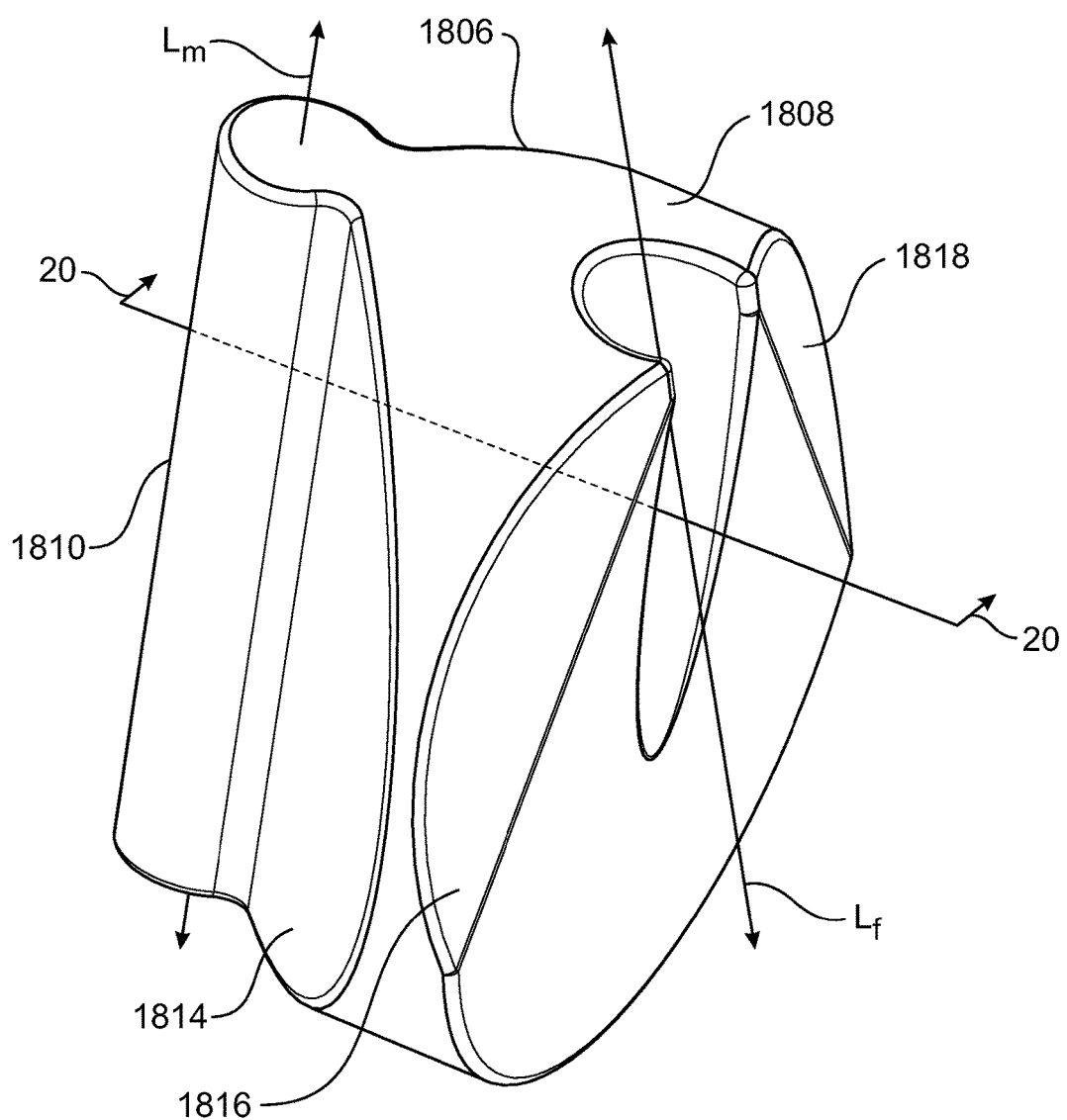
FIG. 19 shows a portion of the apparatus shown in FIG. 18.

FIG. 19 shows exemplary segment 1806. Segment 1806 may include body 1808. Segment 1806 may include male linkage member 1808 and female linkage member 1810 for linkage to neighboring segments 1802 (shown in FIG. 18). Body 1808 may include clearances, such as clearances 1814, 1816 and 1818, to reduce interference between segment 1806 and neighboring segments 1802.

Male linkage member 1808 may define pivot axis $L_m$ for articulation with neighboring segment 1801 (shown in FIG. 18). Female linkage member 1812 may define pivot axis $L_f$ for articulation with neighboring segment 1803. Pivot axes $L_m$ and $L_f$ are oblique and define two different bending axes for inner elongated member 1800. The corresponding outer tubular sleeve may be configured, at a first angular position relative to inner elongated member 1800, to permit bending about one or both of pivot axes $L_m$ and $L_f$. The outer tubular sleeve may be configured, at a second angular position relative to inner elongated member 1800, to prevent bending about one or both of pivot axes $L_m$ and $L_f$.

Figure 20:
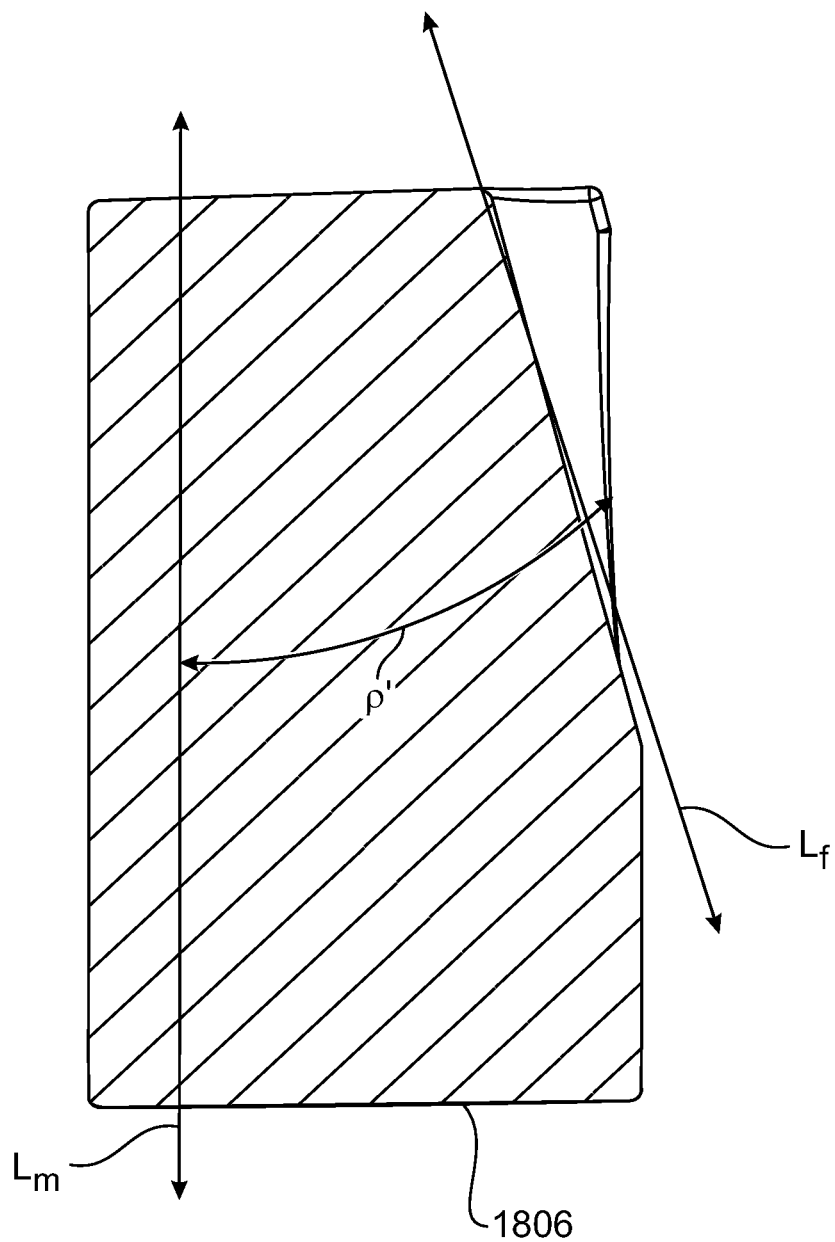
FIG. 20 shows a partial cross-sectional view, taken along lines 20-20 (shown in FIG. 19), of the apparatus shown in FIG. 19.

FIG. 20 shows angle $\rho'$, which corresponds to angle $\rho$ (shown in FIG. 15). Angle $\rho'$, along with any curvature in the body of segment 1806, may be the basis for rigid curvature when the rod is in its rigid state.

Figure 21:
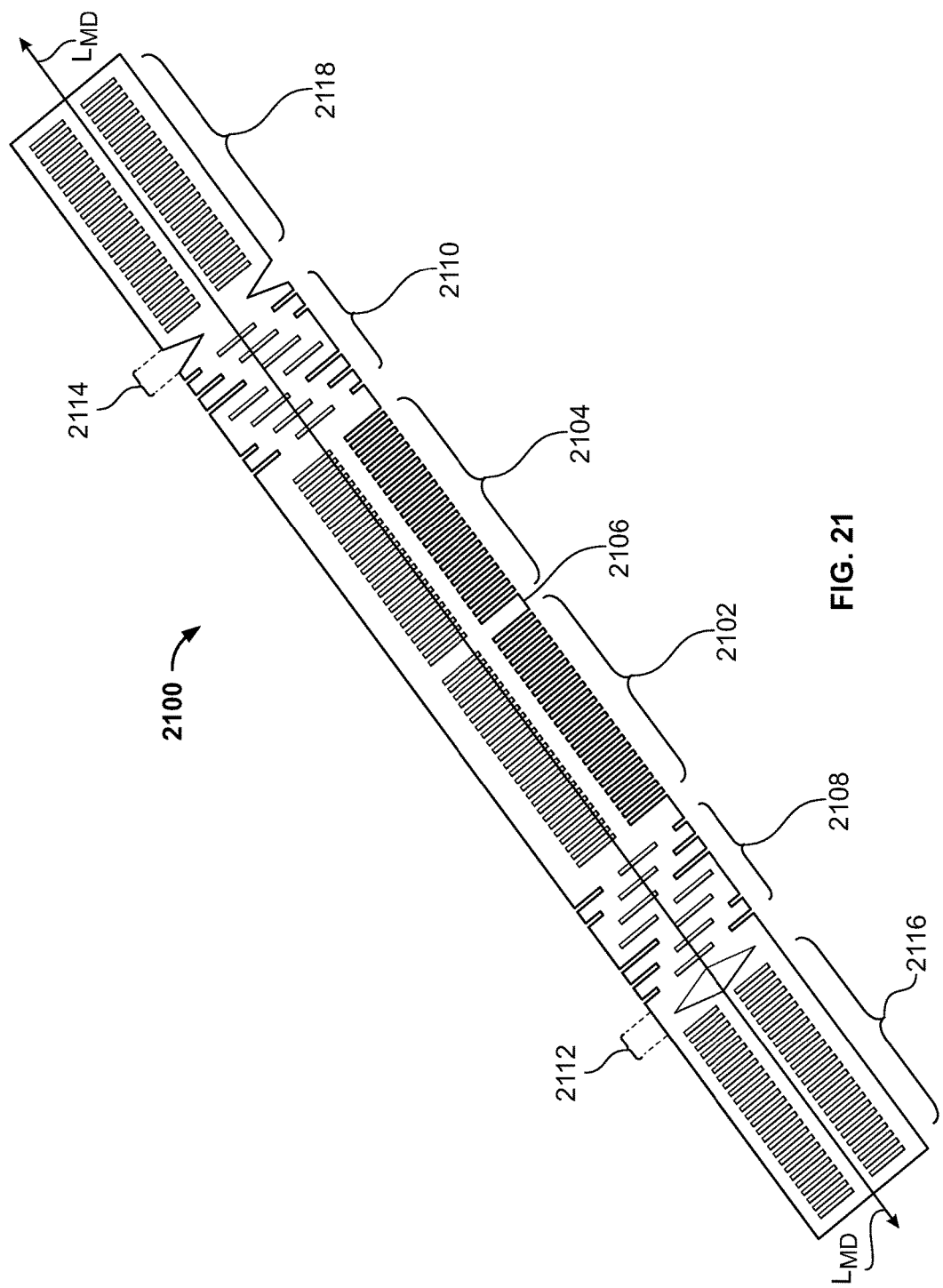
FIG. 21 shows a pattern that may be used to manufacture apparatus in accordance with the principles of the invention.

FIG. 21 shows illustrative cut-pattern 2100 for an outer tubular member such as 1614 (shown in FIG. 16). Pattern 2100 may be a laser-cut pattern. Pattern 2100, which is shown flat for illustration, may be cut in a cylindrical tube to provide stress relief in different directions that is distributed along axis $L_{MD}$ (shown projected onto cut-pattern 2100) of the outer tubular member.

Patterns 2102 and 2104, which may be similar to patterns 1302 and 1304 (shown in FIG. 13), may allow bending about a first axis that is normal to axis $L_{MD}$ (as shown, prior to deformation). Patterns 2102 and 2104 may be separated by rigid section 2106. Patterns 2108 and 2110 may allow helical bending about axis $L_{MD}$ (as shown, prior to deformation). The helix allowed by pattern 2108 may have an opposite sense of rotation from that of pattern 2110.

Pattern 2112 may allow a high degree of bending about a second axis that is normal to axis $L_{MD}$ (as shown, prior to deformation). Pattern 2114 may allow a high degree of bending about a third axis that is normal to axis $L_{MD}$ (as shown, prior to deformation).

Patterns 2116 and 2118, which may be similar to cut patterns 2102 and 2104, may allow bending about a fourth axis that is normal to axis LMD (as shown, prior to deformation). The fourth axis may be angularly offset, about axis LMD, with respect to the first axis (defined by cut patterns 2102 and 2104).

Figure 22:
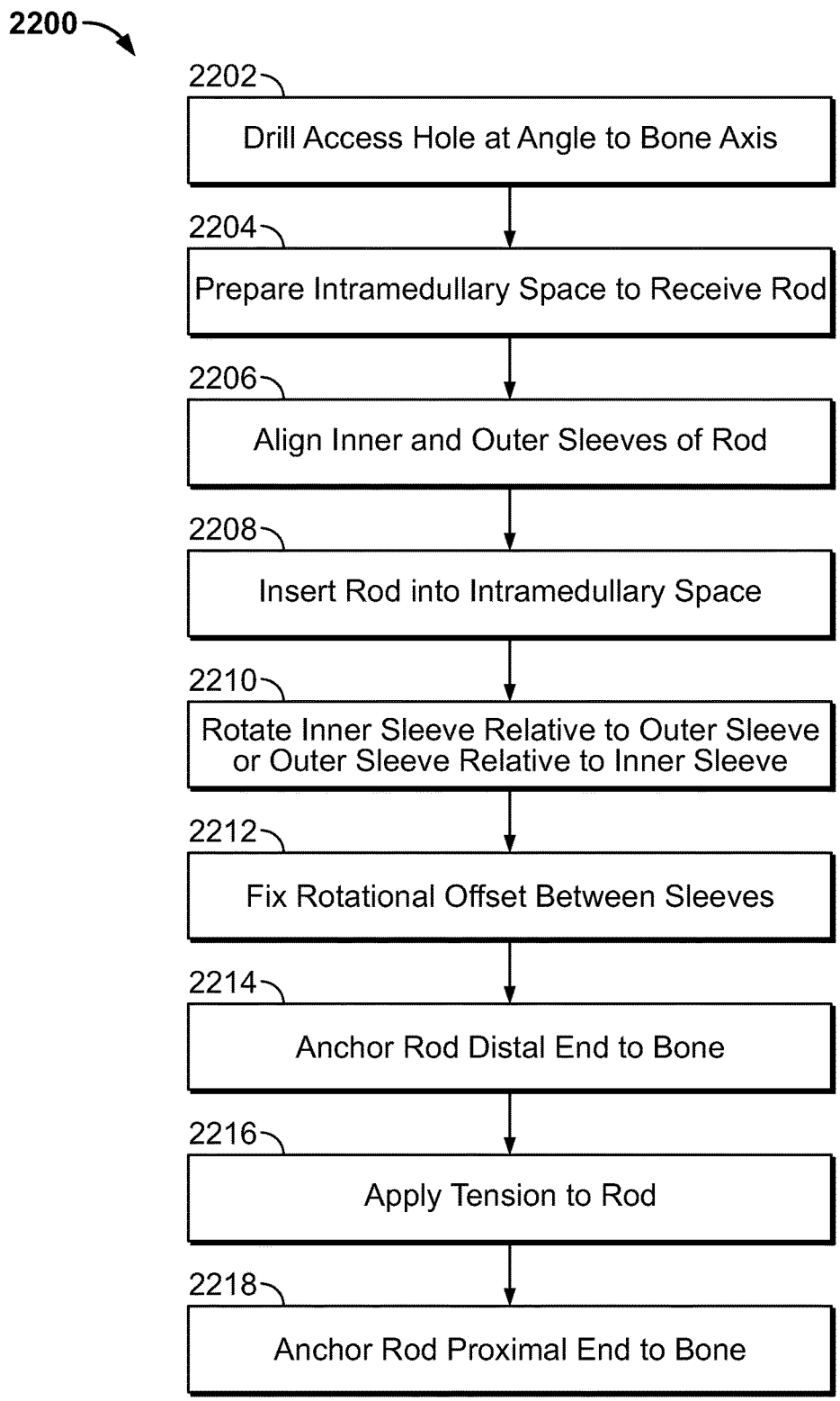
FIG. 22 shows illustrative steps of a process in accordance with the principles of the invention.

Processes in accordance with the principles of the invention may include one or more features of the processes illustrated in FIG. 22. The processes may involve the use of one or more of the apparatus shown and described herein. Some steps of the processes may be performed in an inpatient setting. Some steps of the processes may be performed in an outpatient setting.

The steps of the processes may be performed in an order other than the order shown and described herein. Some embodiments of the invention may omit steps shown and described in connection with the illustrative methods. Some embodiments of the invention may include steps that are not shown and described in connection with the illustrative methods.

FIG. 22 shows illustrative steps of process 2200 for repairing a fracture. At step 2202, a practitioner may drill an access hole at angle to a bone axis. At step 2204, the practitioner may prepare an intramedullary space in the bone to receive a rod. At step 2206, the practitioner may align inner and outer sleeves of rod to make the rod flexible. At step 2208, the practitioner may insert rod into the intramedullary space. At step 2210, the practitioner may rotate the inner sleeve relative to the outer sleeve or rotate the outer sleeve relative to the inner sleeve to reduce or eliminate flexibility of the rod. At step 2212, the practitioner may fix a rotational offset between sleeves. The practitioner may fix the rotational offset by actuating a mechanism that locks the sleeves with respect to each other, but does not necessarily lock the rod to the bone. At step 2214, the practitioner may anchor the rod distal end to the bone. At step 2216, the practitioner may apply tension to the rod. At step 2218, the practitioner may anchor the rod proximal end to the bone.

Thus, apparatus and methods for fracture repair have been provided. Persons skilled in the art will appreciate that the present invention can be practiced by other than the described embodiments, which are presented for purposes of illustration rather than of limitation. The present invention is limited only by the claims that follow.

What is claimed is:

1. An intramedullary rod defining a longitudinal axis and comprising:
   a first elongated member disposed coaxially within a second elongated member, the first elongated member having inner stress relief features and an inner longitudinal member and the second elongated member having outer stress relief features and an outer longitudinal member;
   wherein the elongated members are arranged such that:
   the rod is bendable when the first elongated member is circumferentially rotated about the longitudinal axis to align the outer stress relief features with the inner stress relief features; and
   the rod is rigid when the first elongated member is circumferentially rotated about the longitudinal axis to align the outer longitudinal member with the inner stress relief features.

2. The intramedullary rod of claim 1 wherein each of the outer stress relief features and the inner stress relief features correspond to an arrangement of slots that are longitudinally spaced from each other.

3. The intramedullary rod of claim 2 wherein the slots are configured to provide tension relief.

4. The intramedullary rod of claim 2 wherein the slots are configured to provide compression relief.

5. The intramedullary rod of claim 1 wherein:
   the outer stress relief features and the inner stress relief features correspond to:
   a first arrangement of slots that are longitudinally spaced from each other for tension relief; and
   a second arrangement of slots that are longitudinally spaced from each other to provide compression relief; and
   the first and second arrangements of slots are spaced circumferentially apart from each other on one of the elongated members.

6. The intramedullary rod of claim 1 wherein the first and second elongated members include, respectively, a first and second anchor receiving feature.

7. The intramedullary rod of claim 6 wherein the first and second elongated members are configured to be positioned relative to each other such that the first and second anchor receiving features are positioned to receive the same anchor.

8. The intramedullary rod of claim 7 wherein the first and second anchor receiving features are distal a first and a second arrangement of slots.

9. The intramedullary rod of claim 8 wherein the first and second elongated members include, respectively, a third and fourth anchor receiving feature.

10. The intramedullary rod of claim 9 wherein the third and fourth anchor receiving features are proximal the first and second arrangements of slots.

11. The intramedullary rod of claim 1 further comprising a locking mechanism that includes:
 a first adjustment flange attached to the first elongated member;
 a second adjustment flange attached to the second elongated member; and
 a setting element that is configured to prevent relative rotation about the longitudinal axis of the first elongated member with respect to the second elongated member.

12. The intramedullary rod of claim 11 wherein one of the first and second adjustment flanges is threaded.

13. The intramedullary rod of claim 1 further comprising a bone support extending from an end of one of the first and second elongated members.

14. The intramedullary rod of claim 13 further comprising, when the bone support is a first bone support and the end is a first end, a second bone support extending from a second end of one of the first and second elongated members.

15. An intramedullary rod defining a longitudinal axis and comprising a first elongated member disposed coaxially within and a second elongated member, the first elongated member having inner stress relief features and an inner longitudinal member and the second elongated member having outer stress relief features and an outer longitudinal member; wherein the elongated members are arranged such that the rod is more easily bendable when the first elongated member is circumferentially rotated about the longitudinal axis to align the outer stress relief features with the inner stress relief features than when the first elongated member is circumferentially rotated about the longitudinal axis to align the outer longitudinal member with the inner stress relief features.

16. The intramedullary rod of claim 15 wherein each of the outer stress relief features and the inner stress relief features corresponds to an arrangement of slots that are longitudinally spaced from each other.

17. The intramedullary rod of claim 16 wherein the slots are configured to provide tension relief.

18. The intramedullary rod of claim 16 wherein the slots are configured to provide compression relief.

19. The intramedullary rod of claim 15 wherein:
 the outer stress relief features and the inner stress relief features correspond to:
 a first arrangement of slots that are longitudinally spaced from each other for tension relief; and
 a second arrangement of slots that are longitudinally spaced from each other to provide compression relief; and
 the first and second arrangements of slots are spaced circumferentially apart from each other on one of the elongated members.

20. The intramedullary rod of claim 15 wherein the first and second elongated members include, respectively, a first and second anchor receiving feature.

21. The intramedullary rod of claim 20 wherein the first and second elongated members are configured to be positioned relative to each other such that the first and second anchor receiving features are positioned to receive the same anchor.

22. The intramedullary rod of claim 21 wherein the first and second anchor receiving features are distal a first and a second arrangement of slots.

23. The intramedullary rod of claim 22 wherein the first and second elongated members include, respectively, a third and fourth anchor receiving feature.

24. The intramedullary rod of claim 23 wherein the third and fourth anchor receiving features are proximal the first and second arrangements of slots.

25. The intramedullary rod of claim 15 further comprising a locking mechanism that includes:
 a first adjustment flange attached to the first elongated member;
 a second adjustment flange attached to the second elongated member; and
 a setting element that is configured to prevent relative rotation about the longitudinal axis of the first elongated member with respect to the second elongated member.

26. The intramedullary rod of claim 25 wherein one of the first and second adjustment flanges is threaded.

27. The intramedullary rod of claim 15 further comprising a bone support extending from an end of one of the first and second elongated members.

28. The intramedullary rod of claim 27 further comprising, when the bone support is a first bone support and the end is a first end, a second bone support extending from a second end of one of the first and second elongated members.

* * * * *

UNITED STATES PATENT AND TRADEMARK OFFICE
CERTIFICATE OF CORRECTION

PATENT NO. : 9,730,739 B2
APPLICATION NO. : 13/945137
DATED : August 15, 2017
INVENTOR(S) : Kyle Taylor et al.

It is certified that error appears in the above-identified patent and that said Letters Patent is hereby corrected as shown below:

In the Specification

Column 12, Line 33, replace "$B_0$" with --$B_c$--.

In the Claims

Claim 14, Line 20, replace "hone" with --bone--.
Claim 15, Line 25, replace "and a" with --a--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*